US009260742B2

(12) United States Patent
Siegel et al.

(10) Patent No.: US 9,260,742 B2
(45) Date of Patent: *Feb. 16, 2016

(54) METHODS FOR DETECTING ORGANISMS AND ENZYMATIC REACTIONS USING RAMAN SPECTROSCOPY

(75) Inventors: Neal Arthur Siegel, Morris, IL (US); Samar Kumar Kundu, Libertyville, IL (US); Charles Lester Ginsburgh, Westmont, IL (US)

(73) Assignee: SWORD DIAGNOSTICS, INC., Carmel (IN)

( * ) Notice: Subject to any disclaimer, the term of this patent is extended or adjusted under 35 U.S.C. 154(b) by 1074 days.

This patent is subject to a terminal disclaimer.

(21) Appl. No.: 13/040,679

(22) Filed: Mar. 4, 2011

(65) Prior Publication Data

US 2011/0183316 A1 Jul. 28, 2011

Related U.S. Application Data

(63) Continuation of application No. 12/081,496, filed on Apr. 16, 2008, now Pat. No. 7,947,437, which is a continuation-in-part of application No. 11/580,845, filed on Oct. 16, 2006, now Pat. No. 7,599,057.

(60) Provisional application No. 60/727,328, filed on Oct. 17, 2005, provisional application No. 60/836,936, filed on Aug. 11, 2006.

(51) Int. Cl.
*C12Q 1/00* (2006.01)
*G01J 3/44* (2006.01)
*C12Q 1/28* (2006.01)
*G01N 21/65* (2006.01)
*G01N 33/569* (2006.01)
*G01N 33/58* (2006.01)

(52) U.S. Cl.
CPC ........ *C12Q 1/28* (2013.01); *G01N 21/65* (2013.01); *G01N 33/56916* (2013.01); *G01N 33/56938* (2013.01); *G01N 33/56983* (2013.01); *G01N 33/581* (2013.01)

(58) Field of Classification Search
CPC ........................................................ C12Q 1/28
See application file for complete search history.

(56) References Cited

U.S. PATENT DOCUMENTS

| 7,599,057 | B2 * | 10/2009 | Siegel et al. ............... 356/301 |
| 7,947,437 | B2 * | 5/2011 | Siegel et al. .................. 435/4 |
| 8,243,267 | B2 * | 8/2012 | Siegel et al. ............... 356/300 |
| 2003/0059820 | A1 | 3/2003 | Vo-Dihn |
| 2008/0274489 | A1 | 11/2008 | Siegel et al. |
| 2010/0041016 | A1 | 2/2010 | Siegel et al. |
| 2010/0092942 | A1 | 4/2010 | Siegel et al. |

FOREIGN PATENT DOCUMENTS

| EP | 0033462 | 8/1981 |
| EP | 0 714 025 A1 | 5/1996 |
| EP | 0 725 271 A1 | 8/1996 |
| JP | 9-222395 | 8/1997 |
| JP | 2000258346 | 9/2000 |
| WO | WO 2004/007767 A2 | 1/2004 |
| WO | WO 2006/096468 A2 | 9/2006 |
| WO | WO 2006/104695 A2 | 10/2006 |
| WO | WO 2007/011778 A2 | 1/2007 |
| WO | WO 2007/047526 A1 | 4/2007 |
| WO | WO 2008/018933 A2 | 2/2008 |
| WO | WO 2009/128978 | 10/2009 |
| WO | WO 2010/096260 | 8/2010 |

OTHER PUBLICATIONS

Driskell, J.D., et al., "Low-Level Detection of Viral Pathogens by a Surface-Enhanced Raman Scattering Based Immunoassay," 77(19) Analytical Chemistry, 6147-6154 (2005).
Dou, X "Enzyme Immunoassay Utilizing Surface-Enhanced Raman Scattering of the Enzyme Reaction Product," Anal. Chem. 69: 1492-45 (1997).
Durckheimer, W. et al., "The Oxidative Conversion of Hydroquinone Monophoshates to Quinone Ketals," Biochemistry, 3:1948-1952 (1964).
Grow, A., et al., "New Biochip Technology for Label-Free Detection of Pathogens and Their Toxins," 53(2) Journal of Microbiological Methods, 221-223 (2003).
Ivnitski, D., et al., "Biosensors for detection of pathogenic bacteria," Biosensors & Bioelectronics, 14:599-624 (1999).
Másson, M. et al., "4-Amino-1-naphthylphosphate as a substrate for the amperometric detection of alkaline phosphatase activity and its application for immunoassay," Talanta, 64: 174-180 (2004).
Másson, M. et al., "4-Hydroxynaphtyl-1-phosphate as a substrate for alkaline phosphatase and its use in sandwich immunoassay," Analytica Chimica Acta, 402 (1999) 29-35.
Mosier-Boss, P.A., "Optical Properties of Surface-Enhanced Raman-Active Capture Matrices," 60(10) Applied Spectroscopy, 1148-1156 (2006). Mosier-Boss, P.A., "Optical Properties of Surface-Enhanced Raman-Active Capture Matrices," 60(10) Applied Spectroscopy, 1148-1156 (2006).
Mosier-Boss, P.A., et al., "Surface-Enhanced Raman Spectroscopy Substrate Composed of Chemically Modified Gold Colloid Particles Immobilized on Magnetic Microparticles," 77(4) Analytical Chemistry, 1031-1037 (2005).
Plastino et al "An Unexpected Role for the Active Site Base in Cofactor Orientation and Flexibility in the Copper Amine Oxidase from *Hansenula polymopha*," Biochemistry 38: 8204-16 (1999).
Rathore et al. "Direct Observation and Structural Characterization of the Encounter Complex in Bimolecular Electron Transfers with Photoactivated Acceptors," J. Am. Chem. Soc. 119: 11468-11480 (1997).

(Continued)

*Primary Examiner* — Albert Navarro
(74) *Attorney, Agent, or Firm* — Finnegan, Henderson, Farabow, Garrett & Dunner LLP

(57) ABSTRACT

The present disclosure provides systems for the rapid and sensitive detection of organisms and molecules in samples. Reactants that produce Raman-active products are used in combination with Raman light scattering. The present disclosure can also be used to measure enzyme-kinetics.

35 Claims, 43 Drawing Sheets

(56) References Cited

OTHER PUBLICATIONS

Santandreu, M. et al., "Amperometric Immunosensors Based on Rigid Conducting Immunocomposites," Analytical Chemistry, 69:2080-2085 (1997).

Sengupta, A., et al., "Bioaerosol Characterization by Surface-Enhanced Raman Spectroscopy (SERS)," 36(5-6) Journal of Aerosol Science; Measurement and Characterization of Bioaerosols, 651-664 (2005).

Tang, H. et al., "p-Aminophenyl Phosphate: An Improved Substrate for Electrochemical Enzyme Immunoassy," Analytica Chimica Acta, 214: 1987-195 (1988).

Wilson, M. et al., "Hydroquinone diphosphate: an alkaline phosphatase substrate that does not produce electrode fouling in electrochemical immunoassays," Biosensors & Bioelectronics, 20:276-283 (2004).

Xu Shuping et al., "Surface-Enhanced Raman Scattering Studies on Immunoassay," 10(3) Journal of Biomedical Optics, 1-12 (2005).

* cited by examiner

METHODS FOR DETECTING ORGANISMS AND ENZYMATIC REACTIONS USING RAMAN SPECTROSCOPY

CROSS-REFERENCE TO RELATED PATENT APPLICATIONS

This application is a Continuation of application Ser. No. 12/081,496, filed Apr. 16, 2008, now U.S. Pat. No. 7,947,437 which is a Continuation-In-Part of application Ser. No. 11/580,845, filed Oct. 16, 2006, now U.S. Pat. No. 7,599,057, which claims priority to Provisional Application No. 60/727,328, filed Oct. 17, 2005, and Provisional Application No. 60/836,936, filed Aug. 11, 2006, which are incorporated by reference in their entireties.

DESCRIPTION OF THE INVENTION

1. Field of the Invention

The present disclosure generally relates to the field of biological diagnostic equipment and testing methods.

2. Background of the Invention

There are currently many areas needing systems to detect biological organisms or components (e.g. proteins, DNA, or other genetic material). These areas include: food safety, medical and veterinary diagnostics, pathogen detection, forensics, and homeland security. Current detection methods include immunochemistry and molecular biology, and biological techniques such as Polymerase Chain Reaction (PCR) and Ligase Chain Reactions (LCR). These methods and techniques are often limited in accuracy, specificity, and sensitivity. Moreover, such methods often require extensive sample preparation, such as the isolation and purification of nucleic acids.

Specificity of detection methods can be enhanced by using immunological techniques. For example, medical diagnostics use antibody-based techniques to provide specificity in the detection of biological components of a sample. Antibodies developed to specific compounds are known to have high affinity and specificity for these components. However, antibodies are difficult to detect and are typically chemically modified with labels or tags that enhance detection. Unfortunately, antibody detection is prone to interference from other material in the sample including the sample matrix, wash components, and other chemical and biological agents. Moreover, current techniques lack sensitivity at low concentrations or numbers of antibodies (i.e. low concentrations or numbers of targeted biological components).

Raman light scattering techniques (Raman spectroscopy) have been used in the past to detect specific chemical components. Raman scattering is a basic property of the interaction of light with molecules. When light hits a molecule it can cause the atoms of the molecule to vibrate. This vibration will then change the energy of additional light scattered from the molecule. This scattered light has characteristics that are measurable and are unique to the structure of the vibrating molecule. Thus, a Raman spectrum can be used to uniquely identify a molecule.

Raman spectroscopy has several advantages over existing detection methods, including simple application and production of quantifiable data. However, Raman spectroscopy by itself lacks specificity and sensitivity for the detection of biological organisms and components. Therefore, there is a need in the art for reagents and methods that allow Raman spectroscopy to be used for detection of organisms and biological components.

The present disclosure is directed to methods that use the combination of Raman spectroscopy and biological labeling techniques to identify and quantify biological organisms and components with higher sensitivity and specificity than prior art techniques.

SUMMARY OF THE INVENTION

One embodiment of the disclosure is a method for detecting the activity of at least one enzyme in a sample comprising:
  a) preparing a mixture comprising the sample and:
    i. (optionally) at least one aromatic compound;
    ii. at least one amine-containing compound; and
    iii. at least one electron-donating compound;
  b) incubating the mixture to form at least one Raman-active product; and
  c) detecting the at least one Raman-active product with Raman spectroscopy.

In one embodiment, the at least one amine-containing compound is chosen from 4-aminoantipyrene and 5-aminosalicylic acid.

In another embodiment, the at least one aromatic compound is chosen from 2-hydroxybenzyl alcohol, 4-chloro-3,5-dimethylphenol, 2-naphthol, 4-hydroxy-4-biphenyl-carboxylic acid, 5,7dichloro-8-hydroxyquinoline, 4-chloro-1-naphthol, phenol, and 4,5 dihydroxy-naphthelene-2,7-disulfonic acid.

In another embodiment, the at least one amine-containing compound comprises:

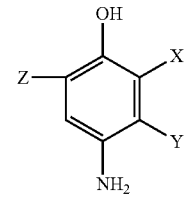

wherein X is chosen from H, $NH_2$, Cl, Br, nitro, and benzyl, Y is chosen from H, Cl, Br, and nitro, and Z is chosen from H, benzyl, and $NH_2$. In one embodiment, X is $NH_2$, and Y and Z are H. In another embodiment, X is Cl, and Y and Z are H. In another embodiment, X is Br, and Y and Z are H. In another embodiment, X is nitro, and Y and Z are H. In another embodiment, X and Z are H and Y is Cl. In another embodiment, X and Z are H and Y is Br. In another embodiment, X and Z are H and Y is nitro. In another embodiment, X and Z are benzyl and Y is H. In another embodiment, X and Z are $NH_2$ and Y is H.

In another embodiment, the at least one amine-containing compound comprises:

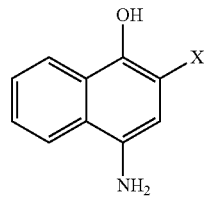

wherein X is chosen from H, OH, Cl, Br, and nitro.

In another embodiment, the at least one amine-containing compound comprises:

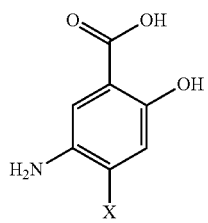

wherein X is chosen from H, Cl, Br, and nitro.

In another embodiment, the at least one aromatic compound comprises:

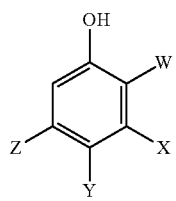

wherein W, X, Y, and Z are chosen from H and OH. In one embodiment, Y is OH and X, Y and Z are H. In another embodiment, W is OH, and X, Y and Z are H. In another embodiment, W and X are OH, and Y and Z are H. In another embodiment, W and Y are OH, and X and Z are H. In another embodiment, W and Z are OH and X and Y are H.

In another embodiment, the at least one aromatic compound comprises:

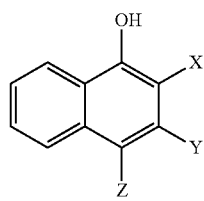

wherein X, Y, and Z are chosen from H and OH. In one embodiment, X is OH and Y and Z are H. In another embodiment, X and Y are OH and Z is H. In another embodiment X and Z are OH and Y is H. In another embodiment, Z is OH and X and Y are H.

In another embodiment, the at least one aromatic compound comprises:

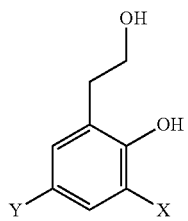

wherein X and Y are chosen from H and OH. In one embodiment X is OH and Y is H. In another embodiment, X is H and Y is OH.

In another embodiment, the at least one aromatic compound comprises:

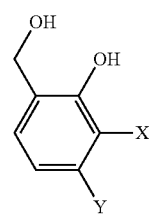

wherein X and Y are chosen from H and OH. In one embodiment, X is OH and Y is H. In another embodiment, X is H and Y is OH.

In another embodiment, the at least one amine-containing compound comprises an aromatic amine. In another embodiment, the aromatic amine comprises ortho-phenylenediamine, meta-phenylenediamine, or para-phenyleneamine:

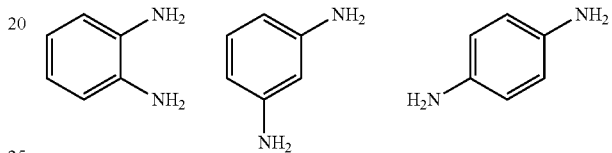

In another embodiment, the at least one electron-donating compound is a hydrogen peroxide. In another embodiment, the hydrogen peroxide is chosen from an aromatic hydrogen peroxide, urea hydrogen peroxide and hydrogen peroxide ($H_2O_2$). In another embodiment, the at least one enzyme is a peroxidase.

In another embodiment, the at least one aromatic compound is 2-hydroxybenzyl alcohol, the at least one amine containing compound is 5-aminosalicyclic acid, the at least one electron-donating compound is urea hydrogen peroxide, and the at least one enzyme is a peroxidase.

In another embodiment, the mixture is incubated in the presence of a base.

In another embodiment, the Raman spectroscopy is resonance Raman spectroscopy.

Another embodiment is a method for detecting the activity of at least one enzyme in a sample comprising:
  a) preparing a mixture comprising the sample, 5-aminosalicyclic acid, and a hydrogen peroxide chosen from an aromatic hydrogen peroxide, urea hydrogen peroxide, and hydrogen peroxide $H_2O_2$;
  b) incubating the mixture to form at least one Raman-active product; and
  c) detecting the at least one Raman-active product with Raman spectroscopy.

In one embodiment, the mixture further comprises biotin.

Another embodiment is a method for detecting the activity of at least one enzyme in a sample comprising:
  a) preparing a mixture comprising the sample, an aromatic amine comprising o-phenylenediamine, p-phenylenediamine, or m-phenylenediamine, and a hydrogen peroxide chosen from an aromatic hydrogen peroxide, urea hydrogen peroxide and $H_2O_2$;
  b) incubating the mixture to form at least one Raman-active product; and
  c) detecting the at least one Raman-active product with Raman spectroscopy.

Another embodiment is a method for detecting at least one target in a sample comprising:
  a) preparing a mixture comprising the target;
  b) incubating the mixture with at least one ligand specific for the target, wherein the at least one ligand comprises an enzyme;

c) providing to the mixture:
   i. optionally, at least one amine-containing compound;
   ii. at least one aromatic compound; and
   iii. at least one electron-donating compound;
d) incubating the mixture to form at least one Raman-active product; and
e) detecting the at least one Raman-active product with Raman spectroscopy.

In one embodiment, the at least one amine-containing compound is chosen from 4-aminoantipyrene and 5-aminosalicylic acid. In another embodiment, the at least one aromatic compound is chosen from 2-hydroxybenzyl alcohol, 4-chloro-3,5-dimethylphenol, 2-naphthol, 4-hydroxy-4-biphenyl-carboxylic acid, 5,7-dichloro-8-hydroxyquinoline, 4-chloro-1-naphthol, phenol, and 4,5 dihydroxy-naphthelene-2,7-disulfonic acid.

In another embodiment, the at least amine containing compound comprises:

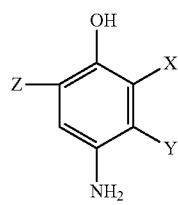

wherein X is chosen from H, NH$_2$, Cl, Br, nitro, and benzyl, Y is chosen from H, Cl, Br, and nitro, and Z is chosen from H, benzyl, and NH$_2$. In one embodiment, X is NH$_2$, and Y and Z are H. In another embodiment, X is Cl, and Y and Z are H. In another embodiment, X is Br, and Y and Z are H. In another embodiment, X is nitro, and Y and Z are H. In another embodiment, X and Z are H and Y is Cl. In another embodiment, X and Z are H and Y is Br. In another embodiment, X and Z are H and Y is nitro. In another embodiment, X and Z are benzyl and Y is H. In another embodiment, X and Z are NH$_2$ and Y is H.

In another embodiment, the at least one amine-containing compound comprises:

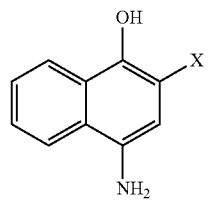

wherein X is chosen from H, OH, Cl, Br, and nitro.

In another embodiment, the at least one amine-containing compound comprises:

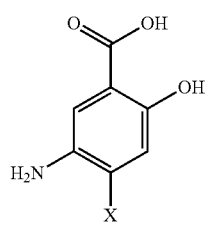

wherein X is chosen from H, Cl, Br, and nitro.

In another embodiment, the at least one aromatic compound comprises:

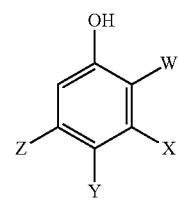

wherein W, X, Y, and Z are chosen from H and OH. In one embodiment, Y is OH and X, Y and Z are H. In another embodiment, W is OH, and X, Y and Z are H. In another embodiment, W and X are OH, and Y and Z are H. In another embodiment, W and Y are OH, and X and Z are H. In another embodiment, W and Z are OH and X and Y are H.

In another embodiment, the at least one aromatic compound comprises:

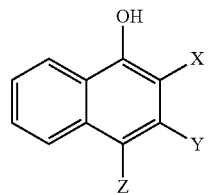

wherein X, Y and Z are chosen from H and OH. In one embodiment, X is OH and Y and Z are H. In another embodiment, X and Y are OH and Z is H. In another embodiment X and Z are OH and Y is H. In another embodiment, Z is OH and X and Y are H.

In another embodiment, the at least one aromatic compound comprises:

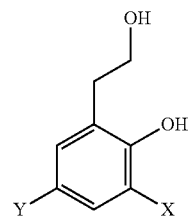

wherein X and Y are chosen from H and OH. In one embodiment X is OH and Y is H. In another embodiment, X is H and Y is OH.

In another embodiment, the at least one aromatic compound comprises:

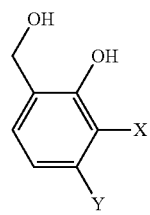

wherein X and Y are chosen from H and OH. In one embodiment, X is OH and Y is H. In another embodiment, X is H and Y is OH.

In another embodiment, the at least one amine-containing compound comprises an aromatic amine comprising ortho-phenylenediamine, meta-phenylenediamine, or para-phenyleneamine:

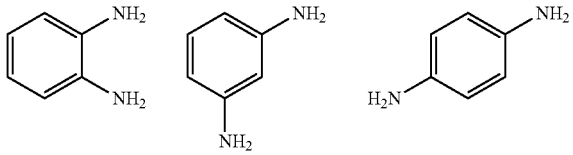 [SMILES: Nc1ccccc1N ; Nc1cccc(N)c1 ; Nc1ccc(N)cc1]

In another embodiment, the at least one electron-donating compound is chosen from an aromatic hydrogen peroxide, urea hydrogen peroxide and hydrogen peroxide ($H_2O_2$).

In another embodiment the enzyme is a peroxidase.

In another embodiment the at least one aromatic compound is 2-hydroxybenzyl alcohol, the amine-containing compound is 5-aminosalicyclic acid, the electron-donating compound is urea hydrogen peroxide, and the enzyme is a peroxidase.

In another embodiment, the mixture is incubated in the presence of a base.

In another embodiment, the Raman spectroscopy is resonance Raman spectroscopy.

In another embodiment, the ligand is chosen from a receptor and an antibody. In another embodiment, the ligand is an antibody.

In another embodiment, the at least one target is an organism. In another embodiment, the organism is chosen from a bacteriophage, a bacterium, including *E. coli, Listeria, Salmonella, Vibrio, Camphelbacter*, and *Staphylococcus*, and viruses such as HIV, Hepatitis, Adenovirus, Rhino virus, Human papilloma virus.

In another embodiment the target is a component of an organism. In one embodiment, the component is a protein. In another embodiment, the protein is an interleukin. In one embodiment, the interleukin is IL-2. In another embodiment, the protein is chosen from C-Reactive protein, Tumor Necrosis Factor Receptor II, and Human Cardiac Troponin I. In another embodiment, the target is a component of an organism chosen from amino acids, nucleic acids, nucleotides, metabolites, carbohydrates, hormones, and metabolic intermediates.

Another embodiment is a method for detecting the activity of an enzyme in a sample comprising:
  a) preparing a mixture comprising the sample and:
    i. optionally at least one aromatic compound;
    ii. at least one amine-containing compound; and
    iii. at least one electron-donating compound;
  b) incubating the mixture to form at least one charge transfer complex; and
  c) detecting the at least one charge transfer complex with Raman spectroscopy.

Another embodiment is a kit for detecting at least one enzyme activity comprising:
  a) (optionally) at least one aromatic compound;
  b) at least one amine-containing compound;
  c) at least one electron-donating compound; and
  d) (optionally) suitable buffers for the at least one enzyme.

In one embodiment, the at least one amine-containing compound is chosen from 4-aminoantipyrene, 5-aminosalicyclic acid, and o-phenylenediamine; the at least one aromatic compound is chosen from 2-hydroxybenzyl alcohol, 4-chloro-3,5-dimethylphenol, 2-naphthol, 4-hydroxy-4-biphenyl-carboxylic acid, 5,7-dichloro-8-hydroxyquinoline, 4-chloro-1-naphthol, phenol, and 4,5 dihydroxy-naphthelene-2,7-disulfonic acid; and the at least one electron-donating compound is chosen from an organic hydrogen peroxide, urea hydrogen peroxide, and hydrogen peroxide ($H_2O_2$).

In another embodiment, the at least one amine-containing compound comprises:

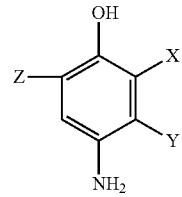

wherein X is chosen from H, $NH_2$, Cl, Br, nitro, and benzyl, Y is chosen from H, Cl, Br, and nitro, and Z is chosen from H, benzyl, and $NH_2$. In one embodiment, X is $NH_2$, and Y and Z are H. In another embodiment, X is Cl, and Y and Z are H. In another embodiment, X is Br, and Y and Z are H. In another embodiment, X is nitro, and Y and Z are H. In another embodiment, X and Z are H and Y is Cl. In another embodiment, X and Z are H and Y is Br. In another embodiment, X and Z are H and Y is nitro. In another embodiment, X and Z are benzyl and Y is H. In another embodiment, X and Z are $NH_2$ and Y is H.

In another embodiment, the at least one amine-containing compound comprises:

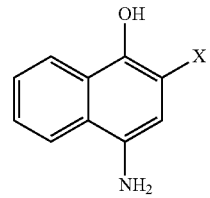

wherein X is chosen from H, OH, Cl, Br, and nitro.

In another embodiment, the at least one amine-containing compound comprises:

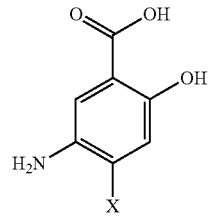

wherein X is chosen from H, Cl, Br, and nitro.

In another embodiment, the at least one aromatic compound comprises:

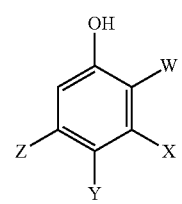

wherein W, X, Y, and Z are chosen from H and OH. In one embodiment, Y is OH and X, Y and Z are H. In another embodiment, W is OH, and X, Y and Z are H. In another embodiment, W and X are OH, and Y and Z are H. In another embodiment, W and Y are OH, and X and Z are H. In another embodiment, W and Z are OH and X and Y are H.

In another embodiment, the at least one aromatic compound comprises:

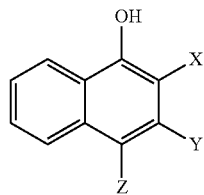

wherein X, Y and Z are chosen from H and OH. In one embodiment, X is OH and Y and Z are H. In another embodiment, X and Y are OH and Z is H. In another embodiment X and Z are OH and Y is H.

In another embodiment, the at least one aromatic compound comprises:

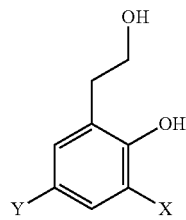

wherein X and Y are chosen from H and OH. In one embodiment X is OH and Y is H. In another embodiment, X is H and Y is OH.

In another embodiment, the at least one aromatic compound comprises:

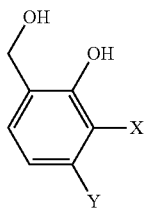

wherein X and Y are chosen from H and OH. In one embodiment, X is OH and Y is H. In another embodiment, X is H and Y is OH.

In another embodiment, the at least one amine-containing compound comprises an aromatic amine comprising ortho-phenylenediamine, meta-phenylenediamine, or para-phenyleneamine:

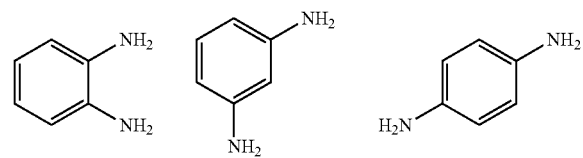 [SMILES: Nc1ccccc1N ; Nc1cccc(N)c1 ; Nc1ccc(N)cc1]

BRIEF DESCRIPTION OF THE DRAWINGS

The patent or application file contains at least one drawing executed in color. Copies of the patent or patent application publication with color drawing(s) will be provided by the Office upon request and payment of the necessary fee.

DETAILED DESCRIPTION OF THE INVENTION

Figure 1:
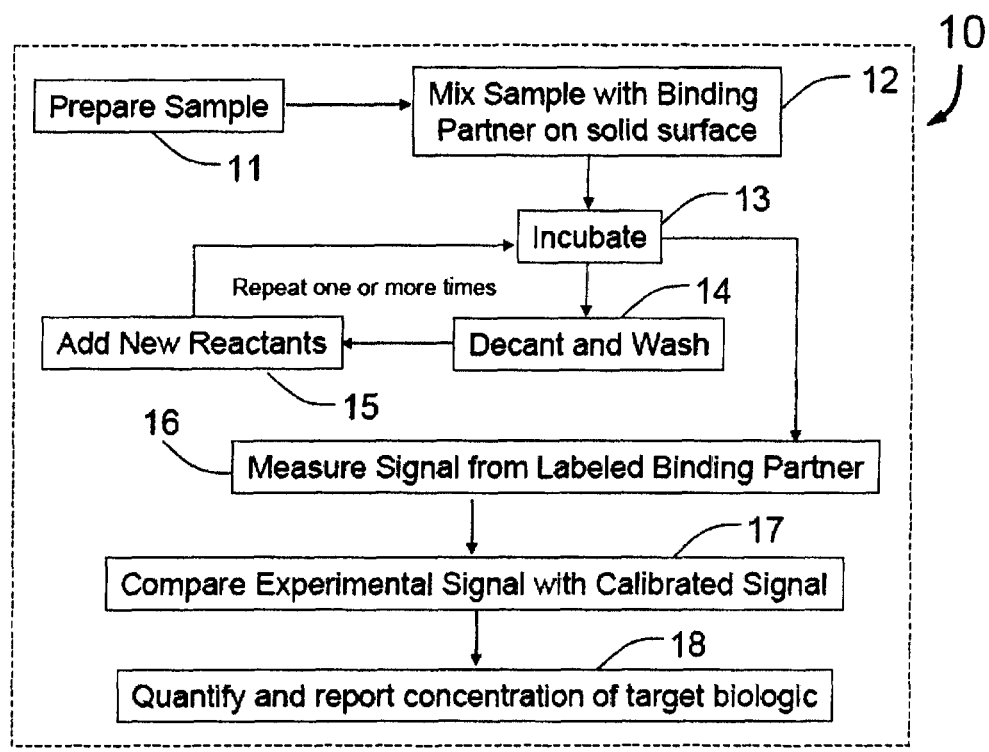
FIG. 1 is a flow chart of a typical prior art immunoassay technique (ELISA) for the detection of biological organisms or components.

Areas such as food safety, medical diagnostics, veterinary diagnostics, pathogen detection, forensics, and homeland security require the rapid and specific identification of biological organisms, such as contaminating bacteria, and biological components such as proteins, DNA, or other genetic material. Of particular need in the art are rapid and sensitive methods for detecting bacteria.

A common assay to identify a bacterium in a sample is an immunoassay, which relies on detecting an antibody bound to the bacterium. Typically, the antibody is labeled and the presence of the antibody is detected by assaying for the presence of the label. Alternatively the antibody is conjugated to an enzyme, and the presence of the antibody-enzyme conjugate is detected by assaying for enzymatic activity. A commonly used assay that employs an enzyme-antibody conjugate is the enzyme linked immunosorbant assay (ELISA). In standard assays, enzymatic activity can be measured by incubating the enzyme-antibody conjugate in the presence of reactants that are converted by the enzyme into products which can be detected through colorimetric, fluorogenic, and chemiluminscent means.

However, detection by colorimetric, fluorogenic, and chemiluminscent means suffers from several deficiencies such as limited dynamic range, limited sensitivity, and interference from background.

While Raman spectroscopy has several advantages over these methods, it generally cannot be used in combination with commonly used colorimetric, fluorogenic, and chemiluminscent reagents because they typically do not produce useful Raman spectra. For example, the colorimetric reagents 3,3',5,5'-tetramethelene benzidine (TMB), and azinobisethlybenzthiazolinesulfonic acid (ABTS) do not produce Raman spectra useful for detecting organisms. Accordingly, reagents that produce Raman-active products useful for detecting organisms are desired, including reagents that can be used in immunoassay formats employing enzyme-antibody conjugates.

Reagents useful for detecting a bacterium in an immunoassay format using Raman spectroscopy have certain desired characteristics. First, the reagents should produce a Raman signal in an area of the Raman spectrum that does not already have background signal produced by the bacterium. Second, the Raman signal produced by the reagents should be quantifiable, allowing for detection over a wide range of concentrations.

The present disclosure is based in part on the discovery that certain amine-containing compounds can be used in immunoassay formats to detect organisms and components, such as nucleic acids and proteins. These reagents are enzymatically converted to produce iminoquinone or other products that have Raman signals at spectral regions not already containing Raman signals from the bacterium. Detection of the Raman signals indicates the presence of the enzyme. When the enzyme is part of an antibody-conjugate used in an ELISA assay, detection of Raman signals indicates the presence of the target of the ELISA. Alternatively, Raman-active reagents can be incubated with enzymes that convert these reagents into products with Raman spectra that differ from the reagents. The change in the Raman signal indicates the presence of the enzyme. Accordingly, use of these reagents allows for the rapid, specific and quantitative detection of enzymatic activity.

The present disclosure is also based in part on the discovery that certain combinations and amounts of the reagents of the disclosure produce superior sensitivity. This sensitivity can be further enhanced through use of the Single Quantifiable Result (SQR) method of the disclosure, which employs multiple wavenumber spectroscopic analyses.

The present disclosure is also based in part on the discovery that the colorimetric reagent o-phenylenediamine (OPD) can be used to produce Raman-active products, in contrast to other colorimetric reagents. OPD can be used in combination with Raman spectroscopy to measure real-time kinetics of enzyme activity.

While not being bound by any theory, it is believed that the present disclosure is based on the ability of certain compounds to form charge-transfer complexes that can be detected by Raman spectroscopy. The presence of such complexes is supported by the discovery that these compounds produce broad Raman peaks consistent with formation of charge transfer complexes. See, e.g., Rathore et al., "Direct Observation and Structural Characterization of the Encounter Complex in Bimolecular Electron Transfers with Photoactivated Acceptors," J. Am. Chem. Soc. 119: 11468-11480 (1997). The discovery that certain compounds produce Raman-detectable charge transfer complexes provides a means to select reactants that will produce such complexes.

DEFINITIONS

"Antibody", as used herein, means an immunoglobulin or a part thereof, and encompasses any polypeptide comprising an antigen-binding site regardless of the source, method of production, and other characteristics. The term includes for example, polyclonal, monoclonal, monospecific, polyspecific, humanized, single-chain, chimeric, synthetic, recombinant, hybrid, mutated, and CDR-grafted antibodies. A part of an antibody can include any fragment which can still bind antigen, for example, an Fab, $F(ab')_2$, Fv, scFv. The origin of the antibody is defined by the genomic sequence irrespective of the method of production.

The terms "polypeptide," "peptide," and "protein," are used interchangeably to refer to a polymeric form of amino acids of any length, which can include naturally-occurring amino acids, coded and non-coded amino acids, chemically or biochemically modified, derivatized, or designer amino acids, amino acid analogs, peptidomimetics, and depsipeptides, and polypeptides having modified, cyclic, bicyclic, depsicyclic, or depsibicyclic peptide backbones. The term includes single chain protein as well as multimers.

The term "amino acid" refers to monomeric forms of amino acids, which can include naturally-occurring amino acids, coded and non-coded amino acids, chemically or biochemically modified, derivatized, or designer amino acids, amino acid analogs, peptidomimetics, and depsipeptides.

The terms "polynucleotide," "nucleic acid," "nucleic acid sequence," "polynucleotide sequence," and "nucleotide sequence" are used interchangeably herein to refer to polymeric forms of nucleotides of any length. The polynucleotides can comprise deoxyribonucleotides, ribonucleotides, and/or their analogs or derivatives.

The term "nucleotide," refers to monomeric nucleotides and includes deoxyribonucleotides, ribonucleotides, and/or their analogs or derivatives.

The term "ligand" refers to a molecule that binds to another molecule, including a receptor.

Immunoassay Formats

The present disclosure can be practiced in various formats. In one embodiment, the format is an immunoassay. In certain immunoassay embodiments, a target biologic is first bound to an antibody that attached to a solid surface. Unbound components of the test sample are then optionally washed away leaving only the bound biologic/antibody combinations, which can be detected by Raman scattering of ultraviolet light.

In one embodiment, a combination of Raman spectroscopy and biological labeling techniques are used to identify and quantify biological components, such as proteins or peptides including any post-translational modifications, in specific conformations or conditions associated with disease: for example, prion proteins.

To increase the sensitivity an additional step is envisioned where one or more new reactants are then introduced and become bound to the biologic/antibody combination. The combination of the new reactant(s) with the biologic/antibody combination can now be detected using Raman scattering of light. Examples of such reactants include, but are not limited to the reagents listed in Table 1.

TABLE 1

Sensitivity Enhancing Reagents 1. antibodies labeled with Raman-active molecules;
2. enzyme/antibody conjugates combined with additional chemical reactants that react to form Raman-active molecules;
3. Raman-active reactants that chemically interact with the biologic; and
4. chemical reactants that are converted by the biologic into Raman-active molecules.

It is also envisioned that instead of starting with a biologic/antibody combination, the Raman detection methods can use chemicals that interact with the biologic without the antibody.

The Raman-based methods can be applied to many immunoassays including, but not limited to, the detection of Human IL-11, Rat-C Reactive Protein, Soluble Tumor Necrosis Factor Receptor II, and Human Cardiac Troponin I.

The Raman-based methods can be applied to the detection of variety of organisms and components. In one embodiment, bacteriophage are detected. In another embodiment, bacteria, including *E. coli, Listeria, Salmonella, Vibrio, Camphelbacter*, and *Staphylococcus* and detected. In another embodiment, viruses such as HIV, Hepatitis, Adenovirus, Rhino virus, Human papilloma virus are detected. In another embodiment components, including proteins, amino acids, nucleic acids, nucleotides, metabolites, hormones, and metabolic intermediates are detected.

It is also envisioned that specific binding partners or ligands for the target biologic other than antibodies may be used, for example, a biological receptor (a protein).

Although many of the techniques disclosed herein are associated with the detection of biological organisms and components, the disclosure is applicable to the detection of inorganic components, organic components, contaminants, or toxins in a sample. The disclosed detection techniques can be enhance by using reactants that exhibit resonance Raman light scattering. For certain reactants, there are frequencies of scattered light that are more intense which are specific to the structure of these reactants. The resonance phenomena in certain embodiments of the present disclosure is solely related to the chemical structure and interaction of the target molecule, and not to any solid surface interaction such as found in the technique known as Surface Enhanced Resonance Raman Scattering (SERRS).

Single Quantifiable Result (SQR)

Raman spectra can be analyzed by obtaining a Single Quantifiable Result (SQR). The SQR number is the difference between a Raman spectra corresponding to a targeted analyte measured in a sample, and any background Raman signal/spectra observed in the measurement process. The steps of the SQR process are shown in Table 2.

TABLE 2

SQR Procedure

1) Optionally, spectra for the background of the sample (Negative Control) and for the samples being investigated (Test Samples) are measured.
2) The Raman values for a range of wave numbers, such as every 2nd wave number, or for every wave number, for the Negative Control and Test Samples are measured.
3) The difference between the Raman value for the Test Sample and the Negative Control is determined for each wave number measured and the sum of these values is calculated ("Sum of the Differences").
4) The difference between each Raman value for the Test Sample and the Negative Control is squared and the sum of these values is calculated ("Sum of the Squares of the Differences").
5) The square root of the "Sum of the Squares of the Differences" is calculated ("Square Root of the Sum of the Squares of the Differences"). This value is designated as the SQR value.

The SQR process can include an assessment of whether the Raman signals from the sample and background are appropriate (i.e. "valid") and sufficient to indicate the presence of the targeted analyte in the sample (i.e. "positive value"). The SQR process may be performed manually or with designed computer software. The Raman signals for multiple wave numbers are tabulated for the background and test spectra. In one embodiment, every $2^{nd}$ wave number is tabulated for both the background and test spectra. In another embodiment, every wave number is tabulated for both the background and test spectra. In one embodiment the range of wave numbers is from 2,000 to 4,000 cm$^{-1}$. In another embodiment, the range of wave numbers is from 3500 to 4000 cm$^{-1}$. The difference between the test signal and background signal is determined for a range of wave numbers and the square of this difference is stored. The sum of the squares is determined, and the square root of this sum is the SQR value.

When using SQR, its validity can be verified by ensuring that the negative and/or sample run is run appropriately (no systematic error resulting in an incorrect assay), so that the Raman spectra has the intended meaning. If a background measurement is used, the background sample must be representative of the background signal in the test samples, and not due to random signal such as signal obtained when Raman readings are taken without a sample tube in the instrument. Sample spectra must not consistently run below (less than) that of the negative control. Mathematically, the difference between a lower running sample and the background would be transformed into a positive value, and potentially interpreted as a "positive" SQR signal.

The following "Validity" analysis can be performed. The Raman value of the background sample ("Negative Control")

at a wave number, for example, 3260 cm$^{-1}$ should run as expected (above a minimum and below a maximum value). This determination will aid in ensuring that a correct sample was run as the negative control, and that the assay was run correctly. The SQR value of the positive control should not run below an expected value. This will aid in ensuring that a correct sample was run as the positive control, and that the assay was run correctly. The "Sum of the Differences" for each test sample should not run below an expected value. These analyses help to ensure that the sample spectrum is not consistently running below (less than) that of the negative control. The expected minimum and maximum values can be determined empirically by establishing minima and maxima from values obtained in repeated experiments.

The SQR method can be carried out manually or with the aid of a computer. One embodiment of the disclosure is a computer bearing machine operable language for the calculation of the SQR.

Instrumentation

It is also envisioned that embodiments of the present disclosure can be implemented on a micro-fluidic channel (or well) integrated circuit using micro or nano-fabrication technology in which the binding partner is immobilized in one or more micro-fluidic channels in a custom integrated circuitry which would also include the laser(s) and detectors for Raman spectroscopy. Such an implementation could detect single biological components such as pathological bacteria, proteins or genetic material.

Thus an object of certain embodiments of the present disclosure is to have a system for the detection of target biological organisms of components that utilizes a combination of chemical interactions including binding with a final step of Raman light scattering.

Another object of certain embodiments of the present disclosure is to have a system for the detection of target inorganic or organic components that utilizes a combination of chemical interactions including binding with a final step of Raman light scattering.

Another object of certain embodiments of the present disclosure is to combine an immunoassay with detection using Raman light scattering.

Still another object of certain embodiments of the present disclosure is to increase sensitivity of detection by the use of chemical reactants that produce resonance Raman light scattering.

Yet another object of certain embodiments of the present disclosure is to have an integrated circuit design with microfluidic channels or wells which can perform the combination of binding and Raman light scattering measurements.

These and other objects and advantages of the present disclosure will become obvious to a person of ordinary skill in this art upon reading of this disclosure including the associated drawings.

FIG. 1 is a flow chart of a typical prior art immunoassay technique (ELISA) (10) for the detection of biological organisms or components. The process begins by step (11) of preparing the liquid sample that includes the target biologic. For example, the sample can be prepared by pre-enrichment in a growth medium such as half-Frasier's broth or other suitable microbial growth medium. Alternately, a liquid sample for testing may be obtained from any liquid source. Solid material may be immersed in an appropriate liquid solution and potential target organism or molecules placed in solution and then sampled in the liquid. In the next step (12) the prepared liquid sample is combined (or mixed) with a binding partner that has been attached to a solid surface. Typical binding partners include antibodies, bacteriophage, and bacteriophage proteins. For example plastic microtiter plates, latex beads or magnetic microparticles may be used. Other solid supports such as nitrocellulose, filter paper, nylon and other plastics may also be used. The antibody/biologic combination is then incubated in step (13) to allow time for the biologic and antibody to bind together. Once this has occurred the combined binding partner/biologic is decanted (poured off) and washed to remove unbound biologics and other unwanted materials. New reactants are added in step (15) to enhance the sensitivity of the mixture to detection of signal molecules by various methods. Examples of such reactants include those listed in Table 3.

TABLE 3

Sensitivity Enhancing Reagents 1. binding partners labeled with radioactive molecules
2. binding partners labeled with fluorescent molecules
3. enzyme/binding partner conjugates combined with additional chemical reactants that react to form light absorbing molecules
4. enzyme/binding partner conjugates combined with additional chemical reactants that react to form light producing molecules
5. enzyme/binding partner conjugates combined with additional chemical reactants that react to form light reflecting molecules The mixture containing the bound binding partner/biologic and new reactants is the incubated in step (13) to allow time for the reaction to occur. At this point in many cases, the reaction part of the process (10) is complete and step (16) of measuring the molecules produced or included in steps (11) through (15) inclusive can be performed. If additional reactants are required, steps (14), (15) and (13) may be repeated one or more times in succession until the appropriate signal molecules are present.

The measurement of the signal molecule(s) provides a quantitative result that can then be analyzed and compared in step (17) to a known set of calibrated responses of known concentrations of the target biologic. This comparison results in step (18) which is the quantified result and associated report of the concentration of the target biologic in the sample prepared in step (11).

Although the descriptions of the process (10) of FIG. 1 have been associated with the detection of a biological organism or component, the process (10) is also applicable to the detection of many types of molecules to which antibodies or other binding partners can react.

Figure 2:
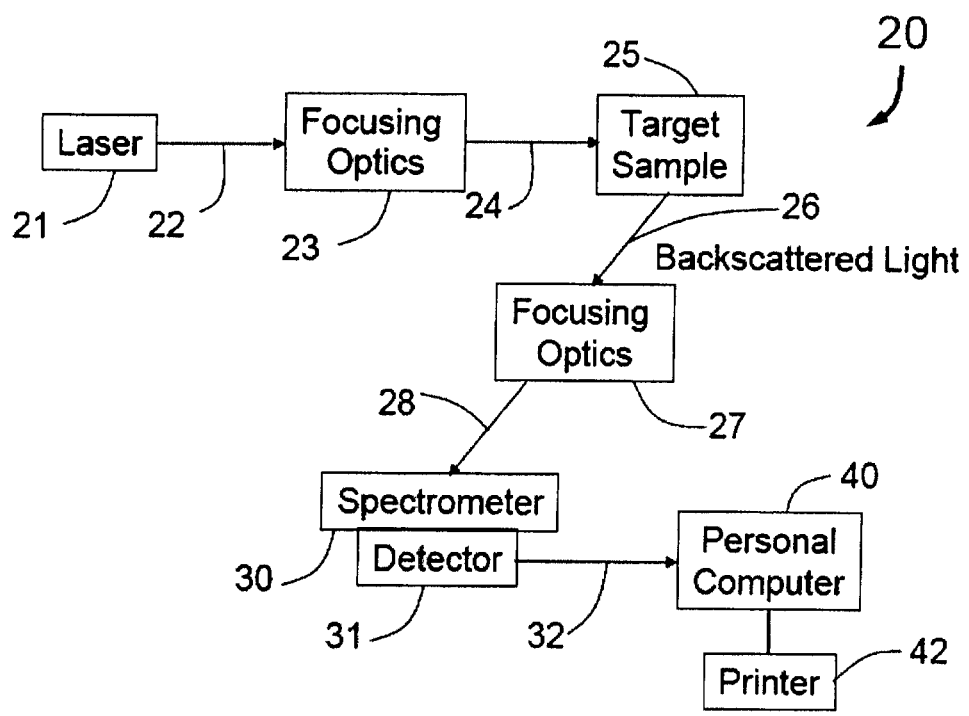
FIG. 2 is a diagram of an embodiment of the disclosed apparatus.

FIG. 2 is a diagram of an embodiment of the present disclosure detection sub-system (20). A laser (21) produces a laser beam (22) which is focused by the focusing optics (23) into a focused laser beam (24) which hits the target sample (25). The backscattered light (26) from the sample (25) is focused into the beam (28) by the focusing optics (27). The beam (28) is directed into the spectrometer (30) with detector (31). The output from the detector (31) is the signal (32) which is received by the personal computer (40) for analysis, storage and/or printing with the printer (42). The laser (21) is typically a continuous wavelength (CW) laser with output in the visible range. For example, an argon ion laser, helium neon laser, argon ion laser pumped tunable dye laser, or a diode laser in the green, red or other frequency. Focusing optics (23) and (27) include mirrors, lenses, irises, shutters, diffraction gratings, and/or polarizers. The target sample (25) may be liquid, gas or solid and in certain embodiments, the target sample would use a liquid or precipitated solid. The spectrometer (30) spatially separates the scattered light based on wavelength. An example of a usable spectrometer for the present disclosure is the Lambda Solutions model PS-1. The detector (31) measures the amplitude of the light spatially separated by the spectrometer (30) and converts this into an electrical signal (analog or digital). In certain embodiments, the detector would provide the electrical signal using a standardized computer interface such as RS-232, USB, parallel, IEEE 1394. An example of a usable detector (30) for the present disclosure is a Lambda Solutions PS-1. The personal computer (40) can be any desktop or laptop PC with an appropriate interface to the detector (31) and software designed to analyze, store and/or print the spectrum of the backscattered light (26) received by the spectrometer (30).

Figure 3:
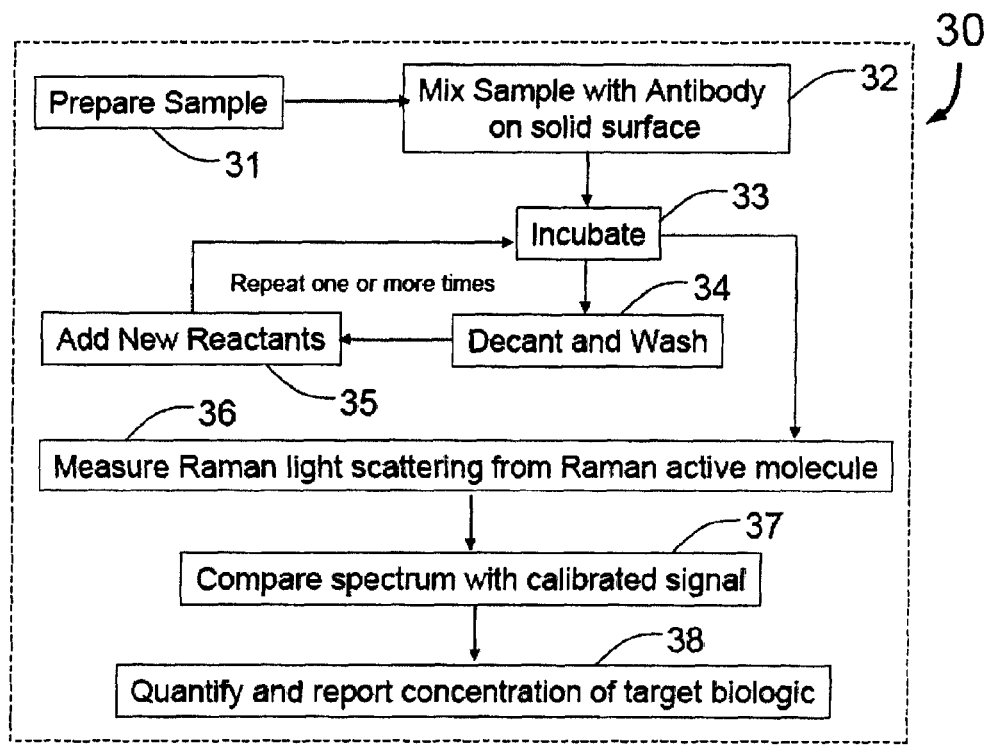
FIG. 3 is a flow chart of an embodiment of the disclosed technique for the detection of biological organisms and/or components.

FIG. 3 is a flow chart of an embodiment of the present disclosure (30) for the detection of biological organisms and/or components. The process begins by step (31) of preparing the liquid sample that includes the target biologic. For example, the sample may be prepared by pre-enrichment in a growth medium such as half-Frasier's broth or other suitable microbial growth medium. Alternately, a liquid sample for testing may be obtained from any liquid source. Solid material may be immersed in an appropriate liquid solution and potential target organism or molecules placed in solution and then sampled in the liquid. In the next step (32), the prepared liquid sample is combined (or mixed) with an antibody that has been attached to a solid surface. For example, plastic microtiter plates, latex beads or magnetic microparticles may be used. The antibody/biologic combination is then incubated in step (33) to allow time for the biologic and antibody to bind together. Once this has occurred the combined antibody/biologic is decanted (poured off) and washed to remove unbound biologics and other unwanted materials. New reactants are added in step (35) to enhance the sensitivity of the mixture to detection by Raman light scattering. Examples of such reactants are listed in Table 1.

The mixture containing the bound antibody/biologic and new reactants is the incubated in step (33) to allow time for the reaction to occur. At this point in many cases, the reaction part of the process (30) is complete and step (36) of measuring Raman light scattering from Raman-active molecules produced by steps (31) through (35) inclusive can be performed. If additional reactants are required, steps (34), (35) and (33) may be repeated one or more times in succession until the appropriate Raman-active molecules are present.

The measurement of Raman light scattering is a spectrum that can then be analyzed and compared in step (37) to a known set of calibrated responses of known concentrations of the target biologic. This comparison results in step (38) which is the quantified result and associated report of the concentration of the target biologic in the sample prepared in step (31).

*Listeria* may be measured in an (enzyme-linked immunosorbant assay) ELISA format. 100 microliters of various concentrations of bacteria; 100,000, 50,000, 25,000, 12,500, 6,250 and 0 colony forming units (cfu) per ml are added to microwells coated with anti-*Listeria* antibodies. After an incubation period between 30 and 60 minutes at 37° C., the wells are decanted and washed with a mild detergent solution three times. 100 µl of peroxidase-conjugated anti-*Listeria* antibodies are added to the well and incubated for 1 to 4 hours at 37° C. The wells are decanted and washed with a mild detergent solution three times. A mixture of 4-hydroxyl benzyl alcohol (80.6 mM), 4-aminoantipyrene (24 mM), Urea-Hydrogen Peroxide (10.6 mM) in 125 mM MES buffer (pH 6.0) is added and color is allowed to develop for 30-60 minutes. Raman Spectra of developed color from each well are developed and responses quantified.

Although the descriptions of the process (30) of FIG. 3 have been associated with the detection of a biological organism or component, the process (30) is also applicable to the detection of inorganic or organic molecules, contaminants or toxins.

Figure 4:
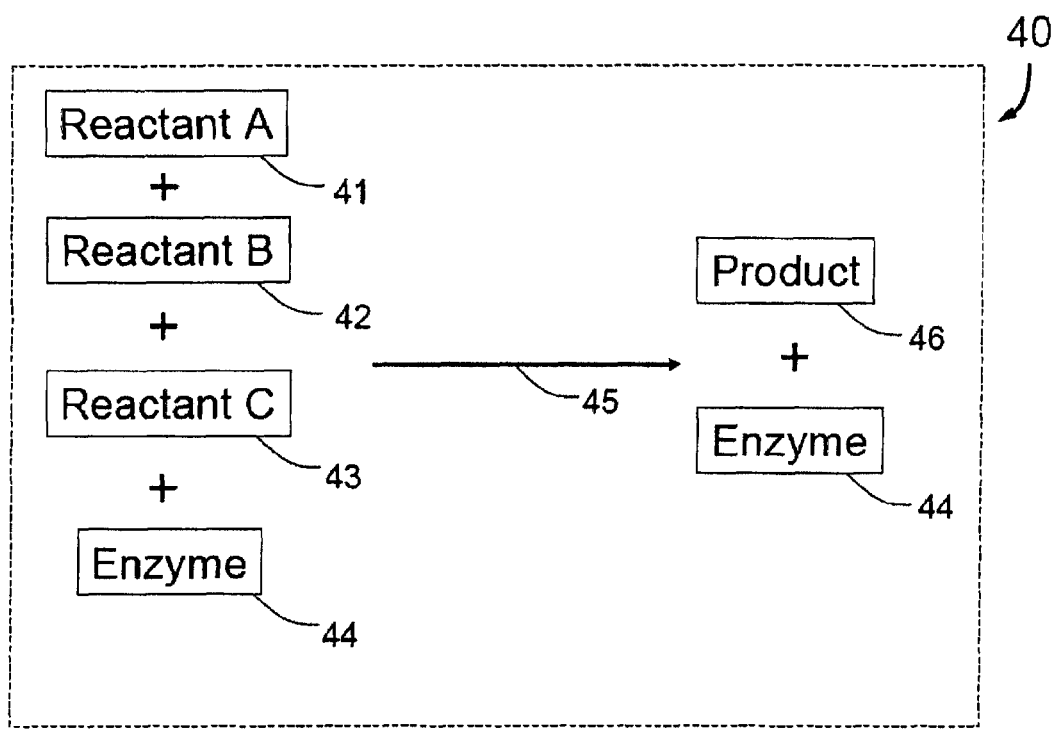
FIG. 4 is a block diagram of the enzyme system for converting chemical components to a Raman-active compound.

FIG. 4 is a block diagram for a chemical conversion system (40) which uses an enzyme for converting chemical components to a Raman-active compound. For example, one or more reactants designated (41), (42) and (43) are mixed with a biological catalyst (44). The biological catalyst (44) may be an enzyme specific for metabolizing the reactants provided or RNA structures designed to interact with the one or more reactants (41), (42), and (43). A conversion or combination of the reactants occurs in the reaction (45) and a measurable product (46) is formed. For example, the reactants and those in Table 4 are mixed together in the presence of peroxidase (44) and urea hydrogen peroxide (UP) (43).

TABLE 4

Reactants Producing Raman-active Products 2-hydroxybenzyl alcohol (HBA) (41)
5-aminosalicyclic acid (ASA) (42)
4-chloro-3,5-dimethylphenol (CDMP) (41)
5-aminosalicyclic acid (ASA) (42)
2-naphthol (NAP) (41)
5-aminosalicyclic acid (ASA) (42)
4-hydroxy-4-biphenyl-carboxylic acid (HBCA) (41)
5-aminosalicyclic acid (ASA) (42)
5,7 dichloro-8-hydroxyquinoline (DHQ) (41)
5-aminosalicyclic acid (ASA) (42)
4-chloro-1-naphthol (41)
4-aminoantipyrene (42)
phenol (41)
4-aminoantipyrene (42)

When mixed together, these components will yield an iminoquinone compound which is detectable using Raman spectroscopy. A reaction using HBA, ASA and UP is referred to as BASH-UP.

Additional reactants that may produce Raman-active products can be used in the disclosed methods, such as compounds comprising a least one hydroxyl group and one amino group at positions 1 and 4 in a benzene or naphthalene. Inclusion of additional groups such as carboxyl, amine, chlorine, bromine, nitro and other functional groups may enhance the Raman signal. Such compounds include:

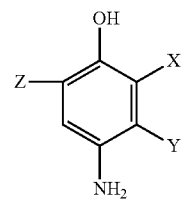

wherein X is chosen from H, $NH_2$, Cl, Br, nitro, and benzyl, Y is chosen from H, Cl, Br, and nitro, and Z is chosen from H, benzyl, and $NH_2$. In one embodiment, X is $NH_2$, and Y and Z are H. In another embodiment, X is Cl, and Y and Z are H. In another embodiment, X is Br, and Y and Z are H. In another embodiment, X is nitro, and Y and Z are H. In another embodiment, X and Z are H and Y is Cl. In another embodiment, X and Z are H and Y is Br. In another embodiment, X and Z are H and Y is nitro. In another embodiment, X and Z are benzyl and Y is H. In another embodiment, X and Z are $NH_2$ and Y is H.

Such compounds also include:

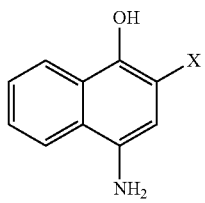

wherein X is chosen from H, OH, Cl, Br, and nitro.
Such compounds also include:

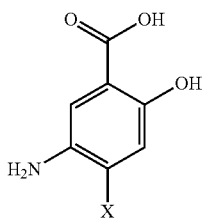

wherein X is chosen from H, Cl, Br, and nitro.

Additional compounds that may produce Raman-active products in the disclosed methods include compounds comprising at least two hydroxyl functions in 1, 2 or 1, 4 positions in a benzene or naphthalene ring.

Such compounds include:

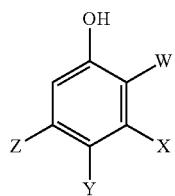

wherein W, X, Y, and Z are chosen from H and OH. In one embodiment, Y is OH and X, Y and Z are H. In another embodiment, W is OH, and X, Y and Z are H. In another embodiment, W and X are OH, and Y and Z are H. In another embodiment, W and Y are OH, and X and Z are H. In another embodiment, W and Z are OH and X and Y are H.

Such compounds include polyphenols, such as:

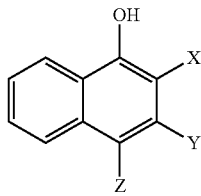

wherein X, Y and Z are chosen from H and OH. In one embodiment, X is OH and Y and Z are H. In another embodiment, X and Y are OH and Z is H. In another embodiment X and Z are OH and Y is H. In another embodiment, Z is OH and X and Y are H.

Additional compounds that may produce Raman-active products in the disclosed methods include compounds comprising hydroxymethlene (—$CH_2OH$) group in a benzene or naphthalene. Inclusion of additional hydroxyl groups at positions 1, 4, and 6 may enhance the Raman signal.

Such compounds include:

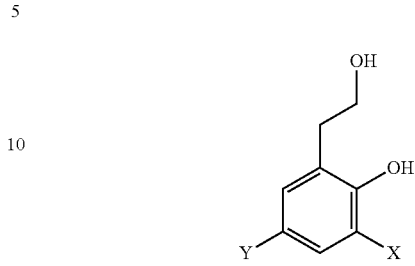

wherein X and Y are chosen from H and OH. In one embodiment X is OH and Y is H. In another embodiment, X is H and Y is OH.

Such compounds also include:

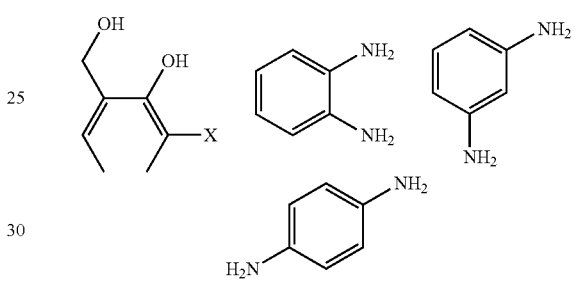

wherein X and Y are chosen from H and OH. In one embodiment, X is OH and Y is H. In another embodiment, X is H and Y is OH.

Such compounds also include aromatic amines, including compounds comprising ortho-phenylenediamine, meta-phenylenediamine, and para-phenyleneamine:

Such compounds also include 2,4-diaminobenzyl alcohol, 2-amino-1-naphthol, and 4-aminoantipyrene.

The product of the reaction (45) may be used as a quantitative or qualitative reporting molecule for the reaction and as such may be used as a probe for the presence of specific biological targets if conjoined with, for example, specific antibodies or biological or chemical binding partners.

Figure 5:
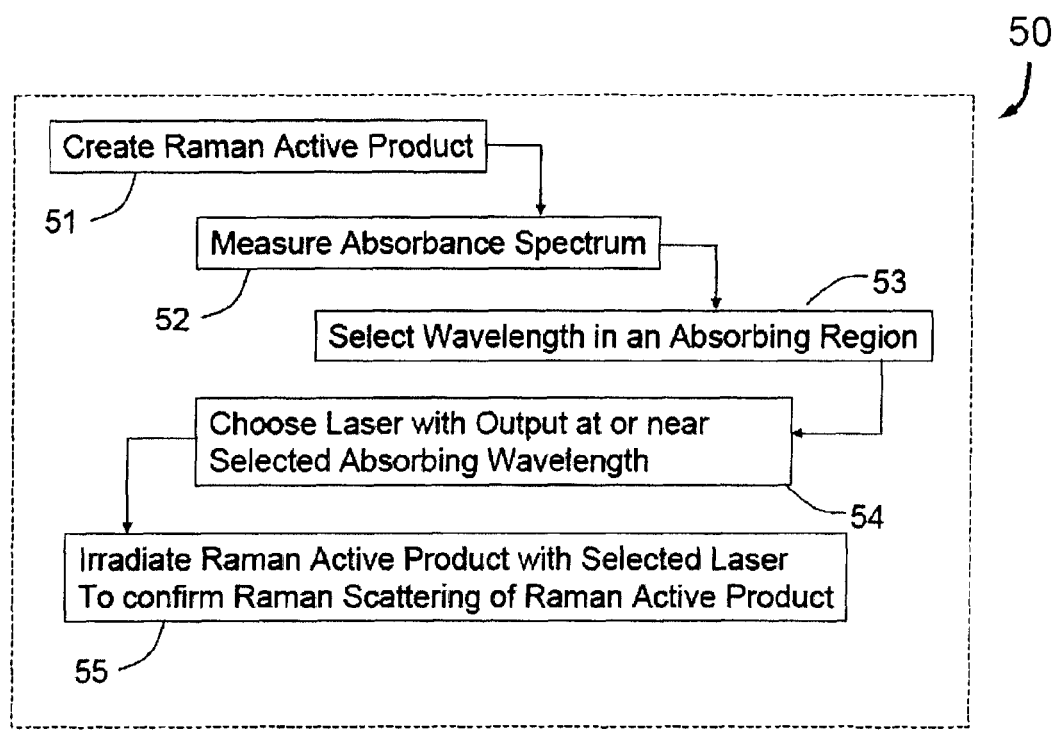
FIG. 5 is a flow chart of a technique for choosing laser light frequencies to excite specific target molecules.

FIG. 5 is a flow chart of the technique (50) for choosing one or more laser light frequencies to excite specific target molecules for resonance Raman detection. A Raman-active product (51), such as the product (46) produced by the reaction (45) of FIG. 4, is a chemical that possesses a structure which is Raman-active. The absorbance spectrum of the product (51), is measured in step (52) using a technique such as absorbance or transmittance spectrophotometry. In step (53), one or more wavelengths are identified at which the product (51) absorbs light as seen in the spectrum measured in step (52). In step (54), a laser that emits light at a wavelength corresponding to one of the one or more wavelengths identified in step (53) is then selected. Such laser wavelengths can be in the visible range, ultra-violet range or infra-red range. For example, for the *Listeria* detection reaction (30) described for FIG. 3, the laser wavelength selected is 532 nm.

Finally, in step (55) the laser chosen in step (54) is used to irradiate the Raman-active product created in step (51). This will confirm that there is significant Raman scattering of the Raman-active product created in step (51) to provide adequate signal for detection.

Figure 6:
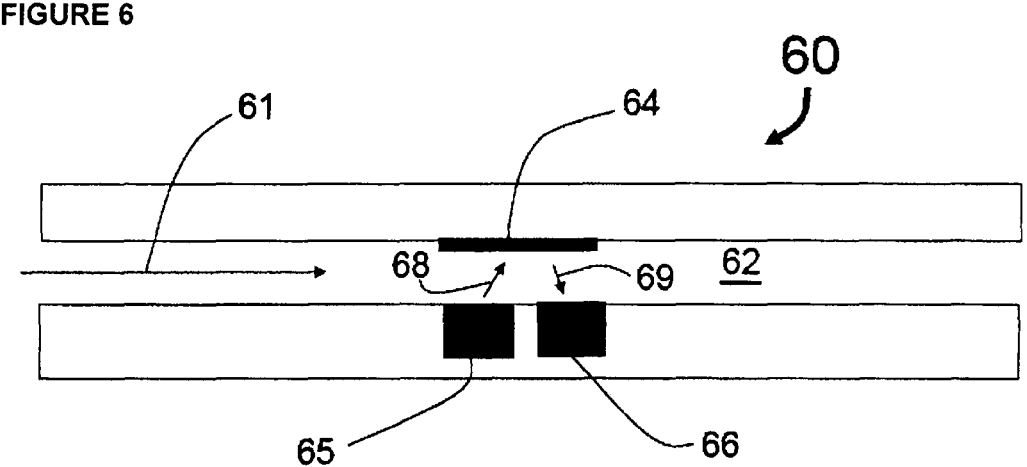
FIG. 6 is an illustration of a micro-fluidic channel designed to detect Raman-active compounds.

FIG. 6 is an illustration of a micro-fluidic channel (60) designed to detect Raman-active compounds. A source liquid (or gas) sample (61) including the target biological organisms or components flows through the channel (62). The target biological organisms or components will react and be bound to the reactant(s) attached to the active surface (64). Light (68) from the laser (65) produces Raman scattered light (69) which is detected by the photodetector (66). The photodetector is designed to measure one or more specific wavelengths which correspond to the Raman spectrum of the combined reactant(s) and biological organism or component. It is also envisioned that instead of binding the biological organism or component to the surface (64), the reactant(s) may be released from the surface and the Raman-scattering laser (65) and detector (66) may be located downstream from the surface.

Figure 7:
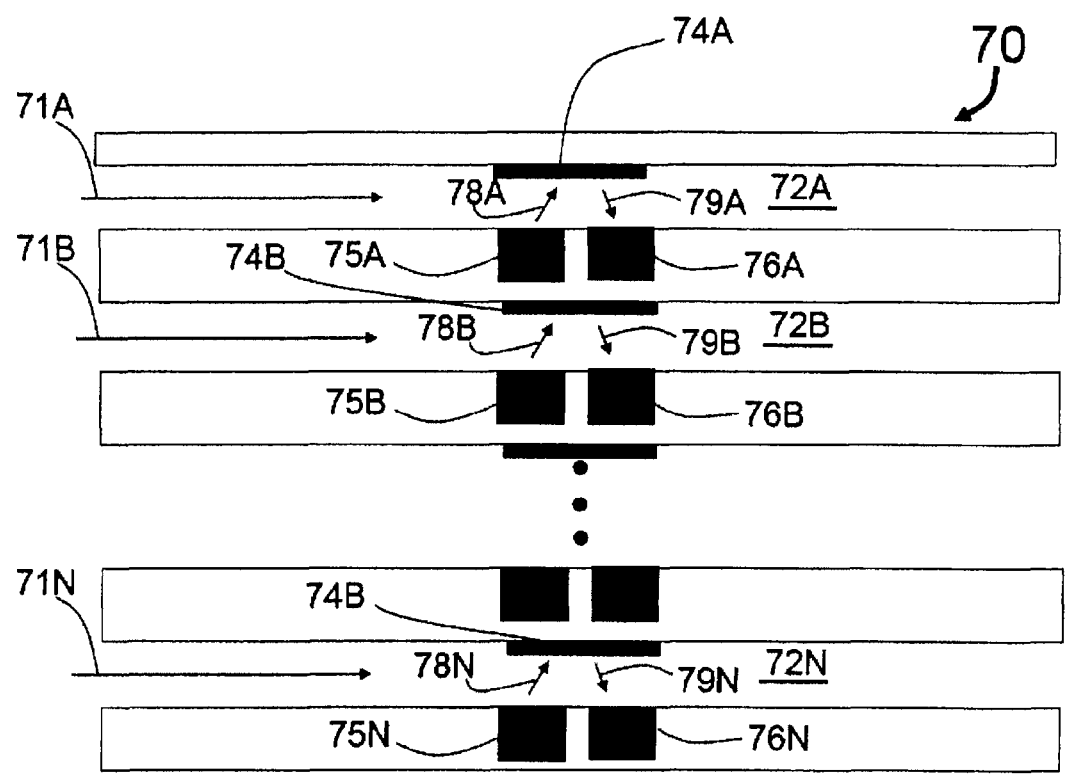
FIG. 7 is an illustration of an array of micro-fluidic channels such as might be incorporated into a custom integrated circuit.

FIG. 7 is an illustration of an array of micro-fluidic channels (70) designed to detect Raman-active compounds. One or more source liquid (or gas) samples (71A), (71B) through (71N) which include the target biological organisms or components flow through the channels (72A), (72B) through (72N). The target biological organisms or components will react and be bound to the reactant(s) attached to the active surfaces (74A), (74B) through (74N). Light, (78A) through (78N), from the lasers, (75A) through (75N), produce Raman-scattered light, (79A) through (79N), which is detected by the photodetectors (76A) through (76N). The photodetectors are designed to measure one or more specific wavelengths which correspond to the Raman spectrum of the combined reactant(s) and biological organisms or components bound to the surfaces.

The number of micro-fluidic channels in the array of micro-fluidic channels as limited by the upperbound N, ranges from 2 to 100,000. It is also envisioned that a multiplicity of different reactants and laser wavelengths may be used in different channels. This would allow detection of multiple wavelengths of scattering from the same biological organism or component or it would allow the simultaneous detection of multiple different biological organisms and components. Finally instead of an array of micro-fluidic channels (70), it is envisioned that an array of micro-fluidic wells could be used to produce a 2-dimensional array of Raman-scattering detectors.

The present disclosure is more particularly described in the following examples that are intended as illustrative only since numerous modifications and variations therein will be apparent to those skilled in the art. Various embodiments are now described in detail. As used in the description and throughout the claims that follow, the meaning of "a", "an", and "the" includes plural reference unless the context clearly dictates otherwise. Also, as used in the description and throughout the claims that follow, the meaning of "in" includes "in" and "on" unless the context clearly dictates otherwise. All references cited and discussed in this specification are incorporated herein by reference in their entireties and to the same extent as if each reference was individually incorporated by reference.

EXAMPLES

Example 1

Detection of *Listeria* Using Bash-Up

Figure 8:
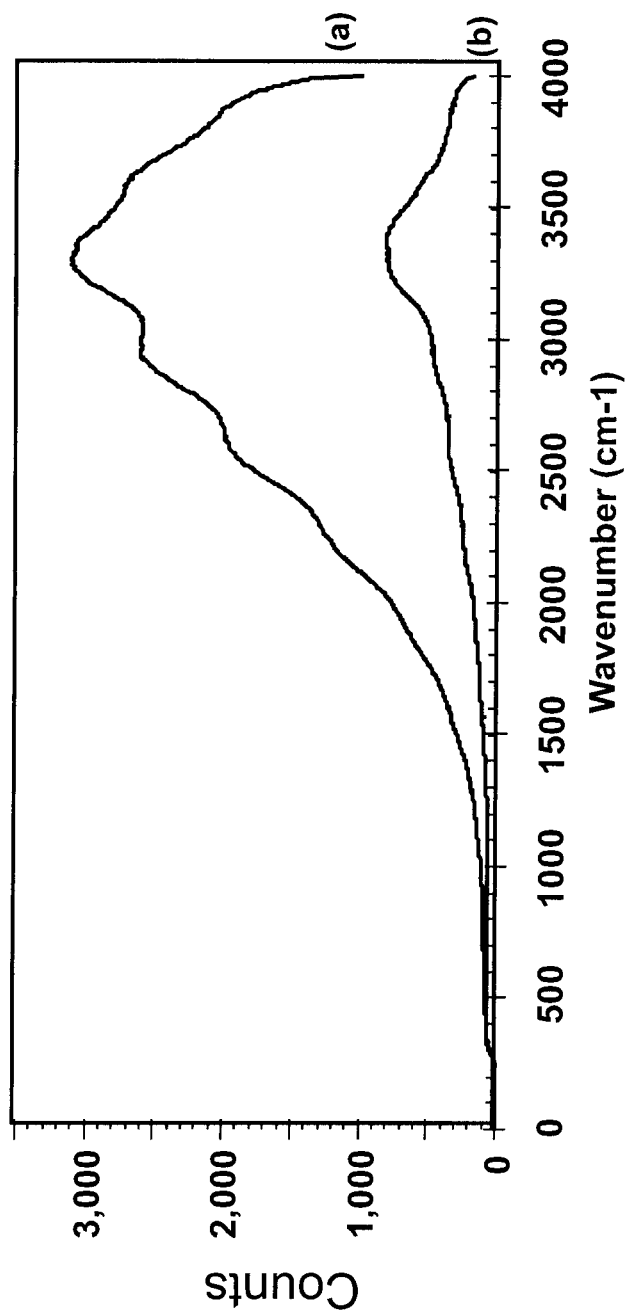
FIG. 8 plots Raman spectra from an enzyme-linked immunoassay for a pathogenic bacteria, Listeria, utilizing an antibody linked to peroxidase and with shift numbers (cm-1) plotted on the abscissa and signal magnitudes plotted on the ordinate (arbitrary units) for a sample containing Listeria (a) and a sample not containing Listeria (b).

FIG. 8 depicts Raman spectra obtained from an enzyme-linked immunoassay for the pathogenic bacteria *Listeria* utilizing the two-component BASH-UP chemistry, an enzyme-linked antibody, and Raman detection procedure described below utilizing the following buffers and reagents:

Working Saline Buffer (Used for Washes in Protocol):
10 mM Sodium Phosphate, pH 6.0
137 mM Sodium Chloride
2.67 mM Potassium Chloride
0.09 mM Ethylenediaminetetraacetic acid (EDTA)
0.05% Bronidox-L
Final Chemistry Reagent (Bash):
0.588 mM 5-Aminosalicylic Acid
0.145 mM 2-Hydroxybenzyl alcohol
0.005 mM L-Ascorbic Acid
0.09% Tween-20
UP Component:
1.063 mM Urea Peroxide
Working Saline Buffer
Additional Reagents:
1. Microparticles—Anti-*Listeria* (antibody) coated magnetic microparticles at 2 million microparticles/sample upon addition.
2. Conjugate Solution—Anti-*Listeria* (antibody) conjugated with Horseradish Peroxidase (HRPO) at 2 µg/sample upon addition Samples of either heat-killed *Listeria* or a negative broth (1 ml) were subject to the following procedure. Note, the 1 ml sample may be from culture, control, swab, sponge, etc.

Procedure:
1. Add 100 µl of microparticles to sample.
2. Incubate 30 minutes at room temperature.
3. Capture microparticles with magnet 10 minutes.
4. Remove sample volume.
5. Add 500 µl Working Saline Buffer, mix 2 minutes at 1000 rpm.
6. Capture microparticles with magnet 2 minutes.
7. Remove wash volume.
8. Repeat steps 3-7 two more times for a total of 3 washes.
9. Add 200 µl Conjugate Solution.
10. Mix solution for 30 minutes.
11. Repeat wash steps 3-7 for a total of 3 washes.
12. Add 200 µl Final Chemistry Reagent.
13. Incubate 20 minutes with mixing at 1000 rpm.
14. Add 40 µl 0.5 N NaOH.
15. Mix 2 minutes at 1000 rpm.
16. Capture microparticles with magnet 2 minutes.
17. Transfer volume to cuvette for Raman signal detection.

In this procedure, the Final Chemistry Reagent was a two component BASH-UP chemistry. The Raman signal was generally stable for ~1 hour or longer. The first component in the chemistry (BASH) contained 2-hydroxy benzyl alcohol (0.02 mg/ml), 5-amino salicylic acid (0.1 mg/ml), 0.1% Tween-20, and ascorbic acid (1 µg/ml) in the Working Saline Buffer (pH 6.0). The second component (UP) contained urea peroxide adduct (1 mg/ml) the working Saline Buffer (pH 6.0) including EDTA (1 mM). These formulations maintained activity when refrigerated out of direct light for more than one month. Mixing the two components at a ratio of 1 UP to 10 BASH created a working solution of BASH-UP that was generally stable for one working day.

An aliquot of BASH-UP was added to samples containing either heat-killed *Listeria* or a negative broth and allowed to react for 30 minutes. The appropriate period of time will vary based on the sensitivity of detection required. 40 µl of 0.5 N NaOH was added to the 200 µl BASH-UP reaction volume to stop the reaction and render the products Raman-detectible. Alteration of the volume and concentration of the NaOH may afford greater signal stability as required by the particular assay.

Raman scattering was observed from the 240 μl sample using a Raman Systems R-3000 Raman spectrometer with a 532 nm laser operated at the high power setting.

Example 2

Colorimetric Assays of Horseradish Peroxidase (HRPO)

Colorimetric assays of Horseradish Peroxidase (HRPO) activity were conducted to obtain data that could be compared with the Raman-based methods. TMB develops a deep blue soluble product when reacted with horseradish peroxidase. ABTS develops a blue-green product when reacted with horseradish peroxidase.

Colorimetric assays were performed with the TMB and ABTS reactions using two different methods:

Method A (TMB):

HRPO dilutions were made to measure 1000 pg to 0.0125 pg per 50 μl sample in phosphate-buffered saline (PBS) containing 0.1% bovine serum albumin (BSA) at pH 7.4. 50 μl HRPO sample per dilution was added to 200 μl TMB reagent and allowed to react for 15 or 30 minutes at which time 200 μl stop-solution (KPL Laboratories) was added. Absorbance was measured at 450 nm for each sample.

Method B (ABTS):

HRPO dilutions were made to allow 1000 pg to 0.0125 pg per 50 μl sample in PBS at pH 7.4. 50 μl HRPO sample per dilution was added to 200 μl ABTS reagent and allowed to react for 15 or 30 minutes at which time 200 μl stop solution (1% SDS in water) was added. Absorbance was measured at 405 nm for each sample.

The limit of detection of HRPO for TMB was 8 pg/ml and the dynamic range was 5 to 5000 pg/ml. For ABTS, the limit of detection was 32 pg/ml and the dynamic range was 32 to 5000 pg/ml.

Example 3

Fluorogenic and Chemiluminescent Assays of HRPO

Several reagents were tested: Sigma Chemiluminescent Peroxidase Substrate, Pierce Fluorogenic (Chemifluorescent) Substrate Kit, AnaSpec Sensolyte ADHP Fluorogenic Substrate, Invitrogen Molecular Probes Amplex Red Fluorogenic Substrate, and KPL Laboratories LumiGLO. Sigma and Pierce substrates did not work with HRPO in PBS or with BSA-containing buffer.

A. AnaSpec Fluorogenic ADHP Assay

AnaSpec Fluorogenic kit utilizes ADHP (10-acetyl-3,7-dihydroxyphenoxazine) to analyze peroxidase in solution whereby ADHP is oxidized in the presence of peroxidase and hydrogen peroxide. The oxidized product of ADHP (resozufin) gives pink fluorescence that can be measured at the emission wavelength of 590 nm with the excitation wavelength of 530-560 nm. An overdose of peroxidase in the assay will further convert the fluorescent resorufin to non-fluorescent resozurin to yield reduced fluorescent signal. HRPO dilutions were made to allow detection of 1,000,000 pg to 0.0625 pg per 50 μl sample were prepared in PBS at pH 7.4. The procedure was the same as described earlier for TMB and ABTS assays, and two methods were used.

Method A:

ADHP Reagent and Hydrogen Peroxide were prepared per manufacturer's instructions. 500 μl of peroxidase solution was added to 500 μl ADHP reagent in a 1.5 ml plastic microcuvette. The reaction mixture was gently mixed, and incubated at room temperature for 30 min without light exposure. The fluorescent signal was measured for emission at 590 nm with excitation at 550 nm on an Ocean Optics Fluorescent Spectrometer.

Method B:

Similar to Method A except 400 μl of each of peroxidase and ADHP reagents were used.

The sensitivity (lowest limit of detection) of the AnaSpec ADHP fluorescent assay was found to be 12.5 pg/ml of HRPO. The assay range was linear from 250 pg/ml to 0 pg/ml of HRPO.

B. Molecular Probes-Invitrogen Amplex Red Fluorogenic Assay

Molecular Probes Fluorogenic assay kit employs Amplex Red (10-acetyl-3,7-dihydroxyphenoxazine), which is similar to AnaSpec ADHP assay. The oxidized end product of the assay with peroxidase and hydrogen peroxide is resorufin. The assay claim is $1 \times 10^{-5}$ U/ml, equivalent to 10 pg/ml ($1 \times 10^{-5}$ ml).

HRPO dilutions made to allow detection of 1,000,000 pg to 0.0625 pg per 50 μl sample were prepared in PBS, pH 7.4. Amplex Red Reagent and Hydrogen Peroxide were prepared per Manufacturer's instructions. 400 μl of peroxidase solution was added to 400 μl ADHP reagent in a 1.5 ml plastic microcuvette. The reaction mixture was gently mixed and incubated at room temperature for 30 min in the dark. The fluorescent signal was measured at 590 nm with excitation at 550 nm on an Ocean Optics Fluorescent spectrometer at 30 min and 35 min.

The sensitivity (lowest limit of detection) of the Molecular Probes Amplex Red Fluorescent assay was found to be 25 pg/ml of HRPO. The assay range was linear from 250 pg/ml to 0 pg/ml of HRPO.

C. LumiGLO®

LumiGLO is a luminol-based chemiluminescent substrate designed for use with peroxidase-labeled reporter molecules. In the presence of hydrogen peroxide, HRPO converts luminol to an excited intermediate dianion. This dianion emits light on return to its ground state. After reaction with HRPO conjugate, the light emission from LumiGLO reaches maximum intensity within 5 minutes and is sustained for approximately 1-2 hours.

The sensitivity (lowest limit of detection) of the LumiGLO in representative experiments was found to be 11 pg/ml of HRPO.

Raman-Based Assays

A variety different combinations and amounts of reagents producing Raman-active products were tested to find the optimal reaction conditions for each. For these assays, 50 μl HRPO sample per dilution was added to 150 μl of the selected Raman Reagent (A-E), plus urea peroxidase in volume ratio of 9:1, and samples allowed to react for 30 minutes. Formulations of Reagents A-E are shown in the tables below. 50 μl of 0.5 N NaOH was then added to each sample which was allowed to incubate for 30 minutes. Raman-based assays were also performed in HRPO samples diluted in PBS at pH 7.4. Raman spectra were recorded with a Diagnostics Raman Systems INC QE 65000 Raman Detector. Spectral analyses were based on measurement of the Raman signal at wavelength 3260 $cm^{-1}$ and by SQR using every $2^{nd}$ wavenumber between 3500 $cm^{-1}$ and 4000 $cm^{-1}$.

Example 4

Raman Reagent A (Bash-Up)

The formulations used for this study are listed in Table 5:

TABLE 5

RAMAN REAGENT A

| Formula | Buffer | ASA µg/ml | HBA µg/ml | AA µg/ml |
|---|---|---|---|---|
| A-1 | PBS-EDTA, pH 6.0 | 100 | 20 | 20 |
| A-2 | PBS-EDTA, pH 6.0 | 500 | 20 | |
| A-3 | PBS-EDTA, pH 6.0 | 100 | 100 | |
| A-4 | PBS-EDTA, pH 6.0 | 300 | 20 | |
| A-UP | PBS-EDTA, pH 6.0 | 1000 | | |

Figure 9:
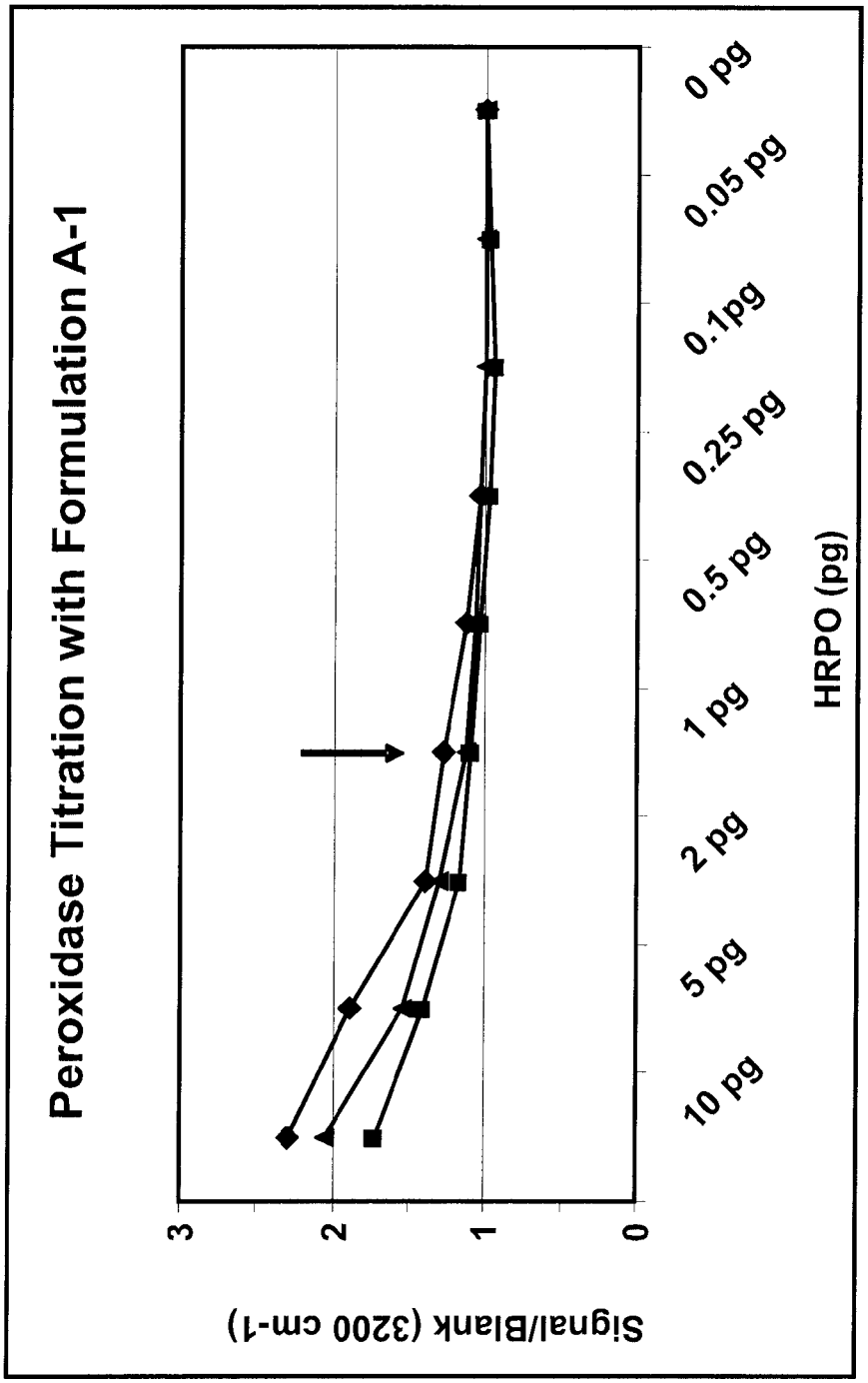
FIG. 9 A plots Raman spectra measured at 3260 $cm^{-1}$ produced using Raman Reagent formulation A-1 in three experiments, while FIG. 9 B plots SQR Raman spectra measured at 3500-4000 $cm^{-1}$ produced using Raman Reagent A-1 in the three experiments.
Figure 9:
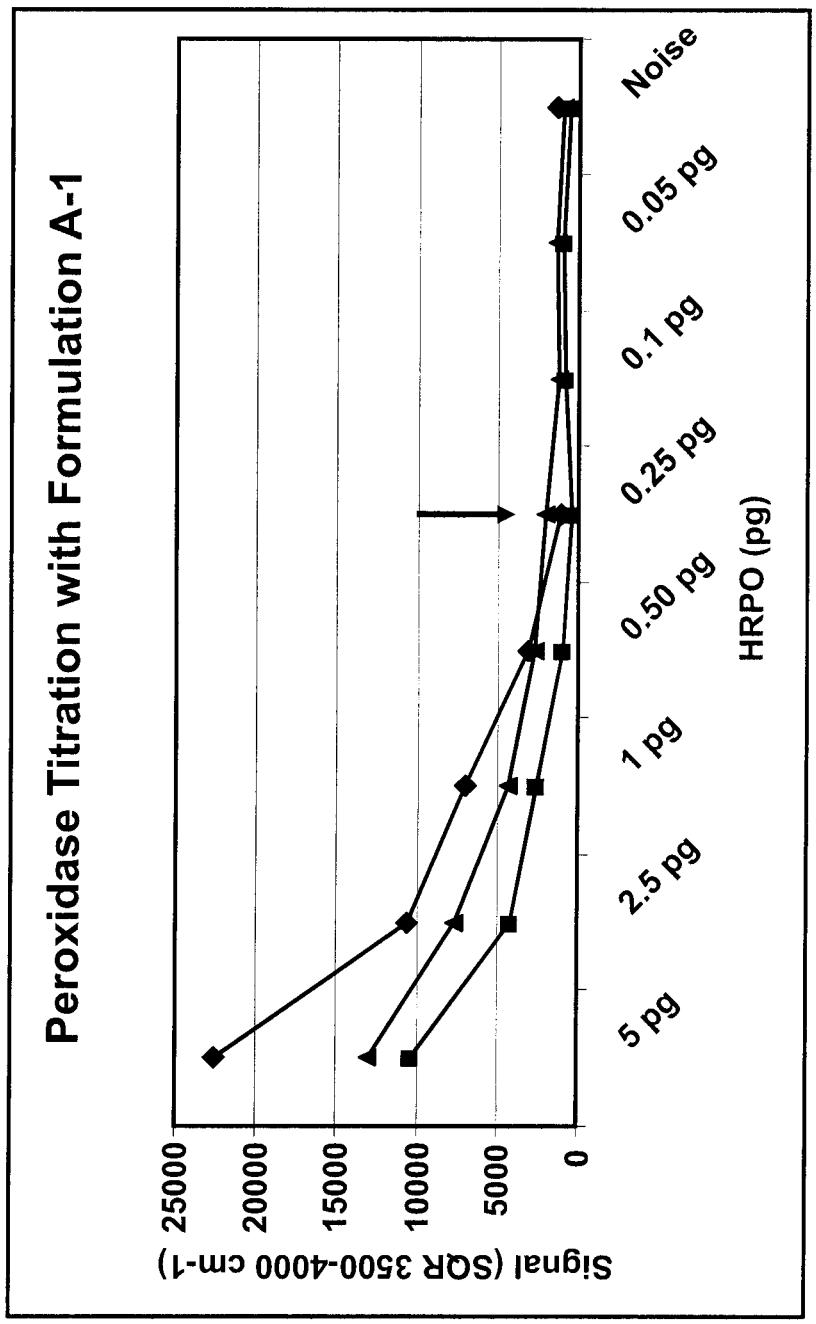

HRPO was reacted with Raman Reagent A-1 with dilution in PBS containing 0.1% BSA at pH 7.4. Raman spectra were recorded for HRPO dilutions from 0 ("blank") to 100 pg/ml. FIG. 9 A shows the single peak (3260 cm$^{-1}$) dependence on HRPO concentration and FIG. 9 B shows the same results after applying SQR analysis (3500-4000 cm$^{-1}$). Table 6 compares the detection limits of HRPO detection from different experiments, showing increased sensitivity from the SQR method compared to measurements based on a single peak.

TABLE 6

DETECTION LIMITS

| Formulation | Single peak | SQR | Increase in sensitivity |
|---|---|---|---|
| A-1 | 1.0 pg | 0.5 pg | 2 times |
| A-1 | 2.5 pg | 0.5 pg | 5 times |
| A-1 | 2.5 pg | 0.025 pg | 10 times |

Figure 10:
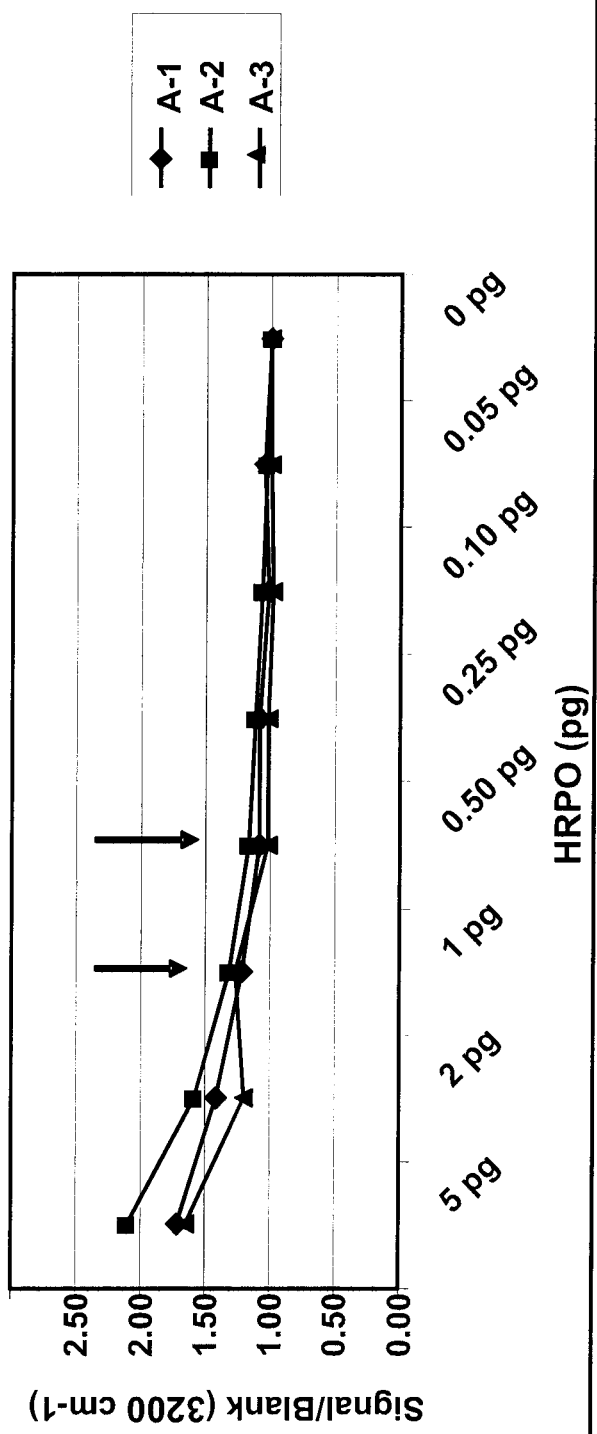
FIG. 10 plots Raman spectra measured at 3260 $cm^{-1}$ produced using Raman Reagent A-1 (diamonds), and Raman Reagent A-2 (triangles) and A-3 (squares).
Figure 11:
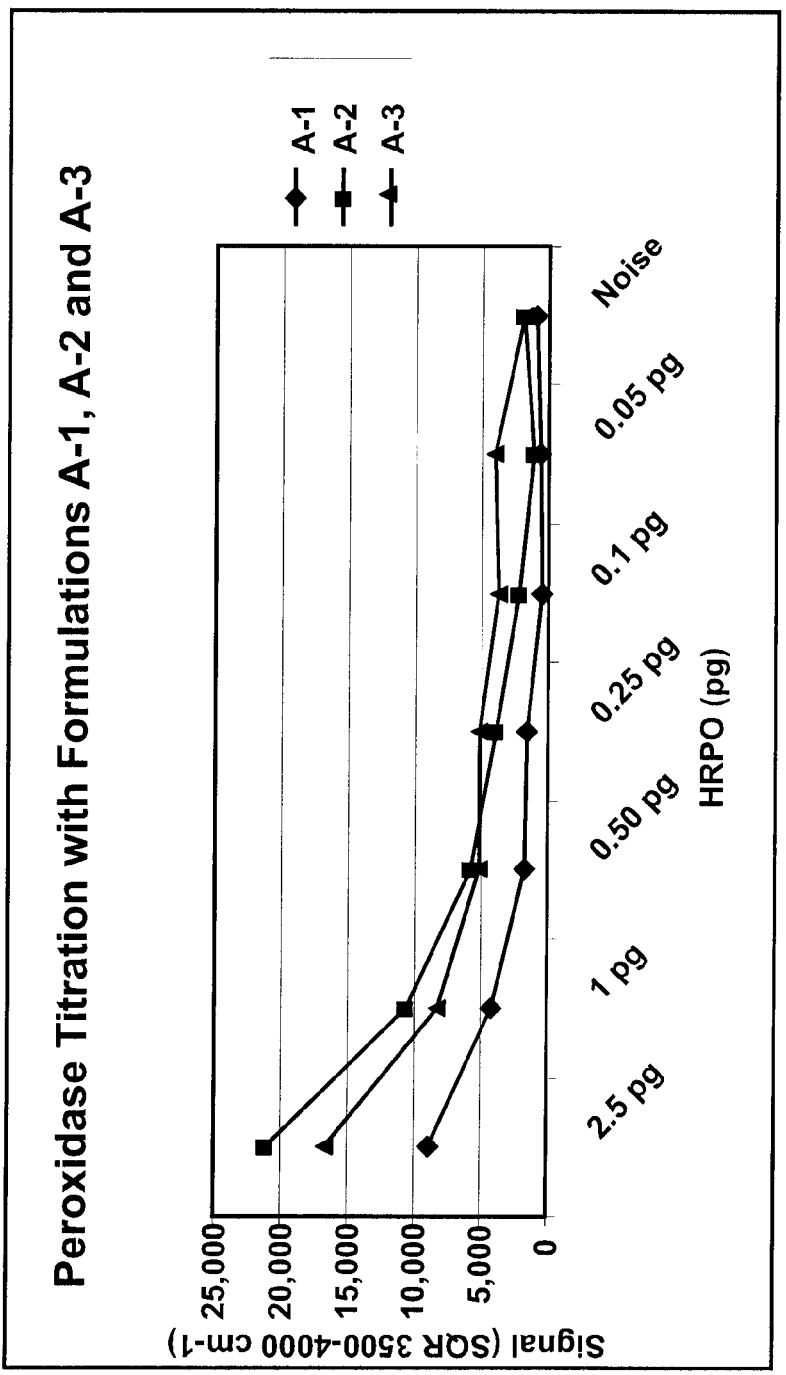
FIG. 11 plots SQR Raman spectra measured at 3500-4000 $cm^{-1}$ produced using Raman Reagent formulation A-1 (diamonds), and Raman Reagent A-2 (squares and triangles).

HRPO was reacted in Raman Reagents A-1, A-2, and A-3 and Raman spectra were recorded for HRPO dilutions from 0 ("blank") 5 pg/ml. FIG. 10 shows the single peak (3260 cm$^{-1}$) dependence on HRPO concentration. FIG. 11 shows an SQR analysis of Raman Reagents A-1 and A-2 (3500-4000 cm$^{-1}$).

Figure 12:
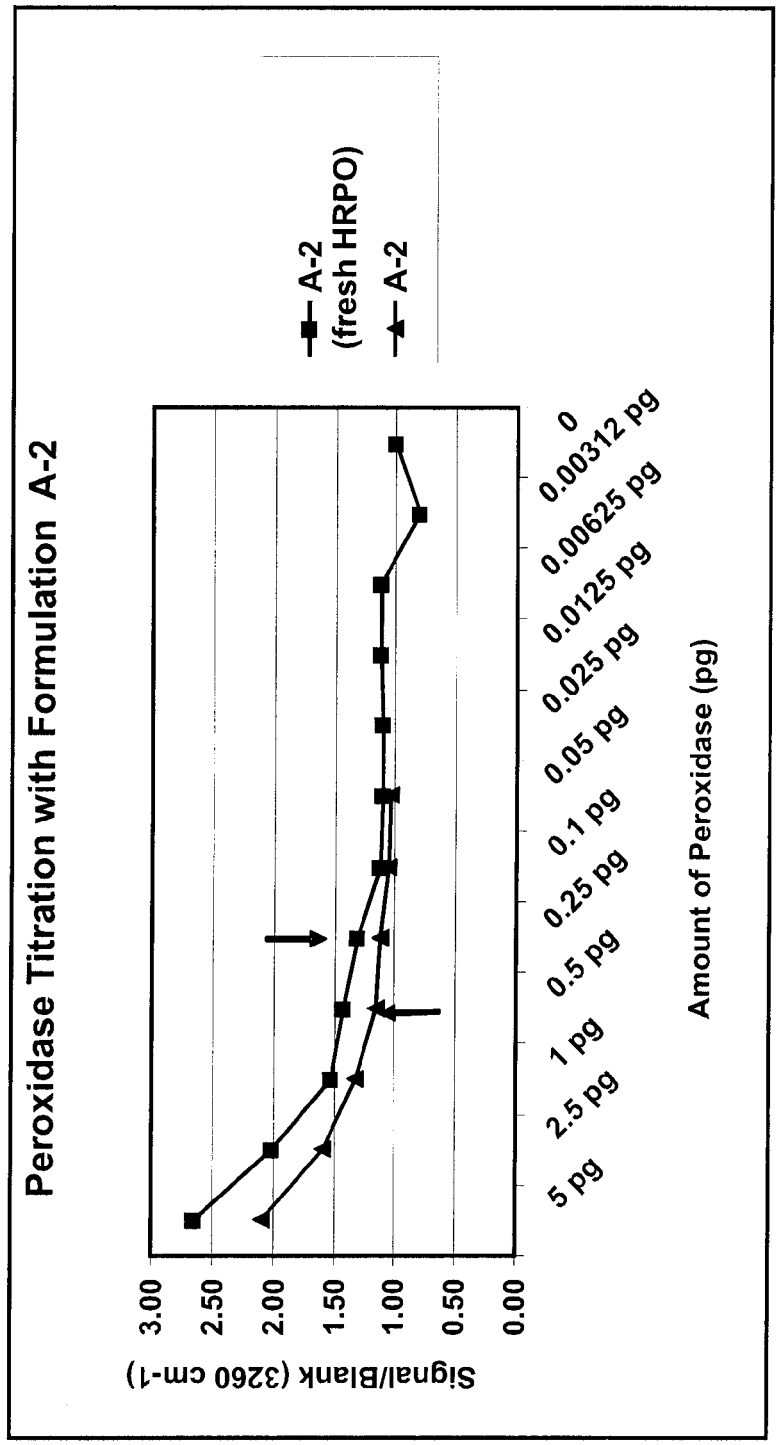
FIG. 12 plots Raman spectra measured at 3260 $cm^{-1}$ produced using Raman Reagent formulation A-2 (squares) and A-2 with fresh HPRO in BSA diluent (diamonds).

HRPO was reacted with Raman Reagent A-2, and with fresh HPRO in BSA diluent. FIG. 12 shows the single peak (3260 cm$^{-1}$) dependence on HRPO concentration.

Table 7 compares the detection limits from different Raman Reagent A formulations, showing the increase in sensitivity provided by the SQR method.

TABLE 7

DETECTION LIMITS

| Formulation | Single peak | SQR | Increase in sensitivity |
|---|---|---|---|
| A-1 | 1 pg | 0.5 pg | 2-4 times |
| A-2 | 0.5 pg | 0.05 pg | 10 times |
| A-2* | 0.25 pg | 0.00625 pg | 40 times |
| A-1** | 1 pg | 1 pg | No change |

*Fresh HRPO in BSA diluent
**A-1 lacking AA

Example 5

Raman Reagent B

Raman reagent formulations used for this study are listed in Table 8.

TABLE 8

RAMAN REAGENT B

| Formula | Buffer | ASA µg/ml | CDMP µg/ml |
|---|---|---|---|
| B-1 | PBS-EDTA, pH 6.0 | 100 | 50 |
| B-2 | PBS-EDTA, pH 6.0 | 500 | 25 |
| B-3 | PBS-EDTA, pH 6.0 | 250 | 25 |
| B-4 | PBS-EDTA, pH 6.0 | 100 | 25 |
| B-UP | PBS-EDTA, pH 6.0 | 1000 | |

Figure 13:
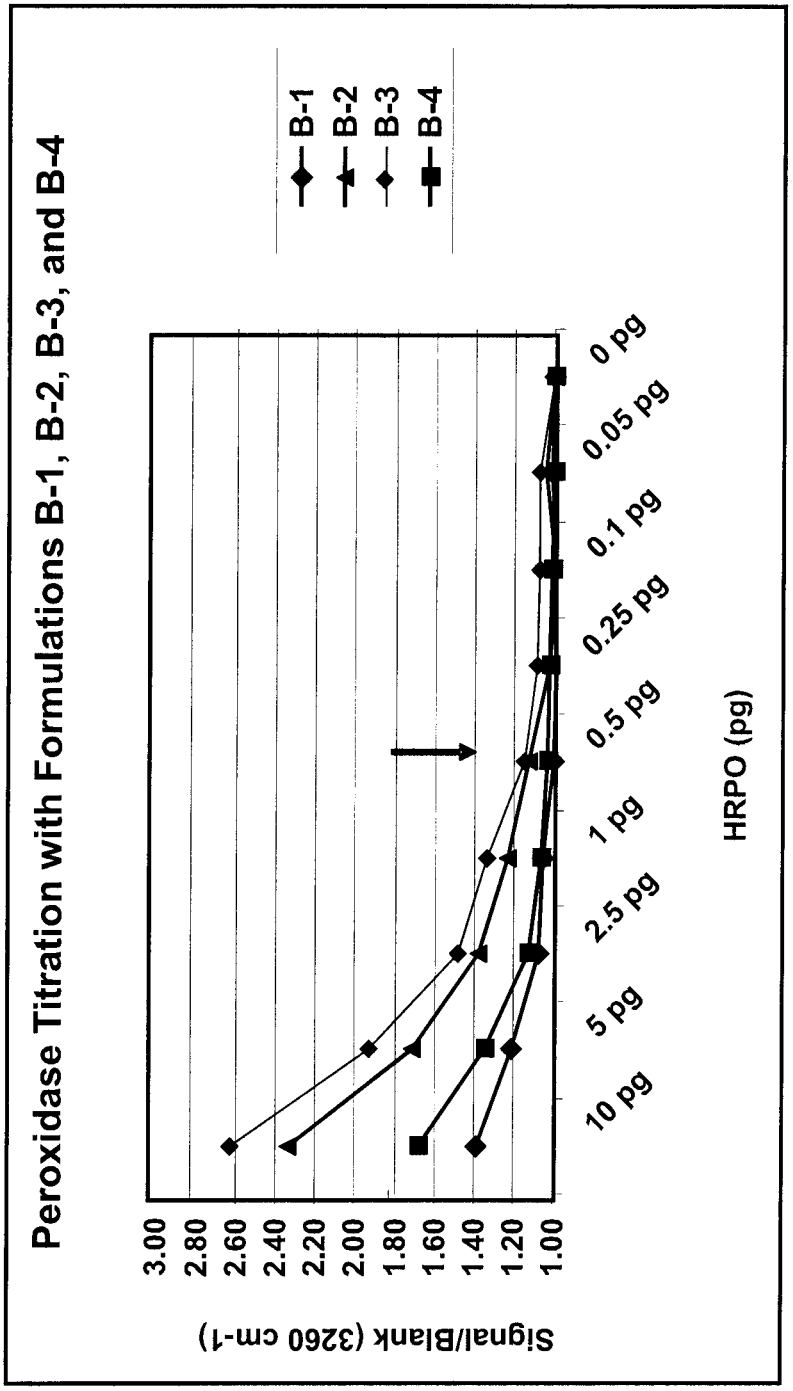
FIG. 13 plots Raman spectra measured at 3260 $cm^{-1}$ produced using Raman Reagent B-1 (diamonds), B-2 (squares), B-3 (triangles), and B-4 ("Xs").
Figure 14:
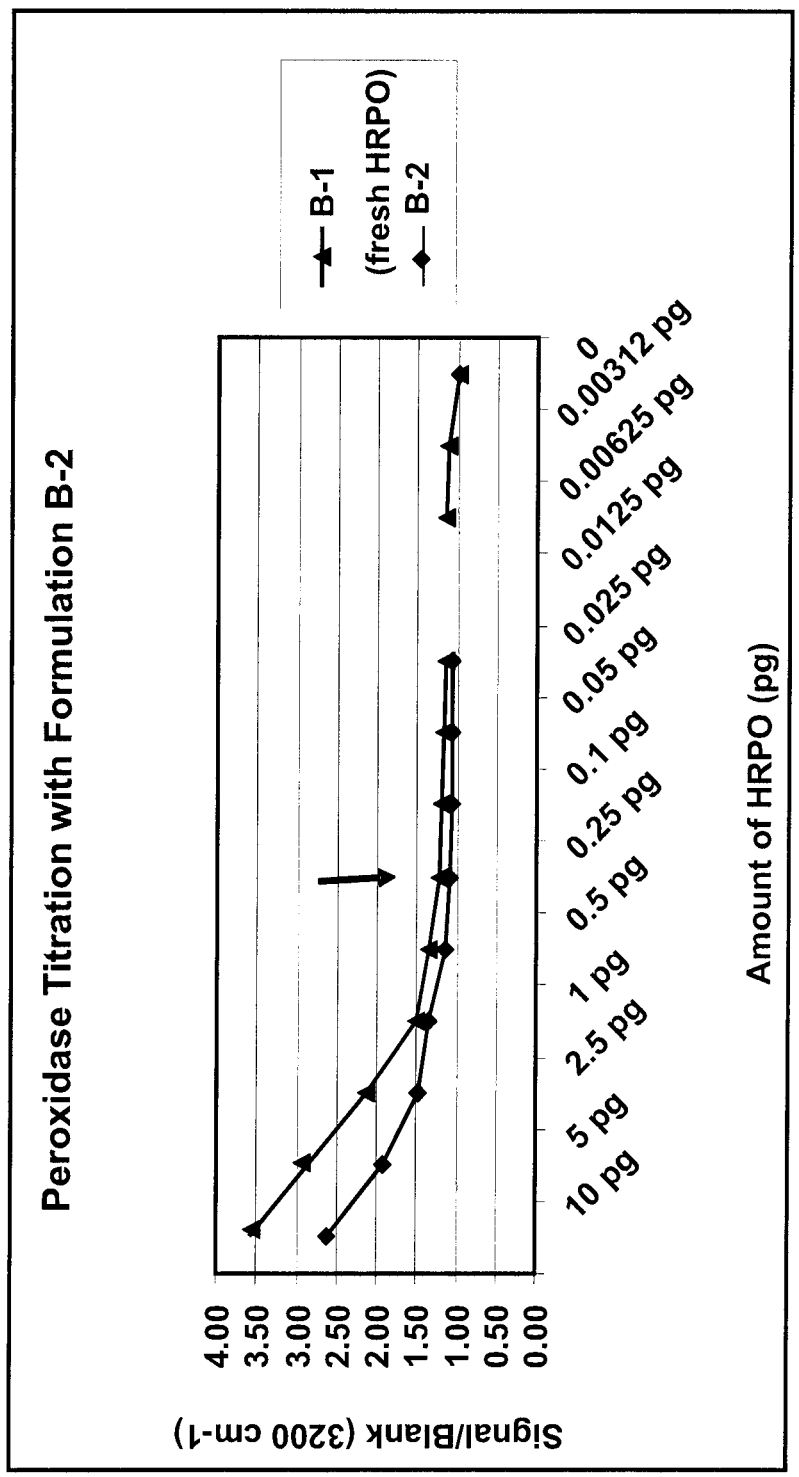
FIG. 14 plots Raman spectra measured at 3260 $cm^{-1}$ produced using Raman Reagent B-2 (squares) and B-2 with fresh HPRO in BSA diluent (diamonds).

HRPO was reacted in Raman Reagent B-1, B-2, B-3, and B-4. Raman spectra were recorded for HRPO dilutions from 0 ("blank") to 1000 pg/ml. FIG. 13 show the single peak (3260 cm-1) dependence on HRPO concentration. FIG. 14 shows single peak dependence on HRPO concentration and compares fresh HRPO in BSA diluent and formulation B-2

Table 9 compares the detection limits from several different Raman reagent B formulations, showing the increase in sensitivity provided by the SQR method.

TABLE 9

DETECTION LIMITS

| Formulation | Single peak | SQR | Increase in sensitivity |
|---|---|---|---|
| B-1 | 5 pg | 1 pg | 5 times |
| B-2 | 1 pg | 0.5 | 2 times |
| B-3 | 0.5 pg | 0.05 pg | 10 times |
| B-3* | 0.25 pg | 0.00625 pg | 40 times |
| B-4 | 1 pg | 0.5 pg | 5 times |

*Fresh HRPO in BSA diluent

Example 6

Raman Reagent C

Raman reagent formulations used for this study are listed in Table 10.

TABLE 10

RAMAN REAGENT C

| Formula | Buffer | ASA µg/ml | NAP µg/ml |
|---|---|---|---|
| C-1 | PBS-EDTA, pH 6.0 | 400 | 150 |
| C-2 | PBS-EDTA, pH 6.0 | 400 | 200 |
| C-3 | PBS-EDTA, pH 6.0 | 400 | 100 |
| C-UP | PBS-EDTA, pH 6.0 | 1000 | |

Figure 15:
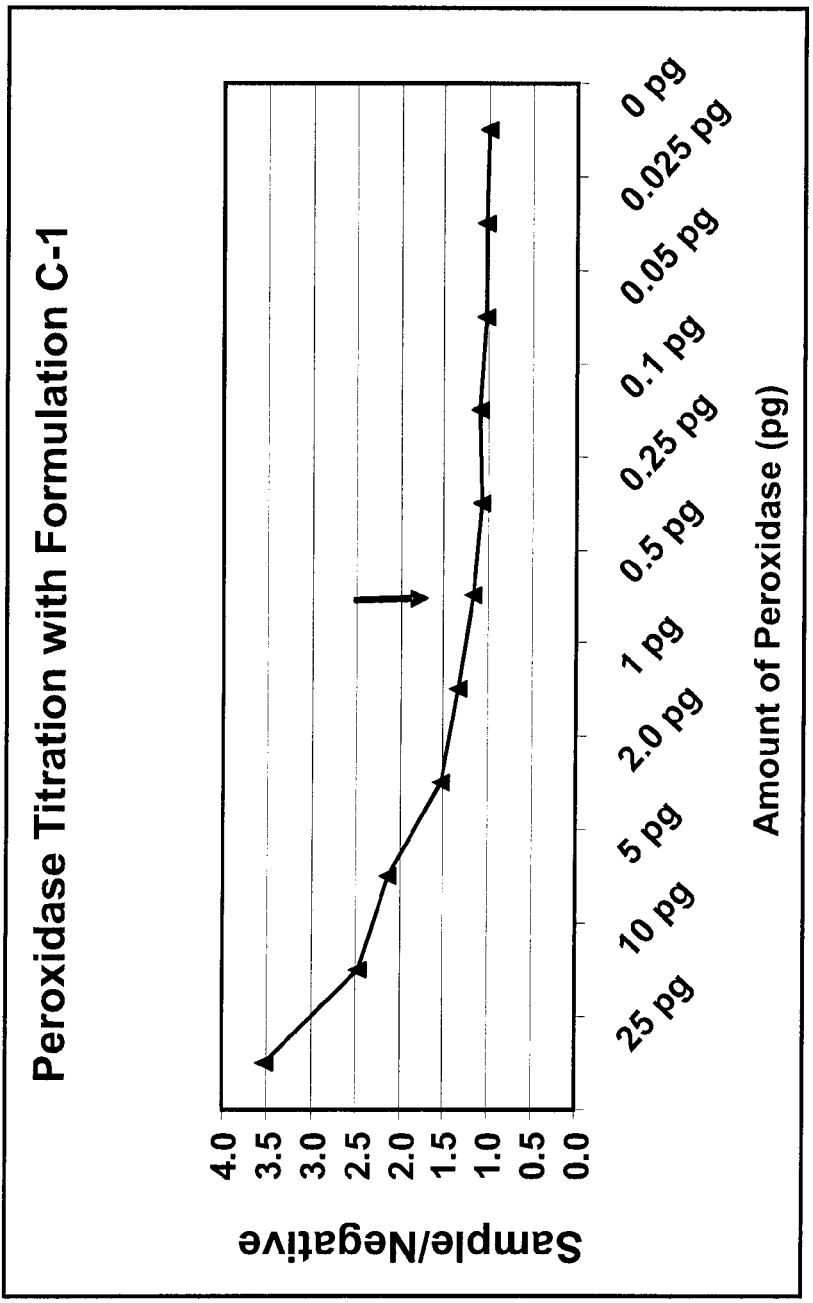
FIG. 15 A plots Raman spectra measured at 3260 $cm^{-1}$ produced using Raman Reagent C-1 while FIG. 15 B plots the corresponding SQR Raman spectra measured at 3500-4000 $cm^{-1}$.
Figure 15:
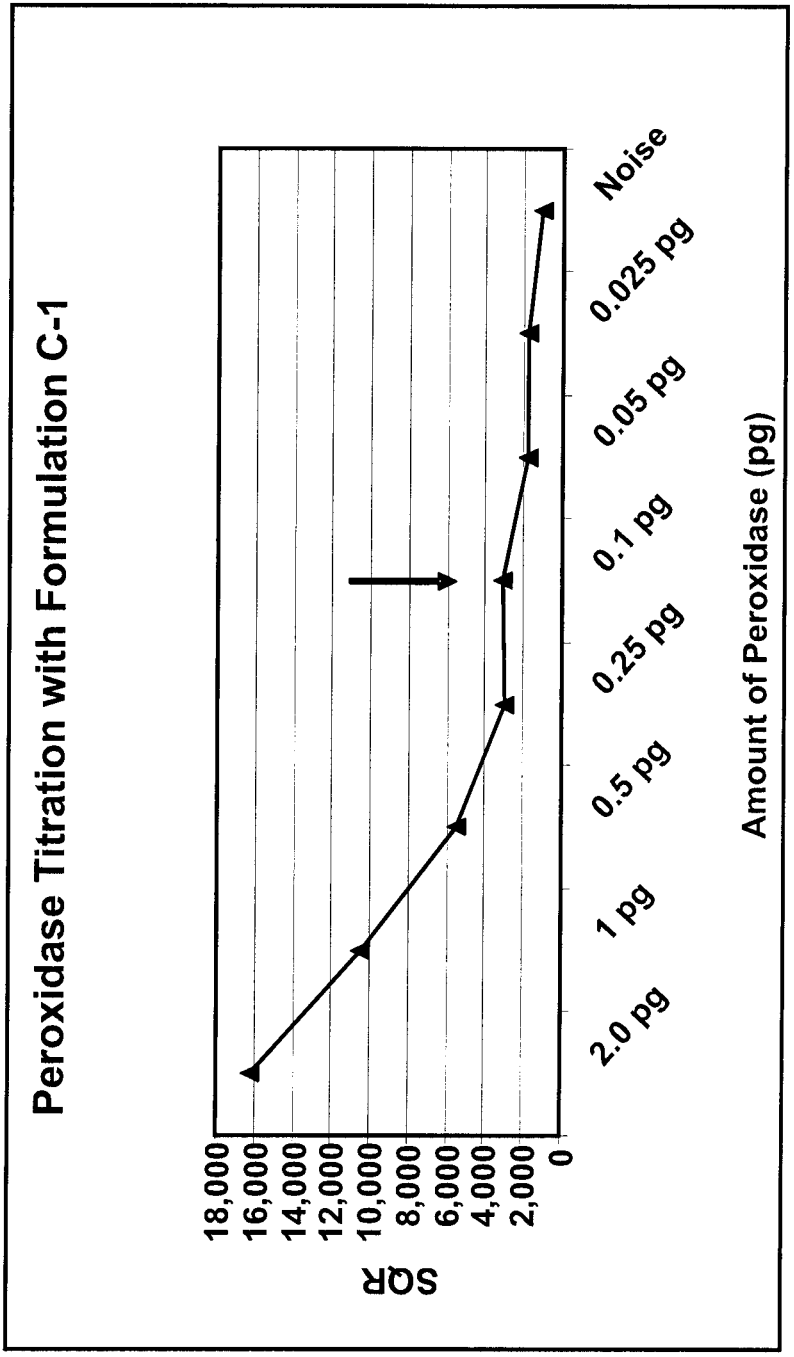

HRPO was reacted in Raman Reagent C-1. Spectra were recorded for HRPO dilutions from 0 ("blank") to 1000 pg/ml. FIG. 15 A shows the single peak (3260 cm$^{-1}$) dependence on HRPO concentration and FIG. 15 B shows the corresponding SQR spectra. Table 11 compares the detection limits for the single peak and SQR method, showing increased sensitivity from SQR.

TABLE 11

DETECTION LIMITS

| Formulation | Single peak | SQR | Increase in sensitivity |
|---|---|---|---|
| C-1 | 0.5 pg | 0.1 pg | 5 times |
| C-3* | 0.5 pg | 0.25 pg | 2 times |

*Fresh HRPO in BSA diluent

Example 7

Raman Reagent D

Raman reagent formulations used for this study are listed in Table 12.

TABLE 12

RAMAN REAGENT D

| Formula | Buffer | ASA µg/ml | HBCA µg/ml |
|---|---|---|---|
| D-1 | PBS-EDTA, pH 6.0 | 400 | 120 |
| D-UP | PBS-EDTA, pH 6.0 | 1000 | |

Figure 16:
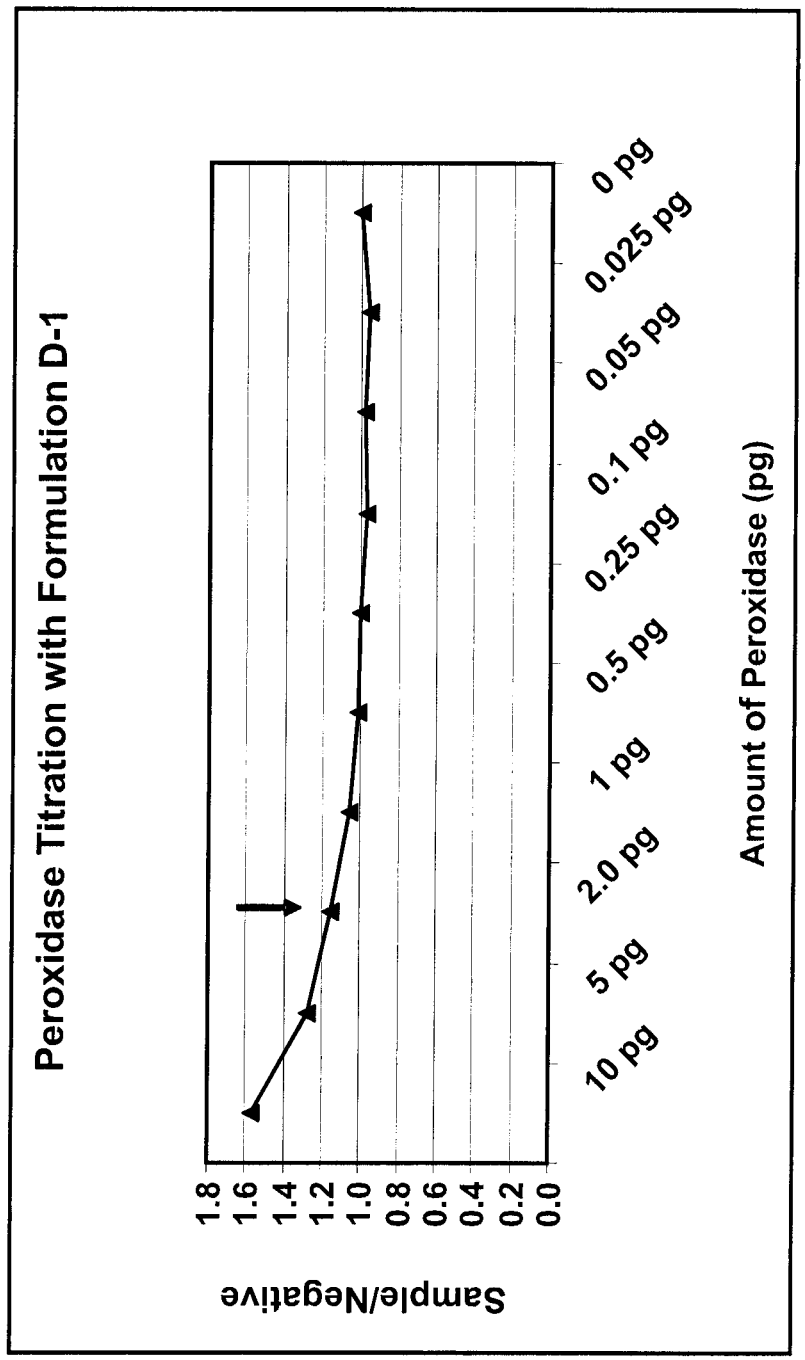
FIG. 16 A plots Raman spectra measured at 3260 $cm^{-1}$ produced using Raman Reagents D-1 while FIG. 16 B plots the corresponding SQR Raman spectra measured at 3500-4000 $cm^{-1}$.
Figure 16:
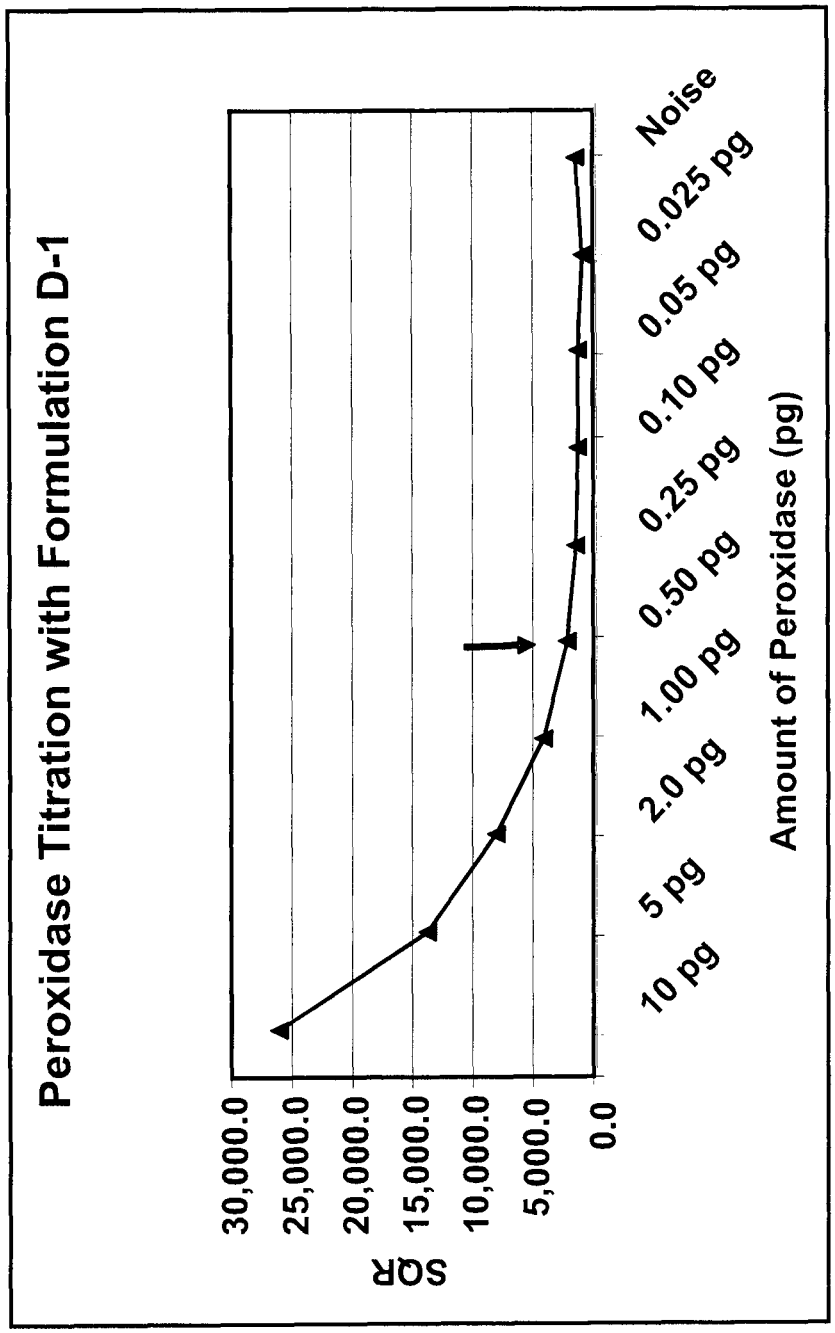

HRPO was reacted in Raman Reagent D-1. Spectra were recorded for HRPO dilutions from 0 ("blank") to 1000 pg/ml. FIG. 16A shows the single peak (3260 cm-1) dependence on HRPO concentration and FIG. 16B shows the corresponding SQR spectra.

TABLE 13

RAMAN REAGENT E

| Formula | Buffer | ASA µg/ml | DHQ µg/ml |
|---|---|---|---|
| E-1 | PBS-EDTA, pH 6.0 | 182 | 2270 |
| E-2 | PBS-EDTA, pH 6.0 | 360 | 91 |
| E-UP | PBS-EDTA, pH 6.0 | 1000 | |

HRPO was reacted in Raman Reagent D-1. The detection limit for Raman Reagent formulation D was 50 pg/ml.

Example 8

Sensitivity Tests

Sensitivity tests of Peroxidase with different Raman Reagents were done in PBS at pH 7.4, containing BSA. The study was intended to evaluate the sensitivity in PBS without BSA. The following reagents were used in this study:

Raman Reagent A-1: 500 µg/ml ASA; 20 µg/ml HBA; 20 µg/ml AA

Raman Reagent B-3: 250 µg/ml ASA; 25 µg/ml CDMP

Raman Reagent C-1: 400 µg/ml ASA; 150 µg/ml NAP

HRPO dilutions made to allow 1000 pg to 0.0125 pg per 50 µl sample were prepared in PBS at pH 7.4. 50 µl HRPO sample per dilution was added to 150 µl reagent and allowed to react for 30 minutes. 50 µl of 0.5 N NaOH was then added. After incubation for 30 minutes, Raman spectra were recorded using a Sword Diagnostics Raman Systems INC QE 65000 Raman Detector. Data were analyzed using SQR. Results from representative experiments appear in Tables 14-18.

Example 9

Biotin-ASA-Up, ASA-Up and ASA-Up in the Presence of Anti-Oxidant Agents

The objectives of these studies were to evaluate the sensitivity of Peroxidase with Biotin-ASA-UP and ASA-UP, and to investigate the effect of various anti-oxidant agents on ASA-UP.

Figure 17:
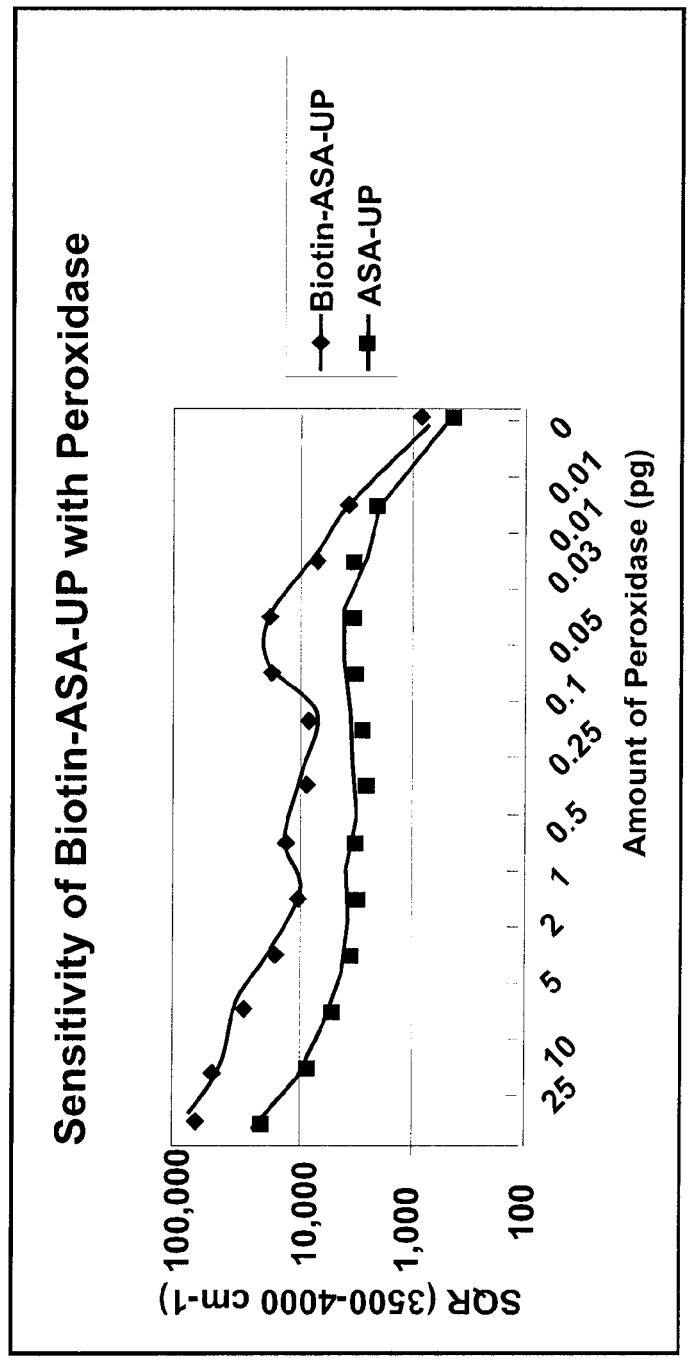
FIG. 17 plots SQR Raman spectra measured at 3500-4000 $cm^{-1}$ produced using Biotin-ASA-UP and ASA-UP.

The materials used were Biotin (125 µg/ml), and ASA (125 µg/ml) in PBS-EDTA, pH 6.0; and ASA (125 µg/ml) in PBS-EDTA, pH 6.0. Results in FIG. 17 show that the Biotin-ASA-UP combination provides a sensitive assay that can detect as low as 0.00625 pg sample. ASA-UP without HBA also enables detection as low as 2 pg of HRPO.

Figure 18:
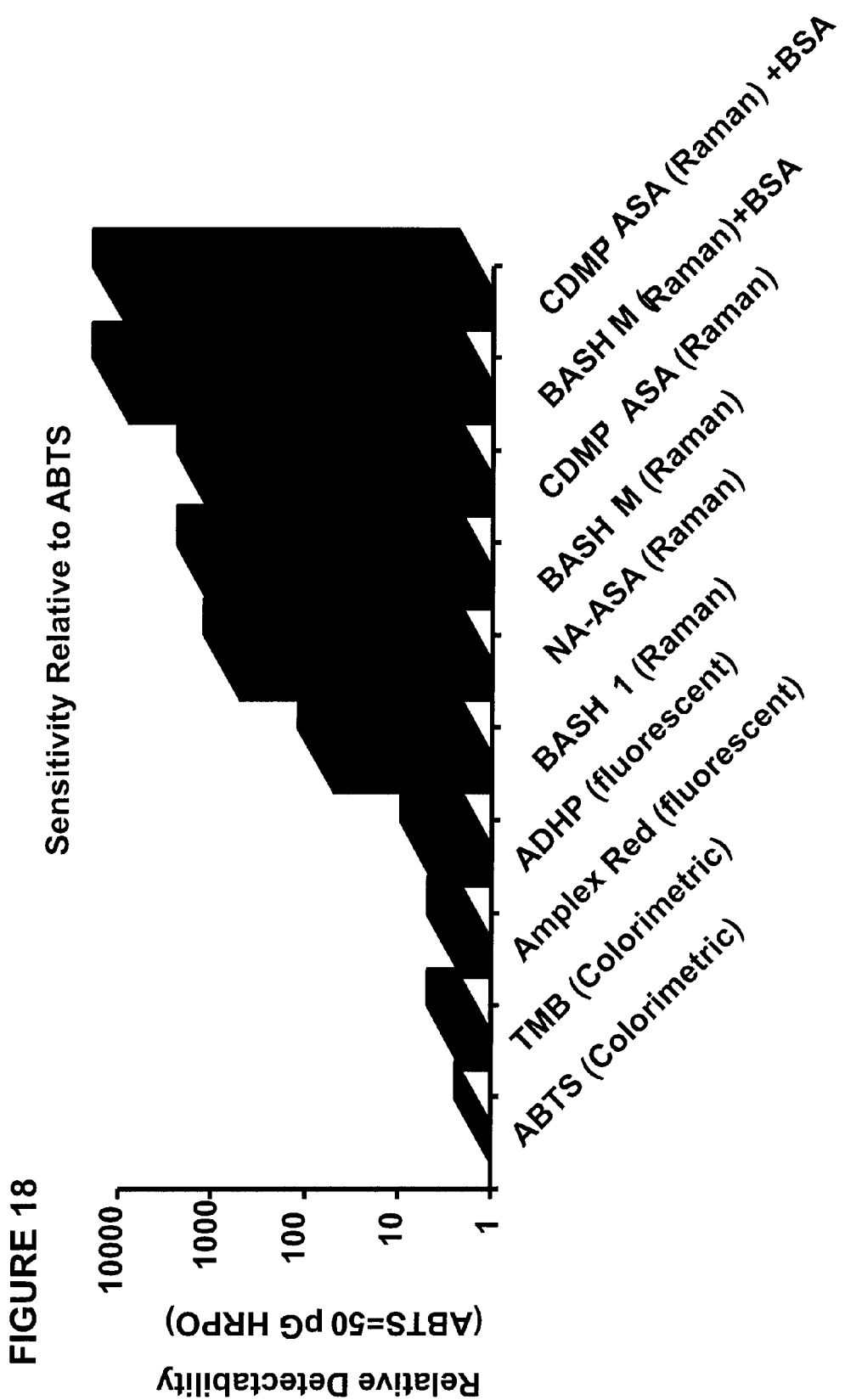
FIG. 18 is a bar graph showing the relative sensitivity of the reagents tested.

Representative results of comparisons of the Raman-based assays appear in Tables 14-18. Raman Reagent A (increasing ASA from 100 to 250 or 500 µg/ml), Reagent B, and Biotin-ASA provide ultra sensitive peroxidase assays, compared to Reagent A-1 and Reagent C formulations. Raman-based assays provide highly sensitive detection of Peroxidase in solution, which is shown graphically in FIG. 18.

Interestingly, ASA by itself provides very good sensitivity, which is increased by the addition of CDMP, Biotin and even NAP. In reactions based on A-1 in which ascorbate and HBA were omitted, the limit of detection of peroxidase was 3.9 and 4.4 pg/ml when 500 µg/ml of ASA was used and Raman signal analyzed with wave number $3,300^{cm-1}$ and SQR, respectively. When 750 µg/ml of ASA was used, the limit of detection was 2.3 and 1.9 when the Raman signal was analyzed with wave number $3,300^{cm-1}$ and SQR, respectively Use of fresh HRPO, HPRO that is used within about three hours of preparation, results in greater sensitivity, and samples should not be used after storage, even at 2-8° C. overnight if greater sensitivity is required. The following tables (Tables 14-18) summarize detection limits relevant to the preceding examples from representative experiments.

TABLE 14

SENSITIVITY OF RAMAN BASED ASSAY RELATIVE TO ABTS (SQR WITH 3500-4000 $CM^{-1}$)

| Peroxidase Formulations | Dilution Buffer | Sample/ Reaction Volume (µl) | Lowest Limit of Detection (pg) for 50 µl Sample | Sensitivity Relative ABTS |
|---|---|---|---|---|
| A-1 | PBS with BSA | 50/250 | 0.5 | 100 |
| C-1 | PBS with BSA | 50/250 | 0.1 | 500 |
| A-2 | PBS with BSA | 50/250 | 0.05 | 1000 |
| A-2 | PBS with BSA, Fresh HRPO | 50/250 | 0.00625 | 8000 |
| B-3 | PBS with BSA | 50/250 | 0.05 | 1000 |
| B-3 | PBS with BSA, Fresh HRPO | 25/250 | 0.00625 | 8000 |
| Biotin-ASA | PBS with BSA, Fresh HRPO | 25/250 | 0.00625 | 8000 |
| ASA-UP | PBS with BSA, Fresh HRPO | 25/250 | 2.0 | 25 |

TABLE 15

DETECTION LIMITS WITH RAMAN REAGENT FORMULATIONS WITH HRPO IN BSA DILUENT

| Peroxidase Formulations | Dilution Buffer | Sample/ Negative | SQR | Increase in Sensitivity from Single Peak to SQR |
|---|---|---|---|---|
| B-1 | PBS with 0.1% BSA | 5 pg | 1 pg | 5 times |
| B-2 | PBS with 0.1% BSA | 1 pg | 0.5 pg | 2 times |
| B-3 | PBS with 0.1% BSA | 0.5 pg | 0.05 | 10 times |
| B-3 | PBS with 0.1% BSA. Fresh HRPO | 0.25 pg | 0.00625 pg | 40 times |
| B-4 | PBS with 0.1% BSA | 2.5 pg | 0.5 pg | 5 times |
| A-1 | PBS with 0.1% BSA | 1 pg | 0.5 pg | 2 times |
| A-2 | PBS with 0.1% BSA | 1 pg | 0.05 pg | 20 times |
| A-2 | PBS with 0.1% BSA. Fresh HRPO | 0.25 pg | 0.00625 pg | 40 times |

TABLE 15-continued

DETECTION LIMITS WITH RAMAN REAGENT FORMULATIONS WITH HRPO IN BSA DILUENT

| Formulations | Peroxidase Dilution Buffer | Sample/ Negative | SQR | Increase in Sensitivity from Single Peak to SQR |
|---|---|---|---|---|
| A-3 | PBS with 0.1% BSA | 1 pg | 1 pg | No Change |
| C-2 | PBS with 0.1% BSA | 0.5 pg | 0.1 pg | 5 times |
| C-3 | PBS with 0.1% BSA, Fresh HRPO | 0.5 pg | 0.25 pg | 2 times |
| D-1 | PBS with 0.1% BSA | 2 pg | 0.5 pg | 4 times |
| E-2 | PBS with 0.1% BSA | 50 pg | NA | NA |

TABLE 16

DETECTION LIMITS WITH RAMAN REAGENT FORMULATIONS WITH HRPO IN PBS DILUENT

| Formulations | Peroxidase Dilution Buffer | Sample/ Negative | SQR | Increase in Sensitivity from Single Peak to SQR |
|---|---|---|---|---|
| A-2 | PBS, pH 7.4 | 0.5 pg | 0.0125 pg | 40 times |
| B-3 | PBS, pH 7.4 | 0.5 pg | 0.5 pg | None |
| C-3 | PBS, pH 7.4 | 1 pg | 0.0125 pg | 80 times |
| A-2 | PBS, pH 7.4, Fresh | 2.5 pg | 0.05 pg | 50 times |
| B-3 | PBS, pH 7.4, Fresh | 0.25 pg | 0.05 pg | 5 times |
| C-3 | PBS, pH 7.4, Fresh | 0.5 pg | 0.0125 pg | 40 times |

TABLE 17

DETECTION LIMITS WITH COLORIMETRIC AND FLUOROGENIC REAGENTS

| Formulations | Peroxidase Dilution Buffer | Time of Incubation (Minutes) | Sample/ Reaction Volume (µl) | Lowest Limit of Detection (pg) for 50 µl Sample |
|---|---|---|---|---|
| TMB | PBS, pH 7.4 with or w/o BSA | 30 | 50/250 | 25 |
| ABTS | PBS, pH 7.4 with or w/o BSA | 30 | 50/250 | 50 |
| Amplex Red Fluorogenic | PBS, pH 7.4 with or w/o BSA | 30 | 400/800 | 25 |
| AnaSpec ADHP Fluorogenic | PBS, pH 7.4 with or w/o BSA | 30 | 400/800 | 12.5 |
| A-1 | PBS with BSA | 30/30 | 50/250 | 0.5 |
| A-2 | PBS with BSA | 30/30 | 50/250 | 0.05 |
| A-3 | PBS with BSA | 30/30 | 50/250 | 1 |
| A-2 | PBS with BSA, Fresh HRPO | 30/30 | 50/250 | 0.00625 |
| A-2 | PBS, pH 7.4 | 30/30 | 50/250 | 0.0125 |
| A-2 | PBS, pH 7.4, Fresh HRPO | 30/30 | 50/250 | 0.05 |
| B-1 | PBS with BSA | 30/30 | 50/250 | 1 |
| B-2 | PBS with BSA | 30/30 | 50/250 | 5 |
| B-4 | PBS with BSA | 30/30 | 50/250 | 0.50 |
| B-3 | PBS with BSA | 30/30 | 50/250 | 0.05 |
| B-3 | PBS with BSA, Fresh HRPO | 30/30 | 50/250 | 0.00625 |
| B-3 | PBS, pH 7.4, Fresh HRPO | 30/30 | 50/250 | 0.05 |
| B-3 | PBS, pH 7.4 | 30/30 | 50/250 | 0.50 |
| C-1 | PBS with 0.1% BSA | 30/30 | 50/250 | 0.10 |
| C-3 | PBS with BSA, Fresh HRPO | 30/30 | 50/250 | 0.25 |
| C-3 | PBS, pH 7.4 | 30/30 | 50/250 | 0.0125 |
| C-3 | PBS, pH 7.4, Fresh HRPO | 30/30 | 50/250 | 0.0125 |
| Biotin-ASA 125/125 | PBS, pH 7.4, Fresh HRPO | 30/30 | 50/250 | 0.00625 |

Note that the Amplex Read Peroxidase assay is linear between 25 and 250 pg/50 µl of sample (per vendor's claim) and the assay is able to detect as low as $1 \times 10^{-5}$ U/ml. The Sigma HRPO used in the current study had an activity of 1080 U/mg solid. On this basis, $1 \times 10^{-5}$ U/ml HRPO is equivalent to 10 pg/ml (0.5 pg/50 µl).

Table 18 summarizes a representative comparison of Raman-based detection and detection by absorbance, chemiluminescence, and fluorescence.

TABLE 18

SUMMARY OF COMPARATIVE DATA

| Reagent | Technique | Limit of Detection | Dynamic range (Peroxidase conc. in pg/ml) | |
|---|---|---|---|---|
| BASH-UP (SQR) | Raman | 3-6 pg/mL | 1,250 fold | 4 to 5,000 |
| TMB Detection ($A_{450}$) | Absorbance | 8 pg/mL | 125 fold | 8 to 1,000 |
| ABTS Detection ($A_{405}$) | Absorbance | 32 pg/mL | 156 fold | 32 to 5,000 |
| OPD Detection ($A_{492}$) | Absorbance | 55 pg/mL | 91 fold | 55 to 5,000 |
| LumiGLO Detection | Chemiluminescence | 11 pg/mL | 455 fold | 11 to 5,000 |
| Amplex Red | Fluorescence | 257 pg/mL | 91 fold | 257 to 5,000 |

The effect of various anti-oxidant agents on Raman-based detection assays was examined. The effect of anti-oxidant agents on peroxidase reactions using 750 µg/ml ASA in representative experiments are summarized in Table 19.

TABLE 19

EFFECTS OF ANTI-OXIDANTS

Anti-Oxidant Agents

| 3,300 Raman Signal | Ascorbate | N-Acetyl-L-Cystine | Melatonin | Gallic Acid | Sodium Meta-bisulfite | Sodium Selenite |
|---|---|---|---|---|---|---|
| Negative (0 pg/mL HRPO) | 953 | 1052 | 953 | 1031 | 978 | 903 |
| Negative + Anti-Oxidant | 411 | 677 | 965 | 1585 | 2453 | 966 |
| Positive (125 pg/mL HRPO) | 2177 | 2369 | 3395 | 3022 | 2297 | 2887 |
| Positive + Anti-Oxidant | 751 | 1499 | 3198 | 2480 | 1920 | 2950 |
| Positive Signal/Noise Ratio | 1.8 | 2.2 | 3.3 | 1.6 | 1.97 | 3.1 |

Example 10

Immunoassays Using Raman-Based Detection

Raman-based methods were employed to the immunoassay formats available from R&D Systems Inc. (D2050), BD Biosciences (5506111), BD Biosciences (557825), R&D Systems Inc. (DRT200), and BioCheck Inc (BC-1105). The assay protocols were followed according to the manufacturer's instructions, with the exception that substrates producing Raman-active compounds were substituted for TMB. The experiments using Raman-active compounds were conducted as follows:

Reagent A
1. 5-Aminosalicylic Acid: 250 ug/mL
2. 2-Hydroxybenzyl Alcohol: 20 ug/mL
3. Ascorbic Acid: 0.2 ug/mL The above three reagents were dissolved in 10 mM phosphate buffered saline with 1 mM EDTA, pH 6.0 (PBS-EDTA) and filtered through a sterile 0.45 micron cellulose nitrate filter and was stored in an amber-colored polyethylene bottle at 2-8° C.

Reagent B
1. Urea-Peroxide: 1000 ug/mL which contains 360 ug/mL Hydrogen Peroxide The reagent was dissolved in 10 mM phosphate buffered saline with 2 mM EDTA, pH 6.0 (PBS-EDTA) and filtered through a sterile 0.45 micron cellulose nitrate filter and was stored in an amber colored polyethylene bottle at 2-8 degree.

Raman Substrate

Raman substrate was prepared by mixing Reagent A and Reagent B in a volume ratio of 9:1 prior to use. The substrate should be used in the same of preparation.

The results from representative experiments are summarized in Table 20.

TABLE 20

RAMAN-BASED IMMUNOASSAYS

| | Limit of Detection | | | Dynamic Range | |
|---|---|---|---|---|---|
| Analyte | Raman | TMB | Mfg. Claim | Raman | Mfg. Claim |
| Human IL-2 (R&D) | 2 pg/mL | 47 pg/mL | 7 pg/mL | 2-2,000 | 31-2,000 |
| Human IL-2 (BD) | 2 pg/mL | 6.5 pg/mL | 4 pg/mL | 2-500 | 7.8-500 |
| C-Reactive Protein | 2-4 µg/mL | 20 µg/mL | 4.2 µg/mL | 2-133 | 4.2-133 |
| Tumor Necrosis Factor Receptor II | 0.3 pg/mL | 0.3 pg/mL | 0.6 pg/mL | 0.3-500 | 7.8-500 |
| Human Cardiac Troponin I | 0.5 ng/mL | 3 ng/mL | 1 ng/mL | 2-75 | 2-75 |

Figure 19:
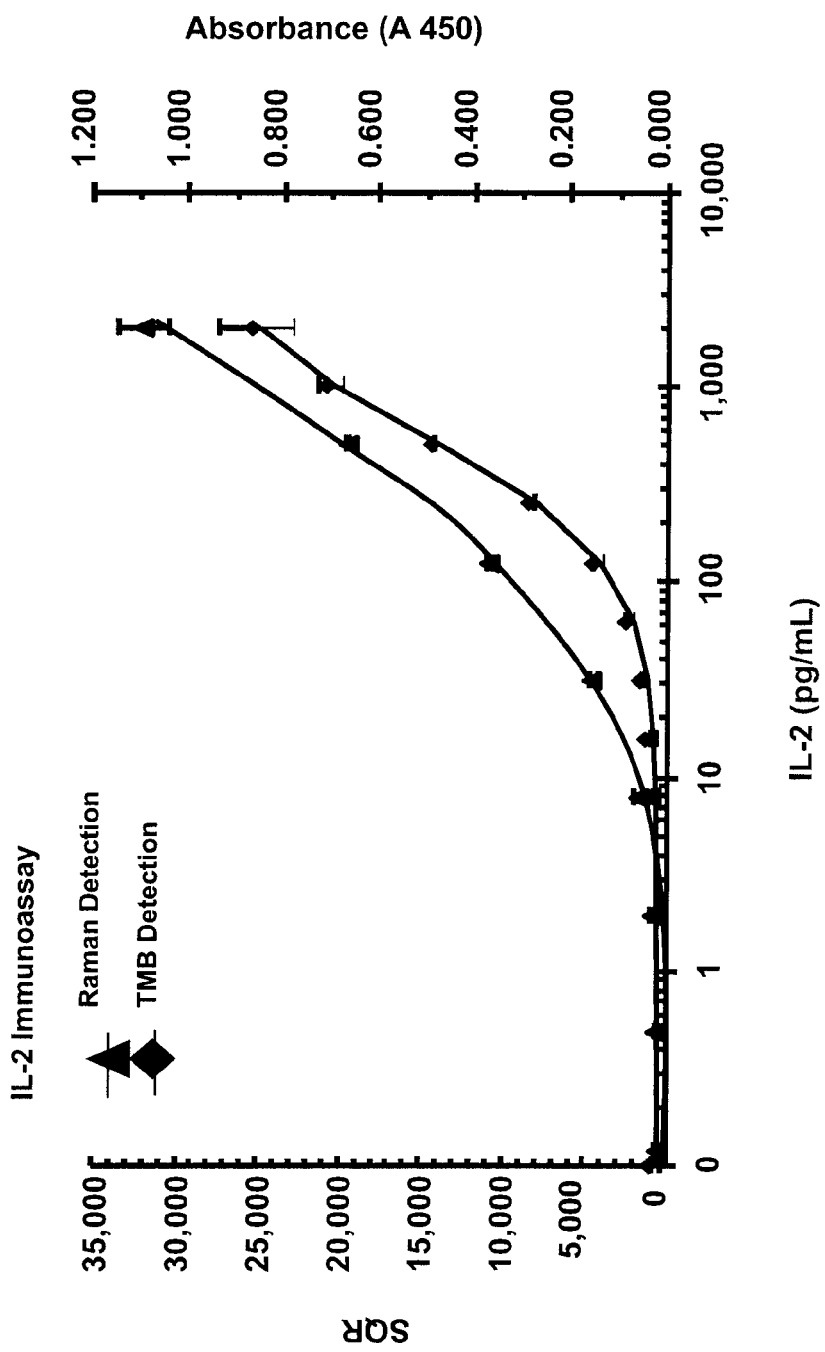
FIG. 19 is a plot of the SQR Raman spectra measured at 3500-4000 $cm^{-1}$ and absorbance spectrum measured at 450 nm in IL-2 immunoassays using BASH-UP and TMB.

Introduction of substrates producing Raman-active products into the Human IL-2 assay resulted in an approximately 5-20 fold improvement in assay sensitivity. FIG. 19. The shift of the IL-2 dose response curve to the left demonstrated in FIG. 19 exemplifies this improved sensitivity.

Example 11

Absorbance, Fluorescence, and Raman Detection of Bash-Up and OPD Reactions with HRPO Studies using o-phenylenediamine as a peroxidase substrate revealed that OPD produces a Raman signal that is peroxidase dependent, does not require addition of NaOH, and can be detected over a wide range of wave numbers. The signal is more pronounced in the absence of NaOH, but is present in an altered form when the reaction is stopped with either NaOH or $H_2SO_4$.

Studies were done to evaluate the fluorescence and absorption characteristics of Raman peroxidase reactions using o-phenylenediamine (OPD) and BASH-UP substrate solutions. The OPD and BASH-UP reactions were prepared according to the following procedures:

OPD protocol:
1. prepare OPD substrate solutions per SIGMAFAST™ OPD instructions;
2. prepare HRPO peroxidase dilutions in buffer (PBS-BSA) to 4,000 pg/ml;
3. prepare the OPD/peroxide substrate solution (substrate solution should be used within one hour of preparation);
4. add 250 µl diluted peroxidase sample to each reaction tube;
5. add 750 µl OPD/peroxide substrate to each tube; and
6. mix and incubate for 15 min in the dark at room temperature.

BASH-UP Protocol:
1. prepare the BASH-UP substrate solution (9:1 BASH to UP, v/v);
2. add 200 µl of diluted peroxidase dilution to each reaction tube;
3. add 600 µl BASH-UP substrate solution to each tube;
4. mix and incubate for 30 min at room temperature;
5. add 200 µl of 0.5 N NaOH stop solution to each reaction tube; and
6. mix and incubate for 30 min at room temperature.

Reactions with either BASH-UP, or OPD-peroxide reagents were performed on sample solutions containing either 0 or 2,000 pg/ml peroxidase as follows:

OPD Reactions
1. Mix 250 µl of 2,000 pg/ml Peroxidase+750 µl OPD-peroxide substrate solution;
2. Mix 250 µl of 1×PBS-BSA Buffer+750 µl OPD-peroxide substrate solution;
3. Add peroxidase and allow reaction to proceed in the dark.
4. Read spectrum 30 min after the reaction time has expired.

BASH Reactions
1. 200 µl peroxidase (at 2,000 pg/ml conc.)+600 µl BASH-UP+200 µl 0.5 N NaOH
2. 200 µl of 1×PBS-BSA buffer+600 µl BASH-UP+200 µl 0.5 N NaOH
3. Add peroxidase and BASH, react 30 min, stop with NaOH.
4. Read spectrum 30 min after stopping the reaction.

Absorbance.

Figure 20:
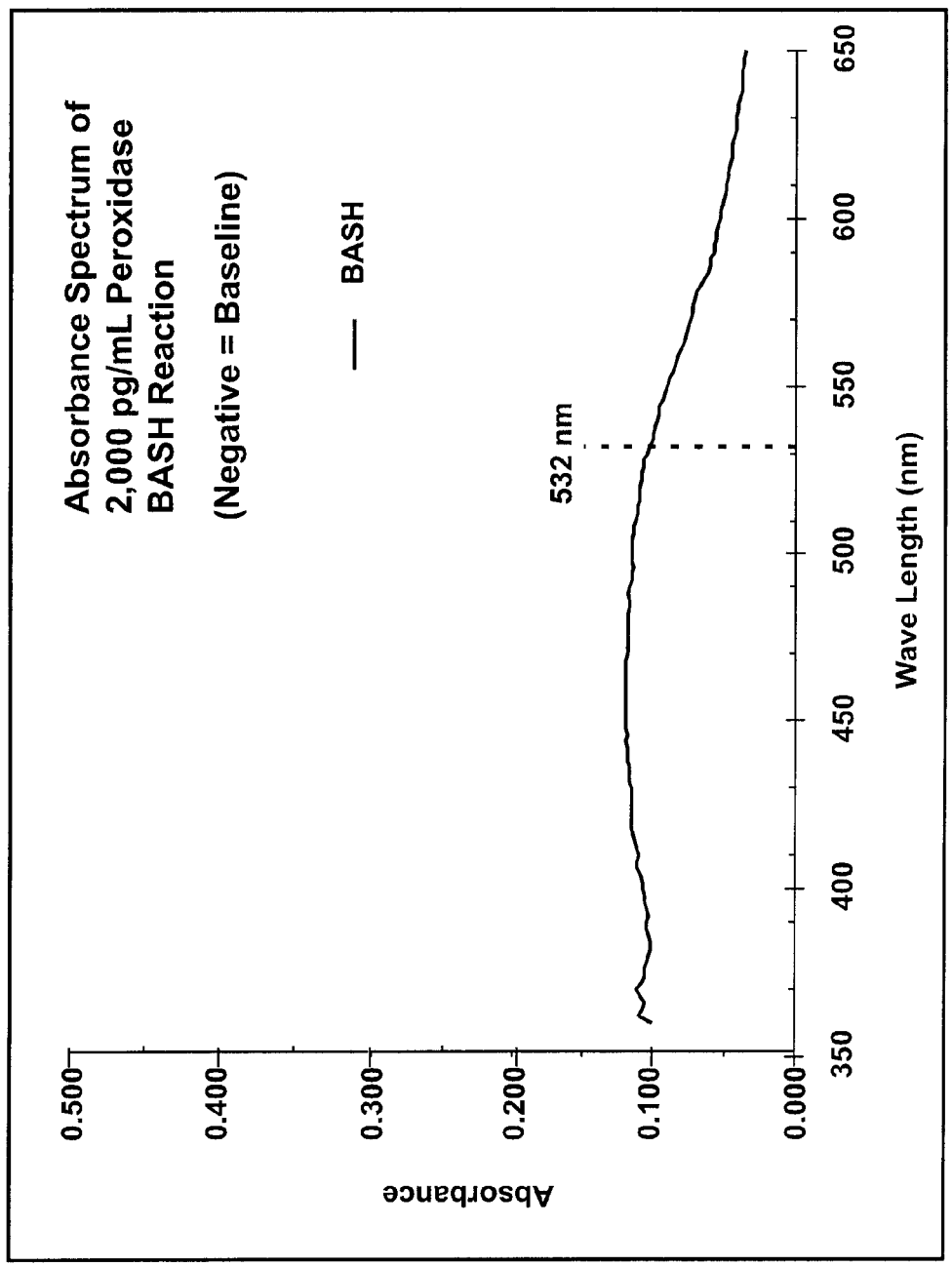
FIG. 20 A is a plot of an absorbance spectrum for a BASH-UP reaction, while FIG. 20 B is an absorbance spectrum for an OPD reaction.
Figure 20:
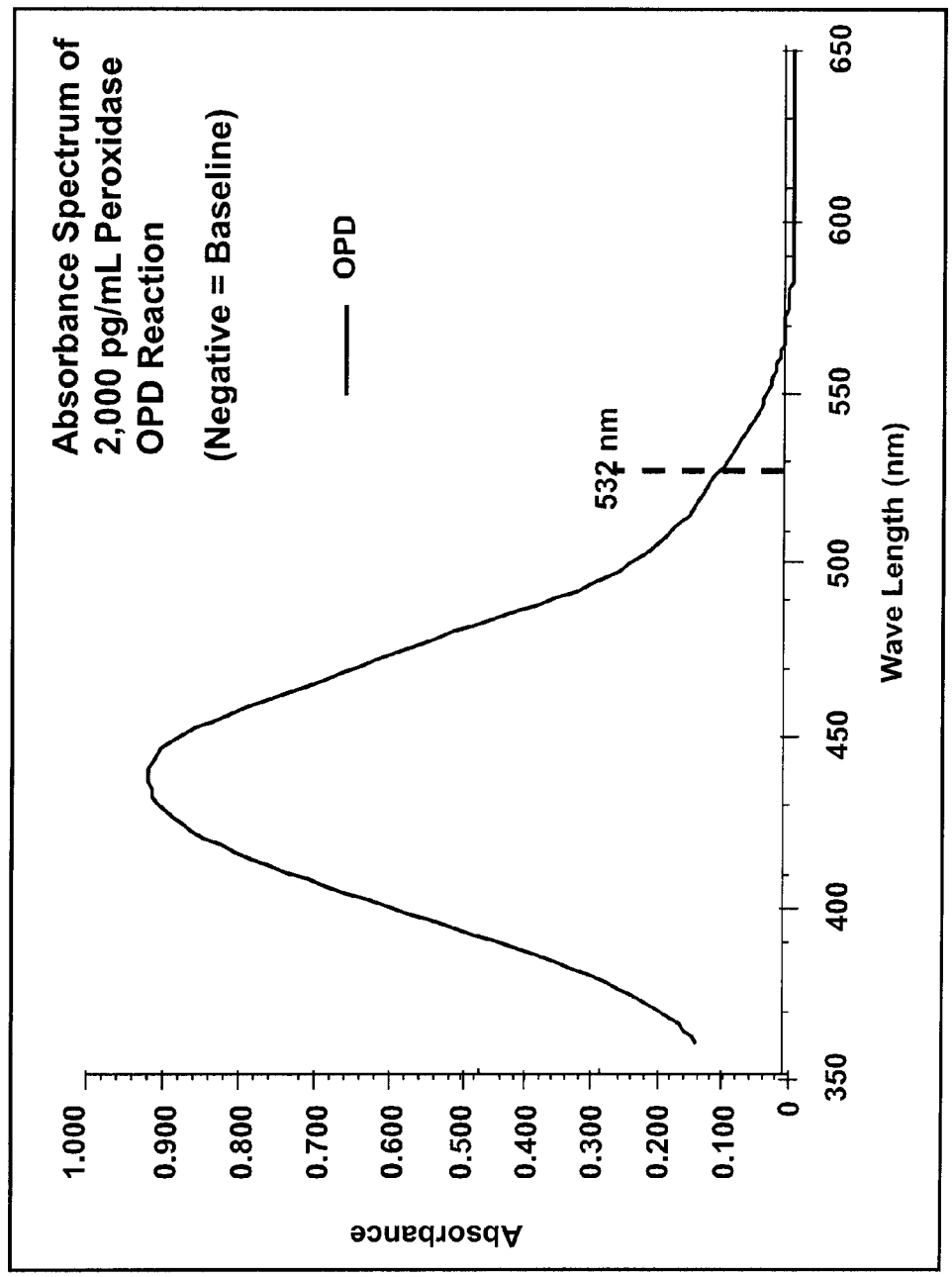

Scans were performed with a Digilab Hitachi U-2800 spectrophotometer and spectra were recorded using 0.750 ml of each reaction sample using a single beam mode. The background sample (0 pg/ml peroxidase) was used as baseline. Spectra (340 to 650 nm; 1200 nm/min scan rate; 2 nm interval) are shown in FIGS. 20 A and 20 B. The absorption spectra of the BASH reaction was broad covering the visible wavelength range (centered around 500 nm) lacking distinct peaks associated with a unique absorbing species (FIG. 20 A). The absorption spectra of the OPD reaction was more defined (FIG. 20 B), with a broad peak near 440 nm (yellow wavelength range).

Fluorescence.

Figure 21:
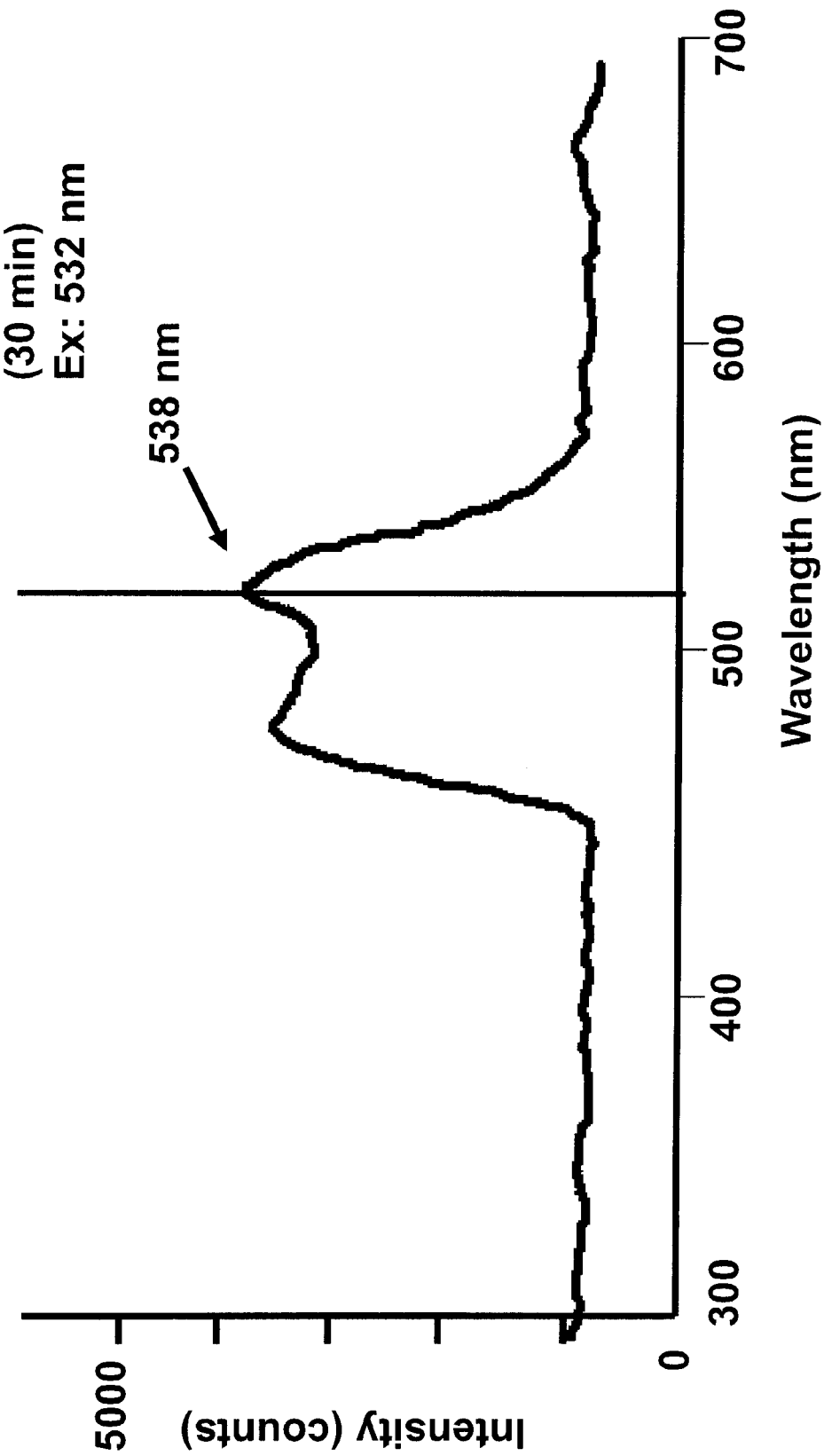
FIGS. 21 A and 21 B are plots of fluorescence spectra of BASH-UP reactions without peroxidase, and FIGS. 21 C and 21 D are plots of fluorescence spectra of BASH-UP reactions with peroxidase.
Figure 21:
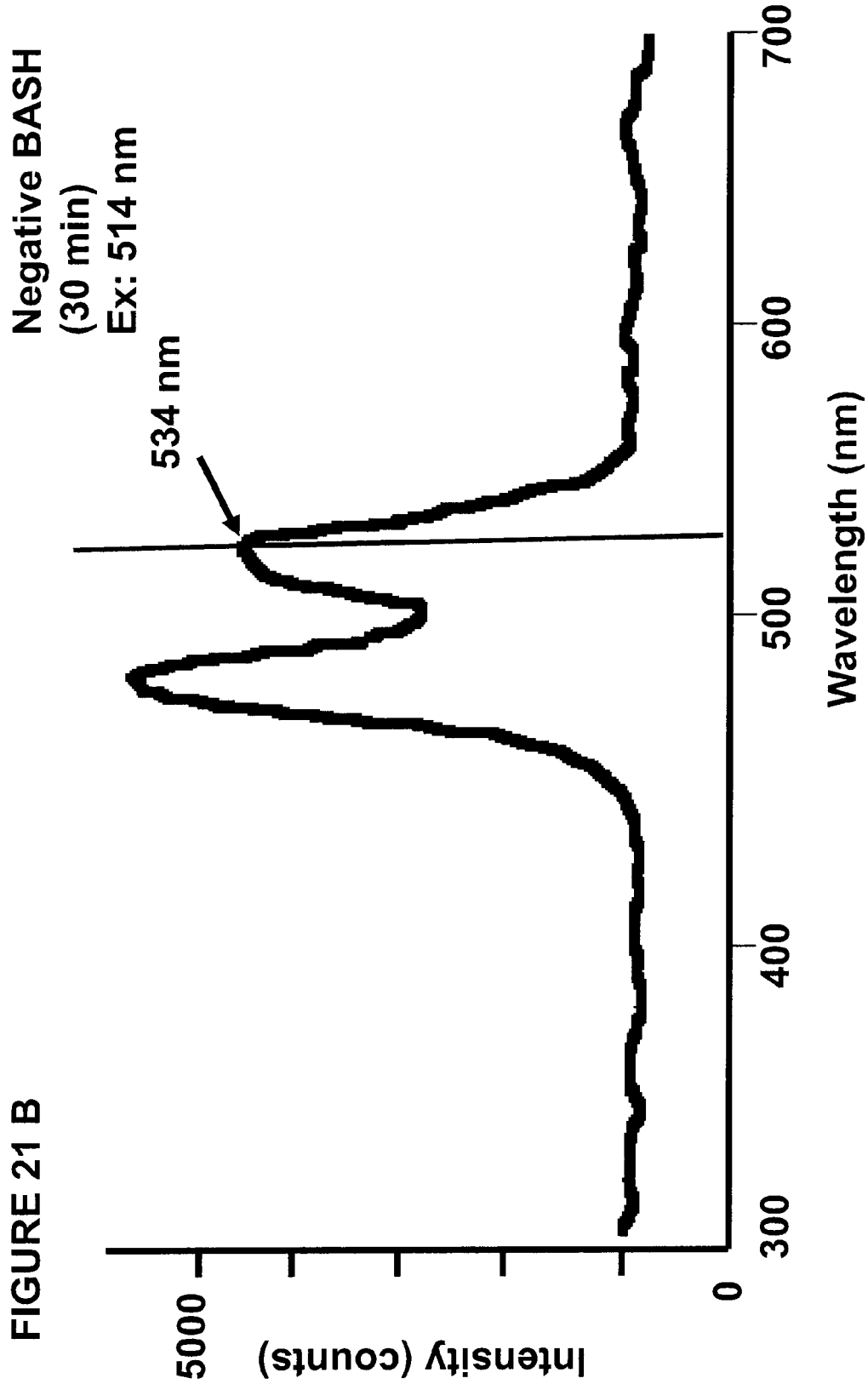
Figure 21:
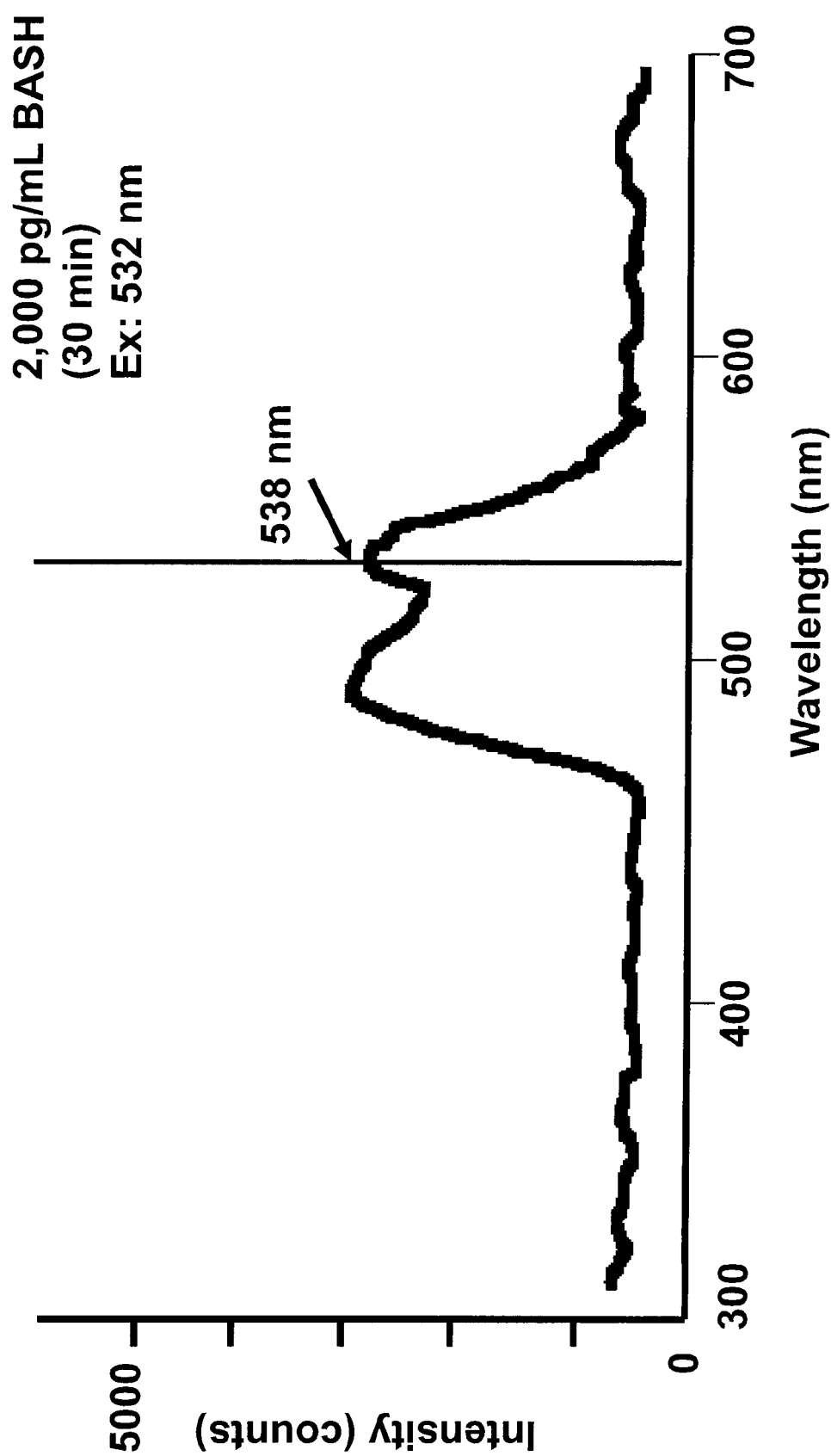
Figure 21:
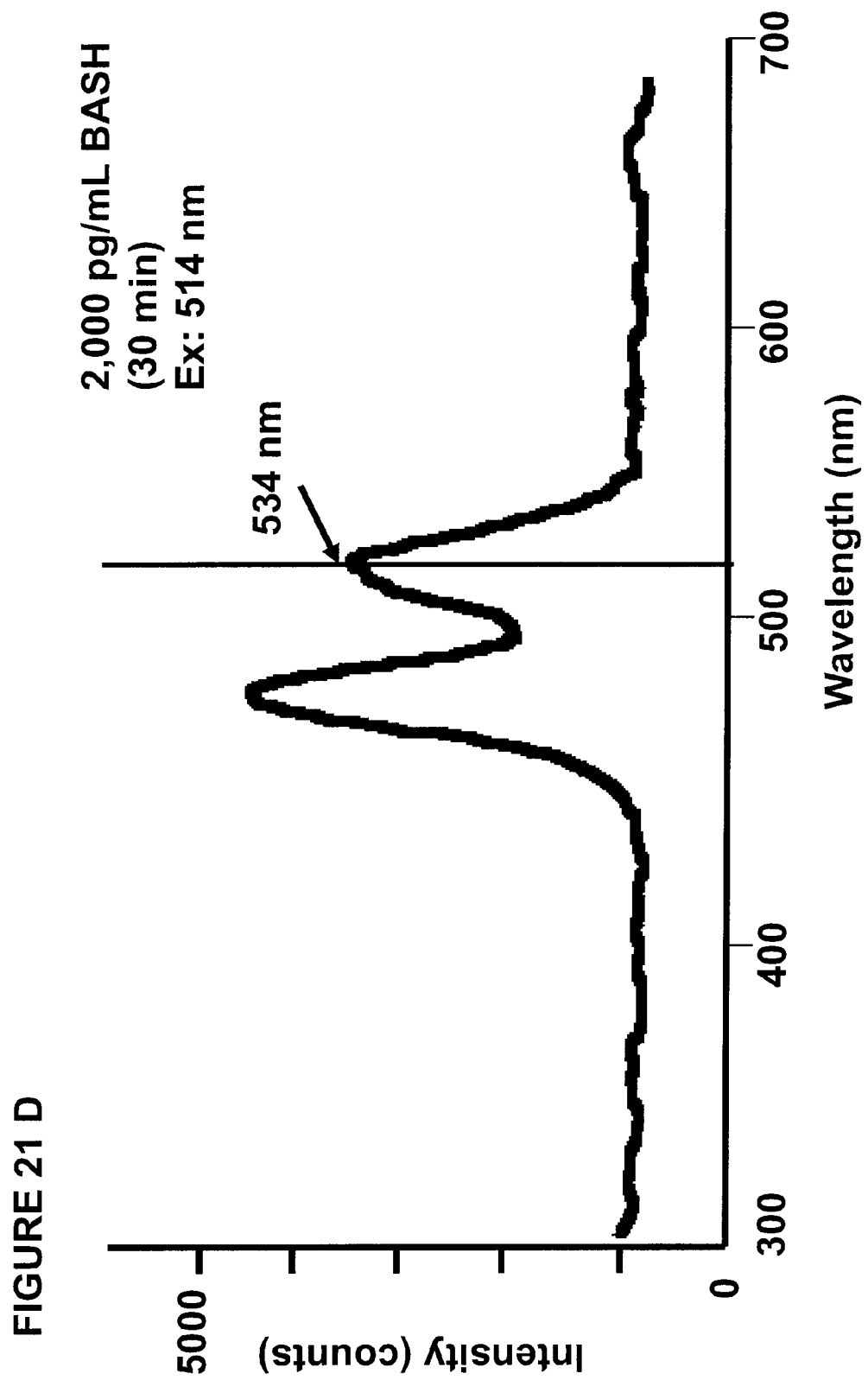
Figure 22:
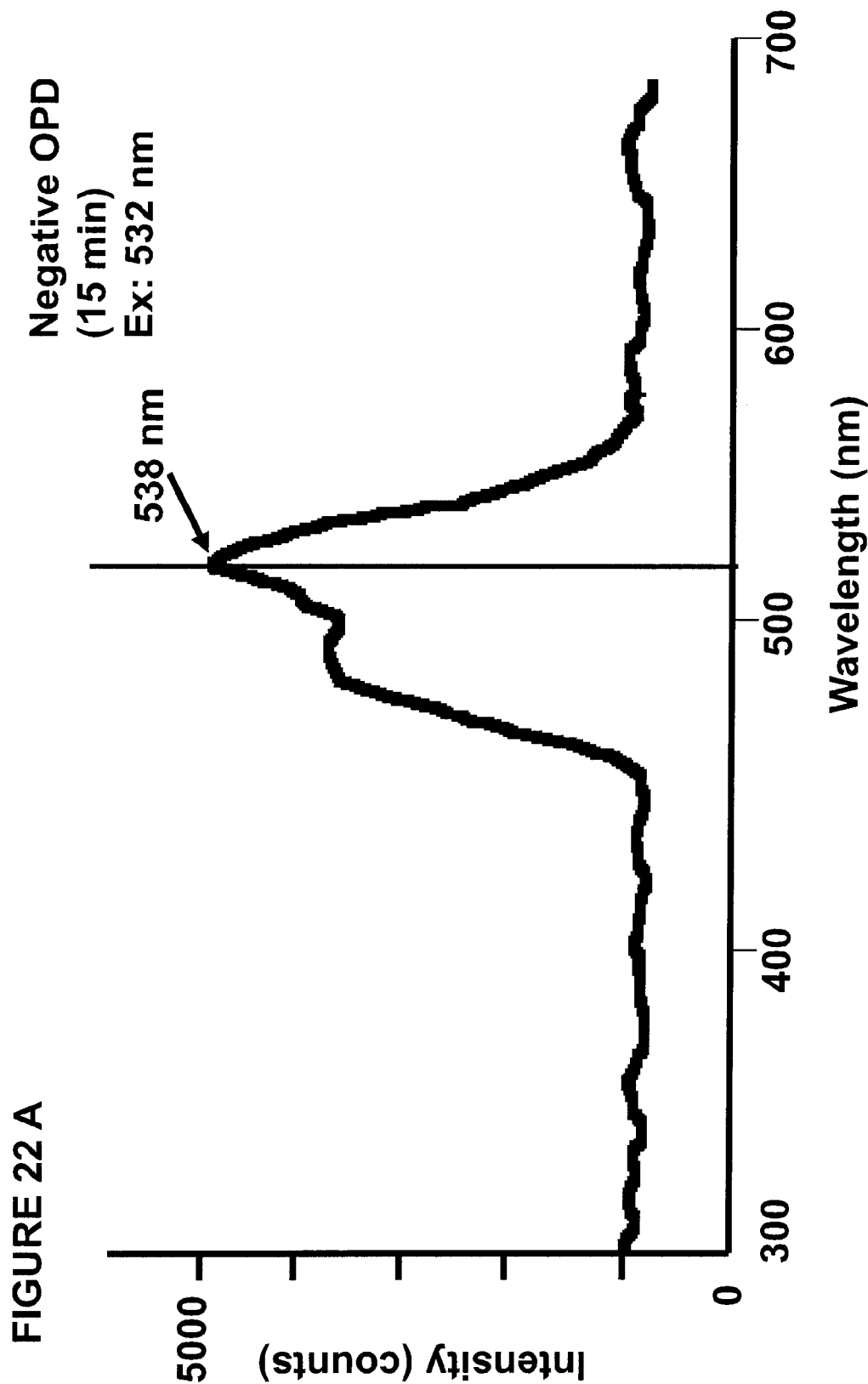
FIGS. 22 A and 22 B are plots of fluorescence spectra of OPD reactions without peroxidase, and FIGS. 22 C and 22 D are plots of fluorescence spectra of OPD reactions with peroxidase.
Figure 22:
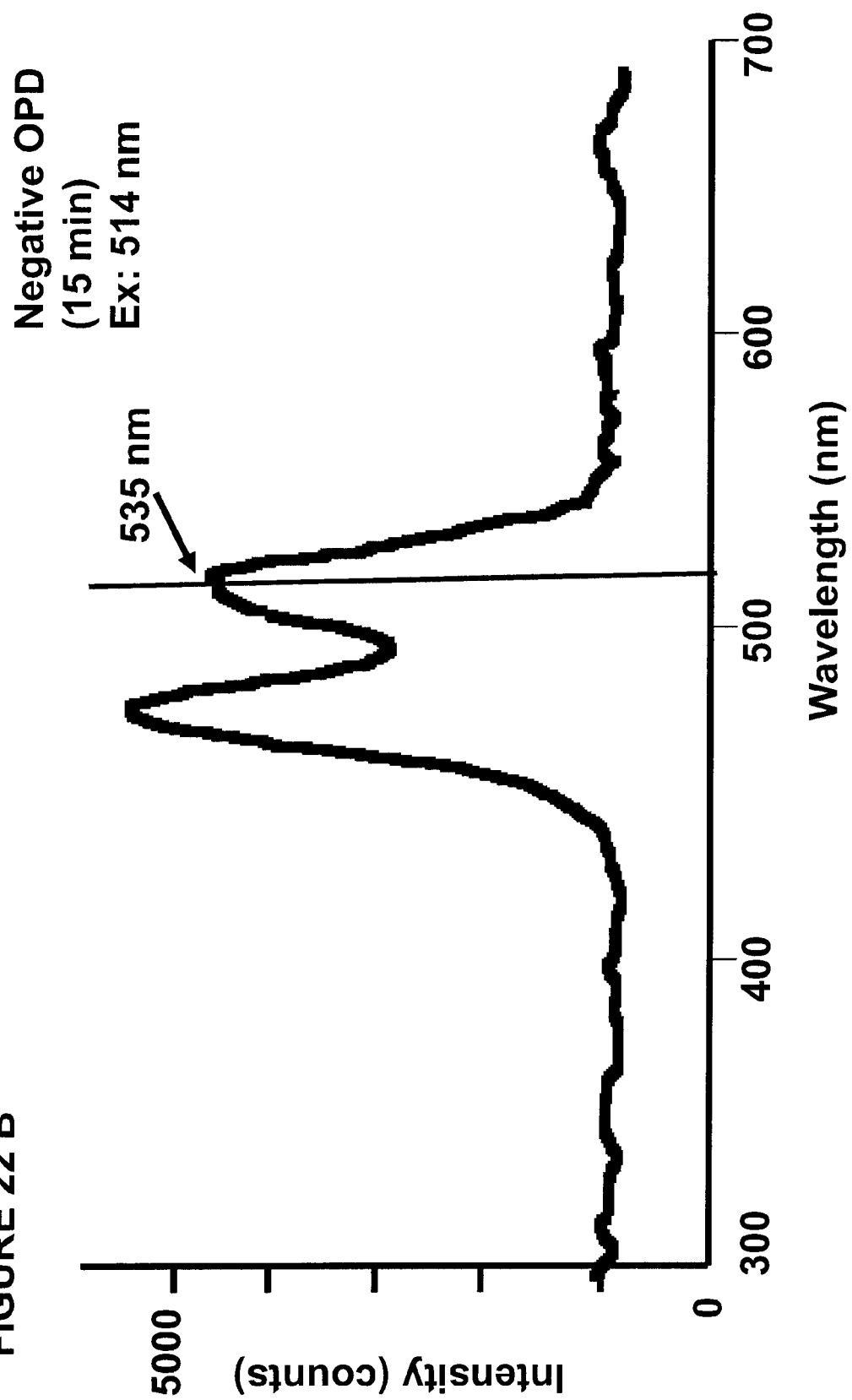
Figure 22:
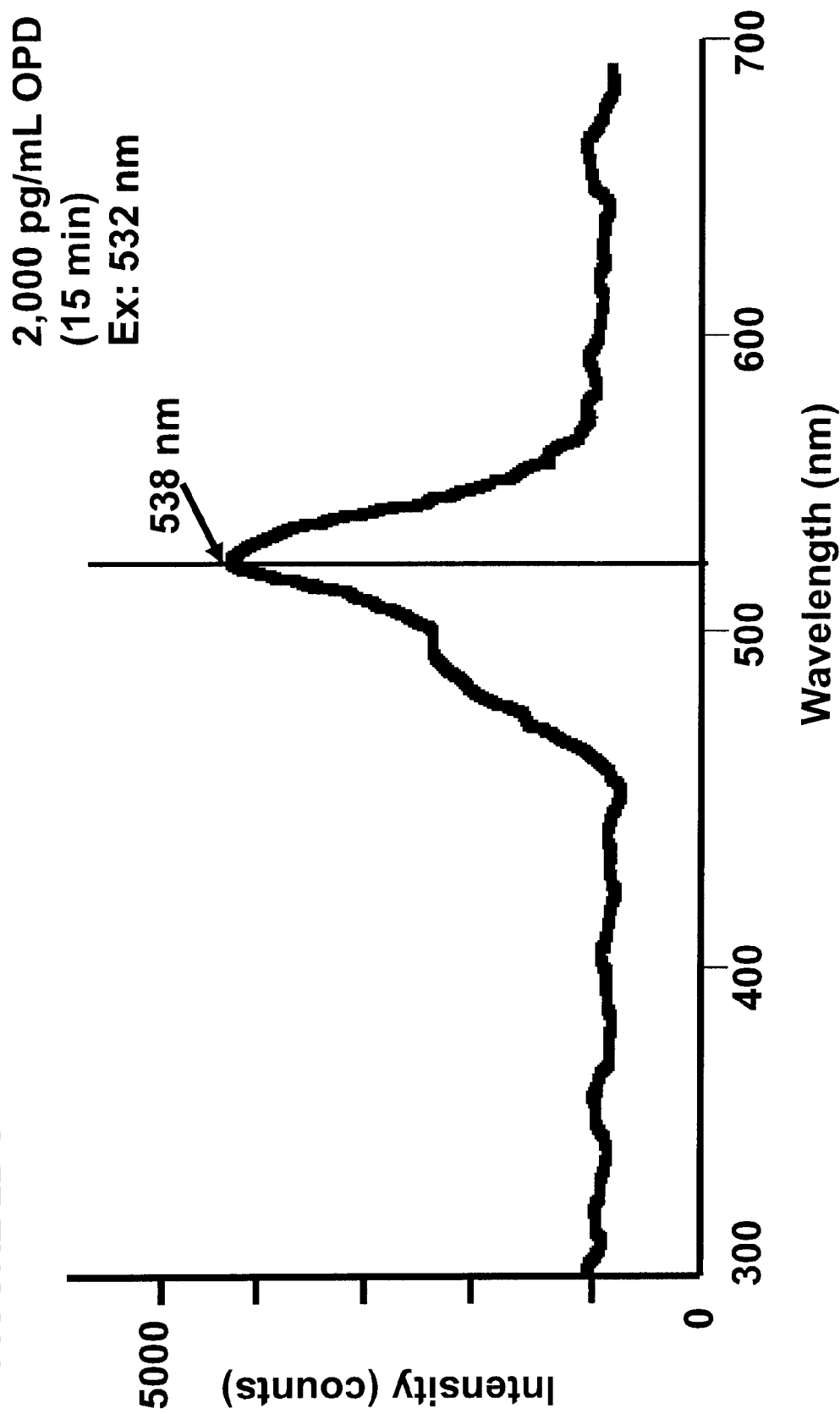
Figure 22:
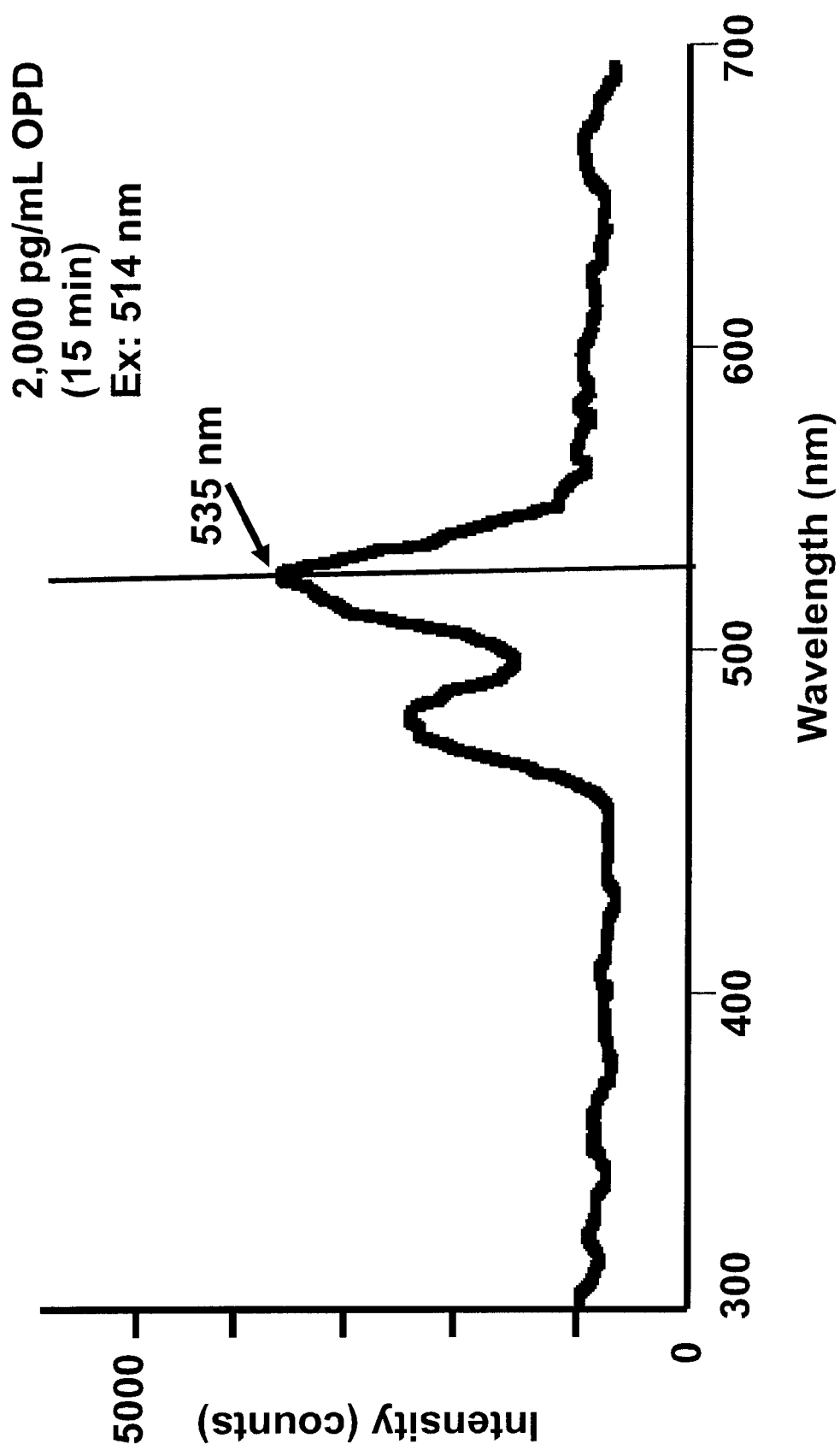

Scans were performed with an Ocean Optics USB 2.0 Fiber Optic lens with a 200 nm split and equipped with Spectrasuite software. Spectra were generated using excitation wavelengths of either 514 or 532 nm. Emission spectra were collected using 12 second integration and a box width of 30. Emission spectra are shown in FIGS. 21 A-D. The fluorescence emission spectra of both the negative (0 pg/ml peroxidase) and reactive (2,000 pg/ml peroxidase) BASH reactions were similar (FIGS. 21 A and B), with a low level of inherent fluorescence. The OPD reaction fluorescence spectra were similar (FIGS. 22 A-D).

Raman.

Figure 23:
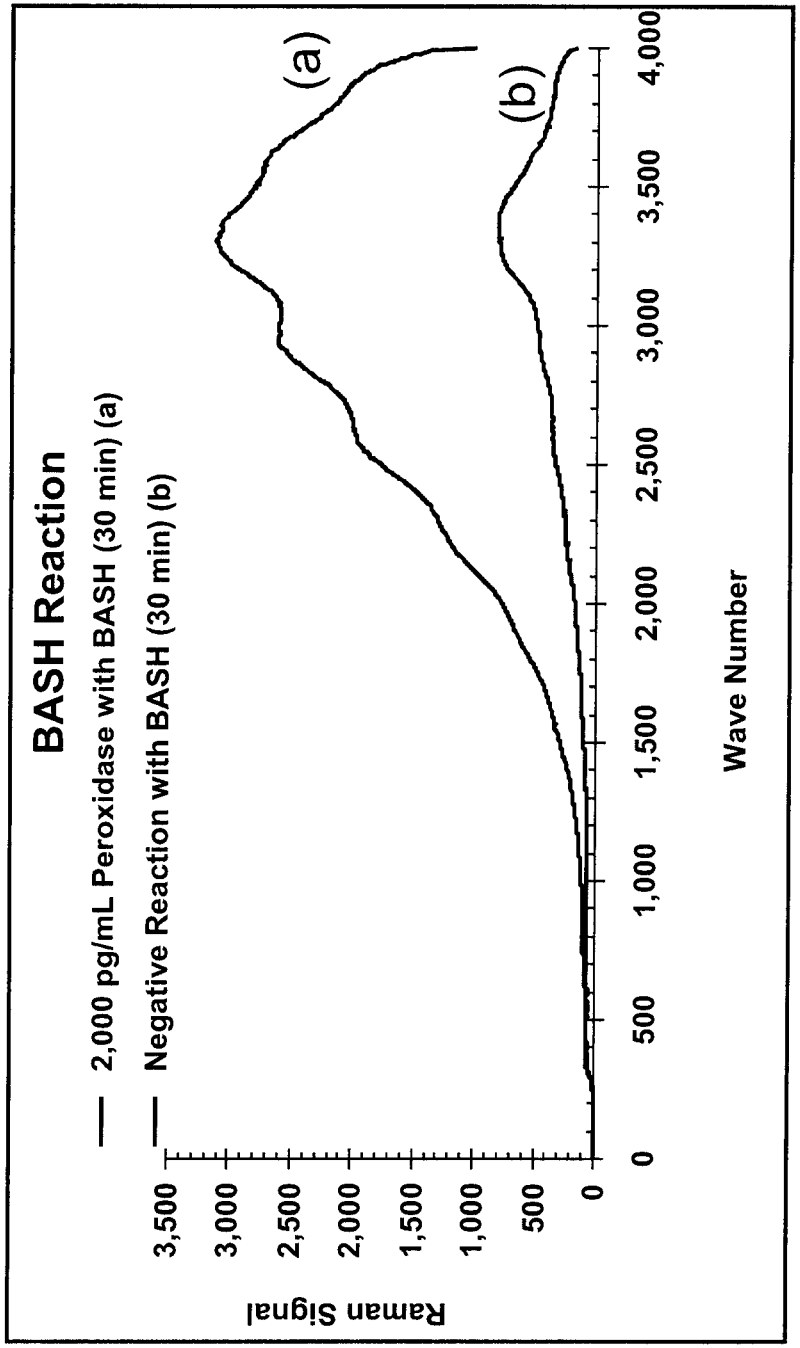
FIGS. 23 A and 23 B are plots of Raman signals produced by BASH-UP and OPD reactions, respectively.
Figure 23:
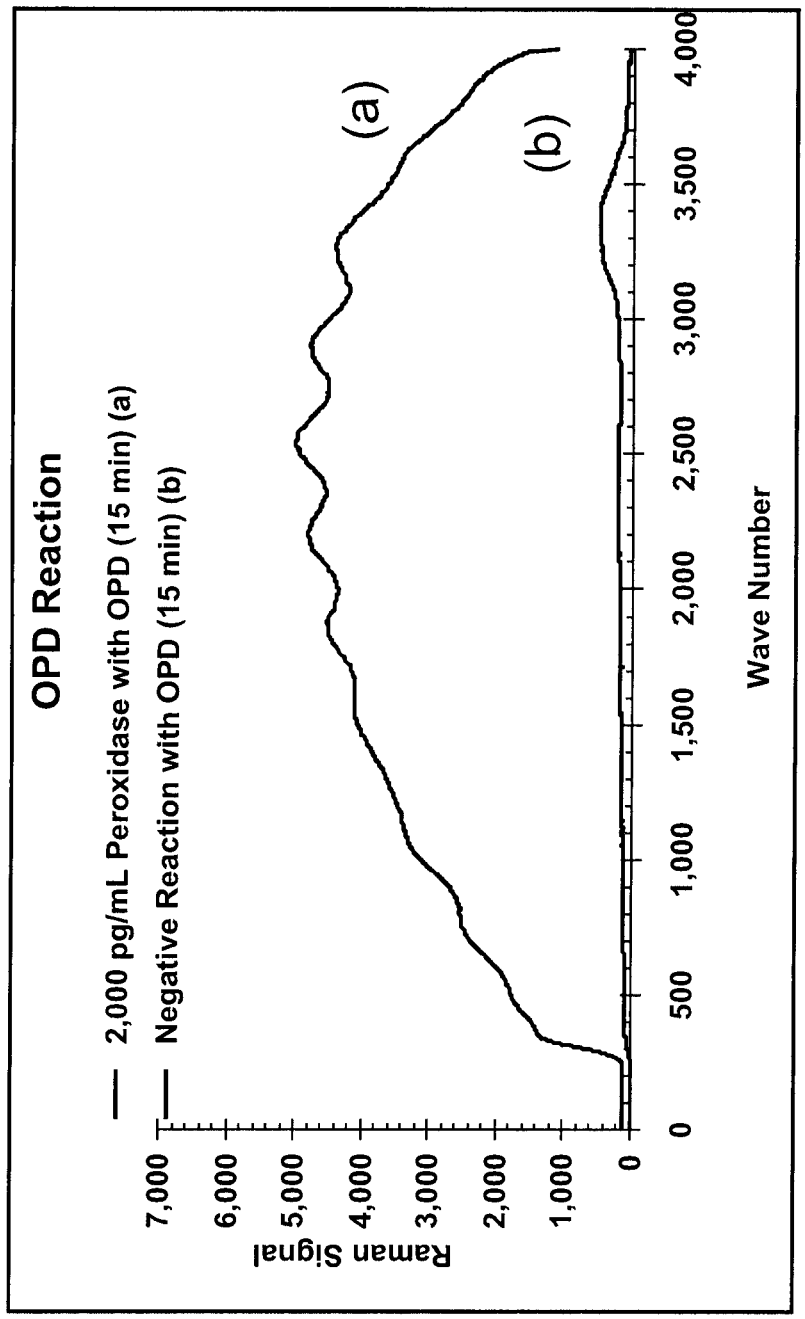

Spectra were collected on a Sword Diagnostics Raman Systems INC QE 65000 Raman Detector with a 532 nm laser; spectra of each reaction are shown in FIGS. 30 and 31. The BASH reaction resulted in a large Raman signal (FIG. 23 A). This BASH reaction had a characteristic light pink color associated with large peroxidase-containing samples. The OPD reaction also resulted in a large Raman signal (FIG. 23 B), and had a characteristic yellow color also associated with large peroxidase-containing samples. No increase in fluorescence signal was observed corresponding to the increase in Raman signal. In fact, there appeared to be a slight decrease in fluorescence signal observed when peroxidase was present. These observations were consistent at emission wavelengths of 514 and 532 nm.

These results show that neither BASH reactions, nor OPD reactions which resulted in large peroxidase dependent Raman signals, showed large peroxidase dependent fluorescence signals. Therefore fluorescence cannot account for the Raman signals detected as a result of Peroxidase activity in the BASH or OPD reactions.

Example 12

Raman Sensitivity of OPD-Peroxidase Reactions and Measurements of Enzyme Kinetics Studies were done to evaluate and characterize the Raman signal associated with the OPD-peroxidase reaction. The following procedure was used for sample preparation:

OPD Reaction:
1. prepare OPD substrate solutions per SIGMAFAST™ OPD instructions;
2. prepare 3M $H_2SO_4$ stop solution;
3. prepare peroxidase dilutions in buffer (PBS BSA) to 4,000 pg/ml;
4. prepare the OPD/peroxide substrate solution (substrate solution should be used within one hour of preparation);
5. add 50 µl diluted peroxidase sample to each reaction tube;
6. add 150 µl OPD/peroxide substrate to each tube;
7. mix and incubate for 30 min in the dark at room temperature;
8. add 50 µl of 3M $H_2SO_4$ stop solution, 50 µl 0.5 N NaOH or 50 µl of 1× PBS-BSA solution to each reaction tube.

The following reaction mixtures were prepared in 5×60 mm cuvettes. Each mixture was prepared and measured for 30 min prior to preparation of the next reaction. Fresh OPD substrate was prepared each hour. The reactions used are shown in Table 21:

TABLE 21

| OPD REACTIONS | |
|---|---|
| Reaction No. | Composition |
| 1 | 50 µl peroxidase (at 250 pg/ml conc.) + 150 µl OPD-peroxide substrate |
| 2 | 50 µl peroxidase (at 50 pg/ml conc.) + 150 µl OPD-peroxide substrate |
| 3 | 50 µl peroxidase (at 5 pg/ml conc.) + 150 µl OPD-peroxide substrate |
| 4 | 50 µl of 1 x PBS-BSA + 150 µl OPD-peroxide substrate |

Figure 24:
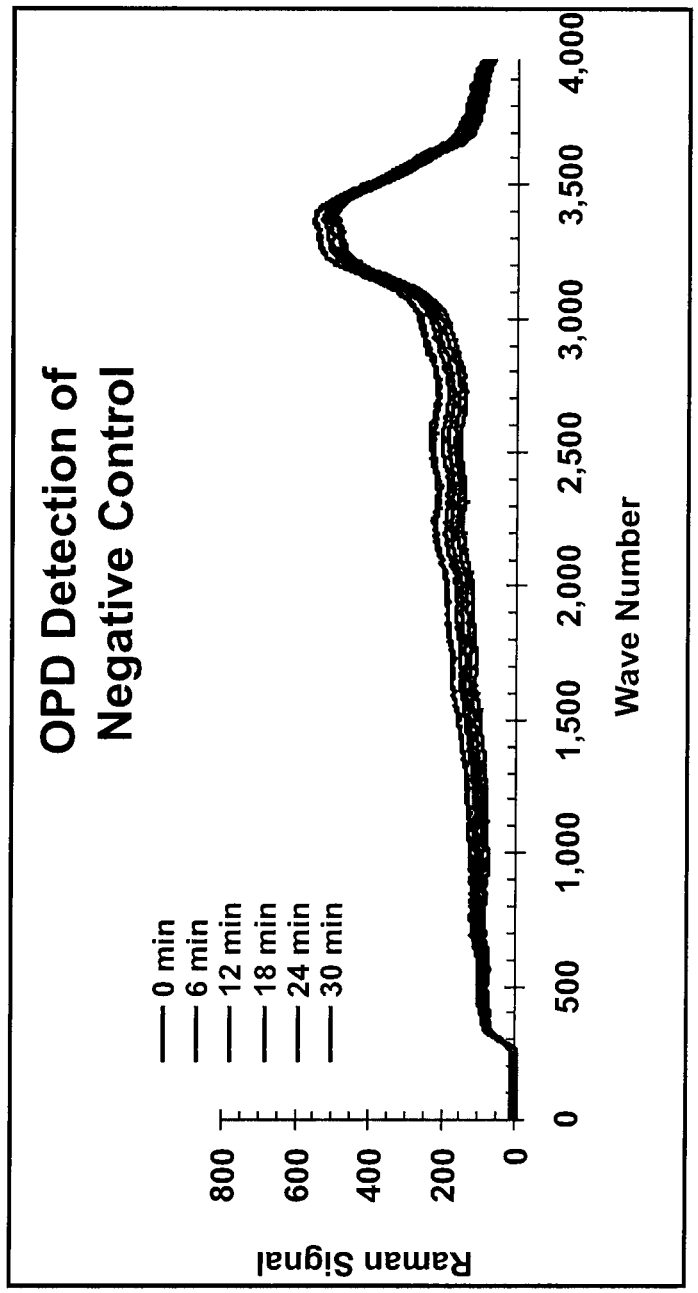
FIG. 24 A is a plot of Raman signals over time for an OPD reaction without peroxidase, and FIGS. 24 A-E are plots of Raman signals over time for OPD reactions with decreasing amounts of peroxidase.
Figure 24:
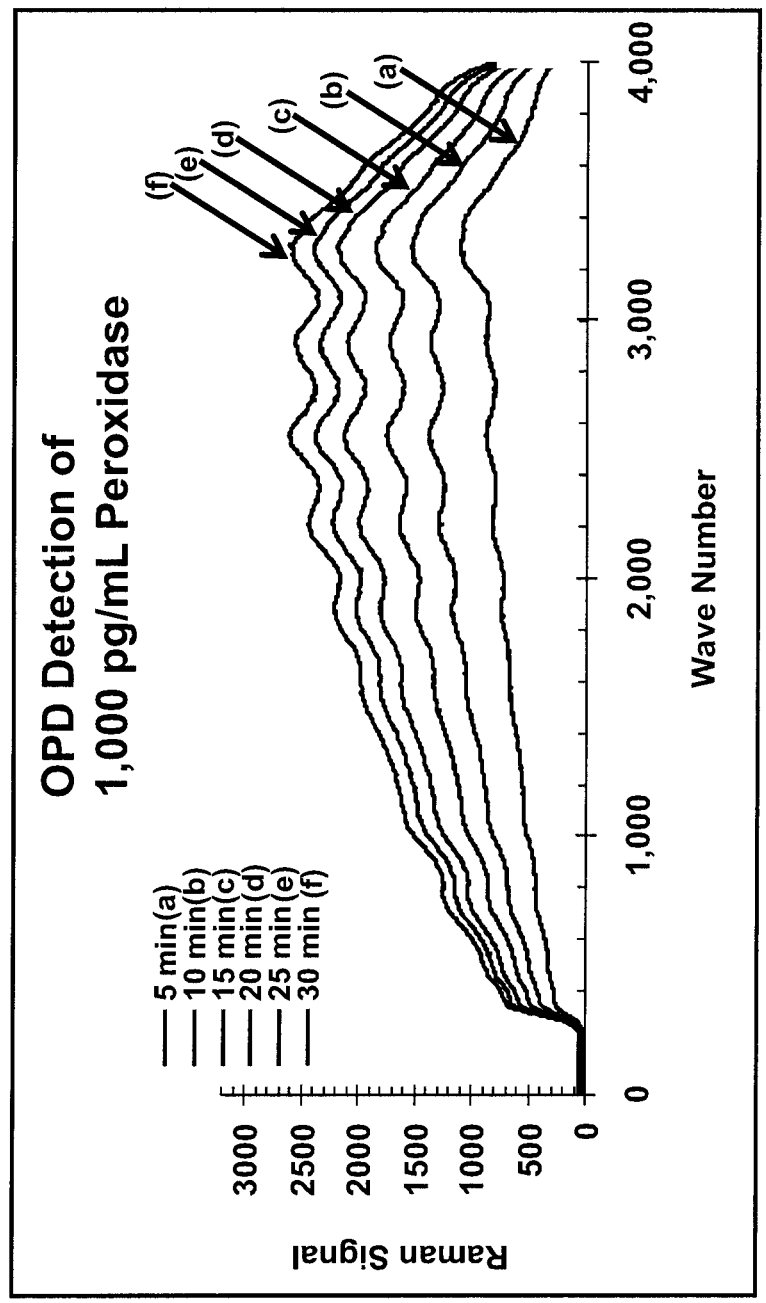
Figure 24:
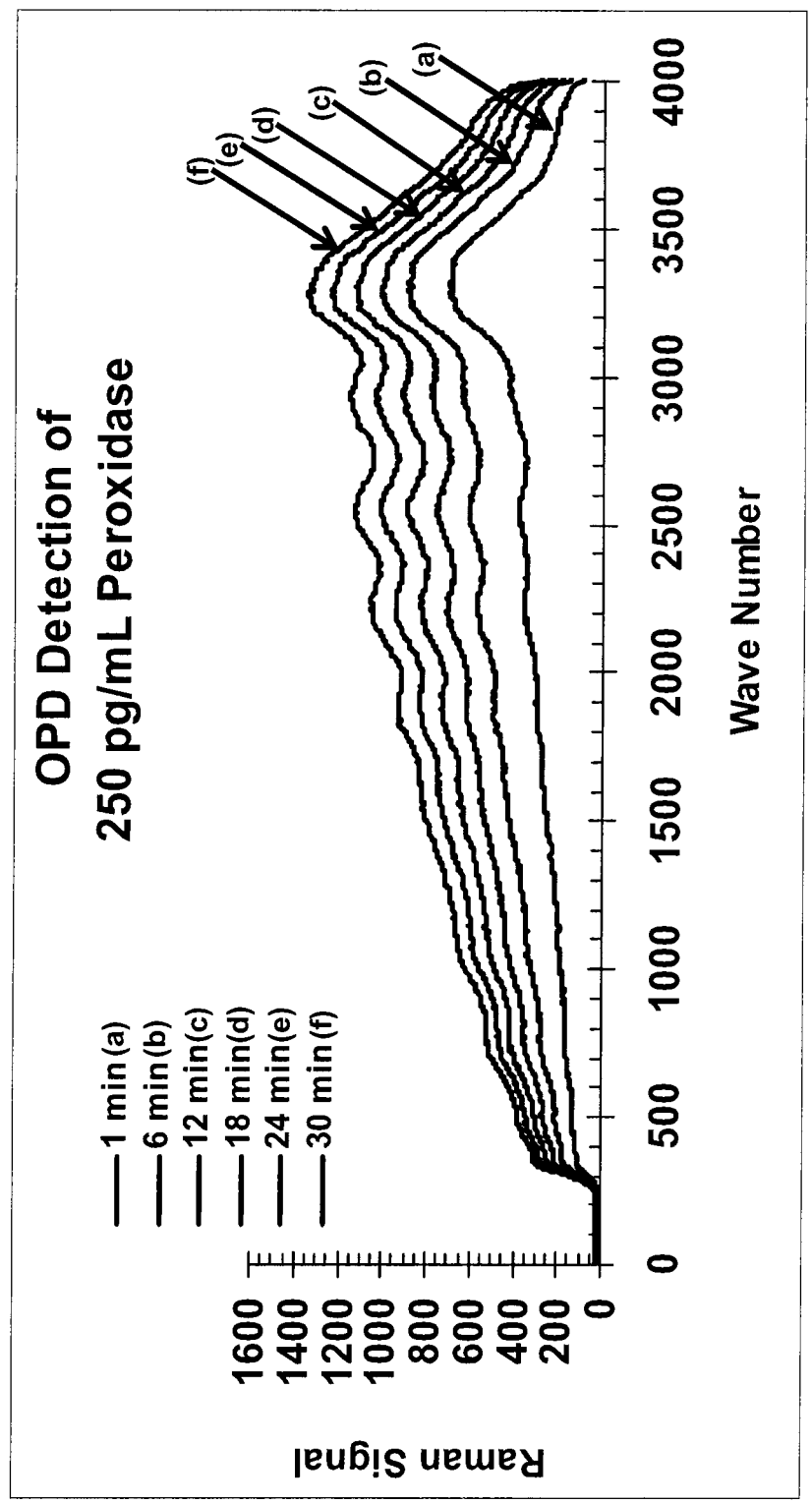
Figure 24:
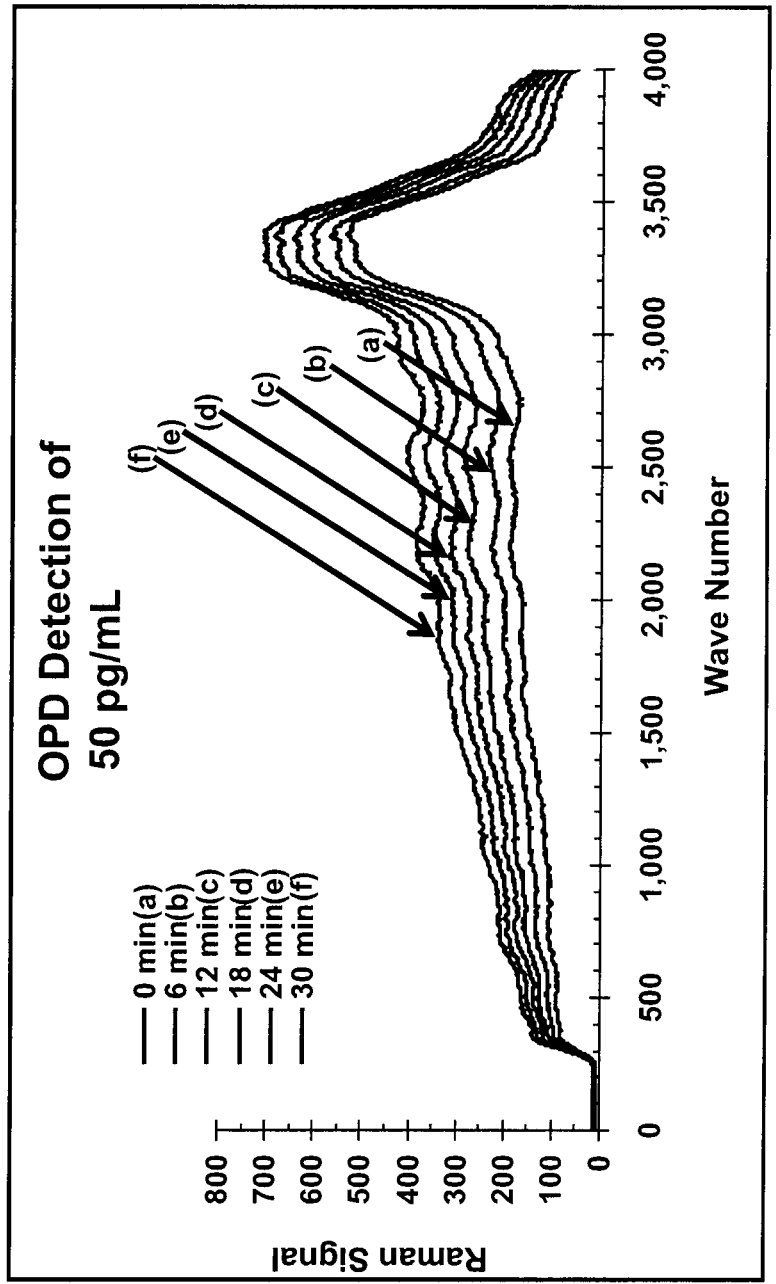
Figure 24:
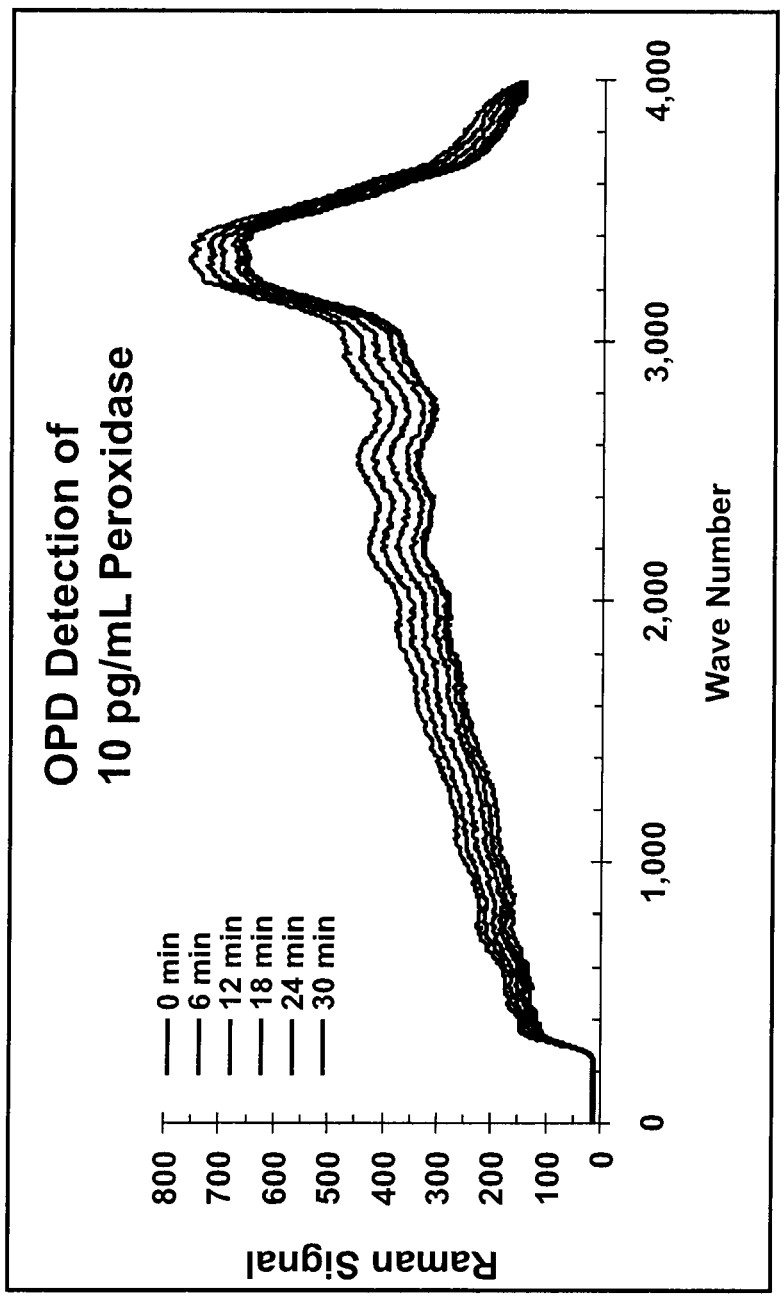

Kinetic studies were performed on each reaction, collecting Raman spectra every 2 mins. FIGS. 24 A-E show spectra collected in approximately 5-6 min intervals.

Figure 25:
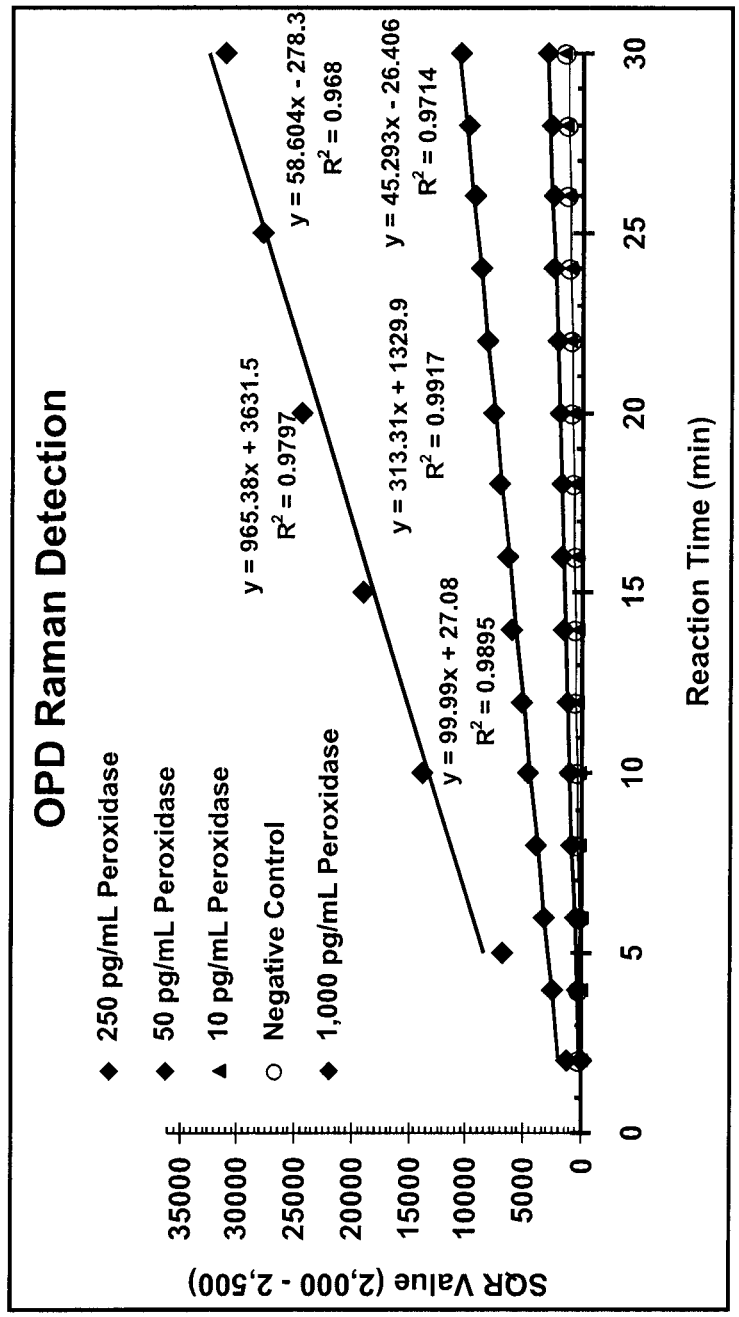
FIGS. 25 A-D are plots of SQR spectra over time for OPD reactions.
Figure 25:
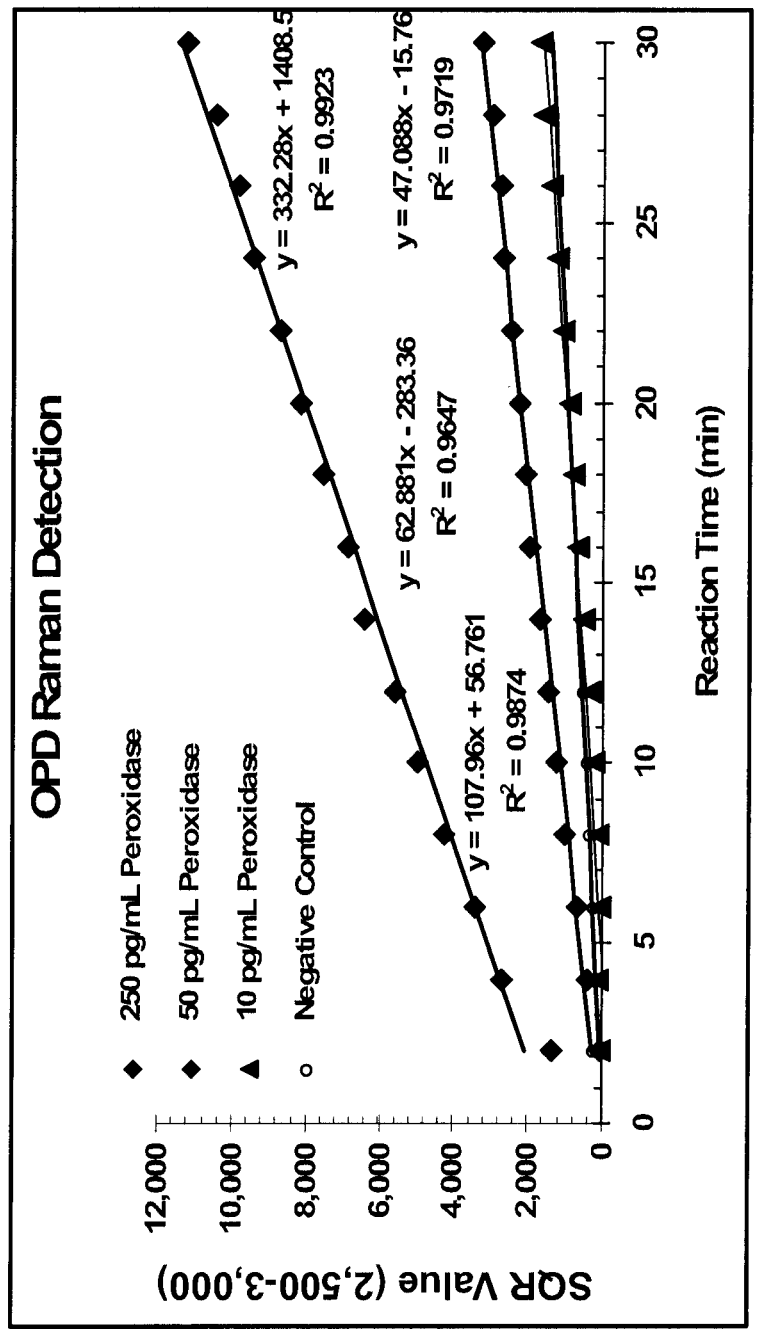
Figure 25:
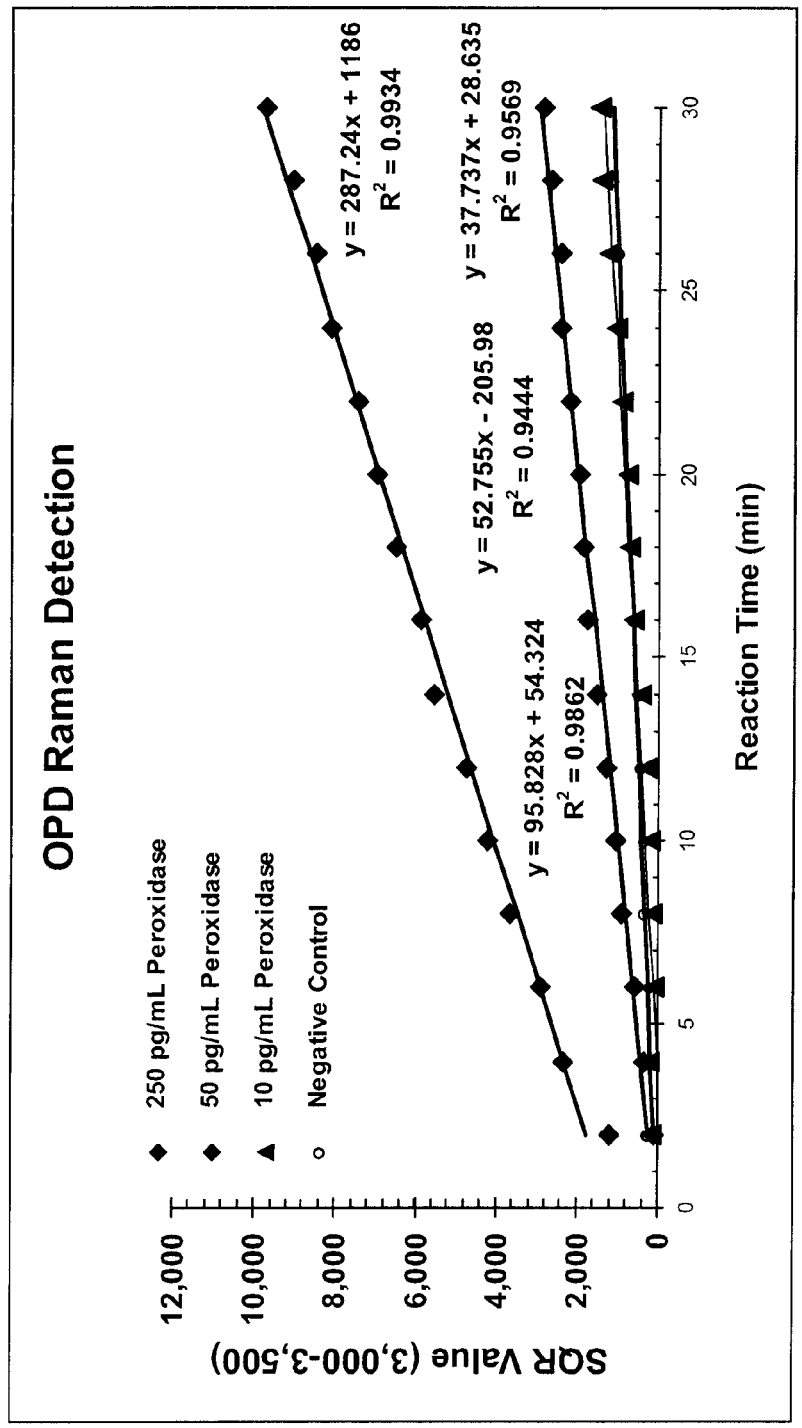
Figure 25:
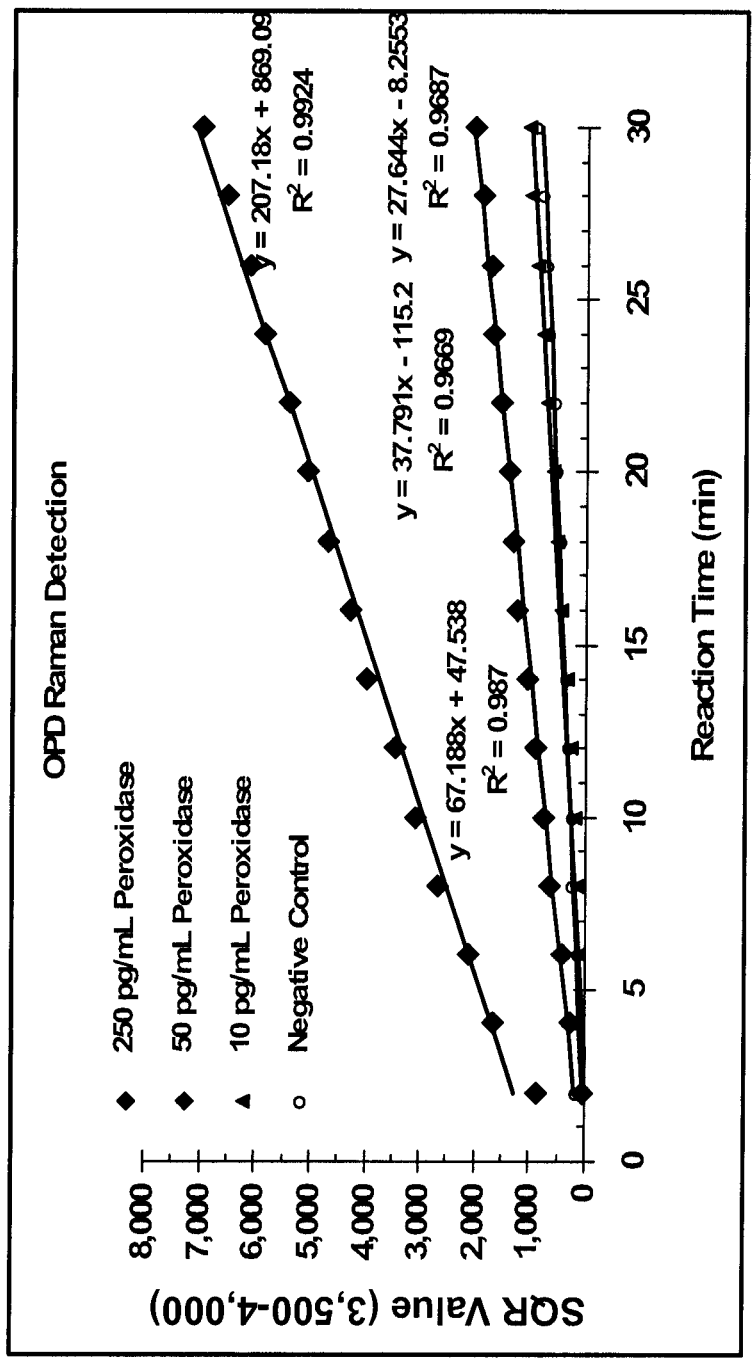

SQR analysis was applied to the collected spectra for the following wavelength ranges: 2,000-2,500 $cm^{-1}$; 2,500-3,000 $cm^{-1}$; 3,000-3,500 $cm^{-1}$; and 3,500-4,000 $cm^{-1}$. The Raman kinetic plots of SQR spectra vs. OPD-peroxidase reaction time are shown in FIGS. 25 A-D. These results show that kinetic rate information may be collected from single-tube OPD-peroxidase reactions (collecting multiple Raman spectra during the course of a reaction from a single reaction tube).

The SQR values obtained after 30 minutes of reaction time were compared to the estimated rate of reaction calculated by SQR, which revealed a good correlation between these values over a wide range of wave numbers.

The invention claimed is:

1. A method for detecting the activity of at least one enzyme in a sample comprising:
   a) preparing a mixture comprising the sample and:
      i. optionally at least one aromatic compound;
      ii. at least one amine-containing compound; and
      iii. at least one electron-donating compound;
   b) incubating the mixture in the presence of a base to form at least one Raman-active product; and
   c) detecting the at least one Raman-active product with Raman spectroscopy,
   wherein the method does not comprise Surface Enhanced Resonance Raman Scattering (SERRS).

2. The method of claim 1, wherein the at least one amine-containing compound is chosen from 4-aminoantipyrene and 5-aminosalicyclic acid.

3. The method of claim 1, wherein the at least one aromatic compound is chosen from 2-hydroxybenzyl alcohol, 4-chloro-3,5-dimethylphenol, 2-naphthol, 4-hydroxy-4-biphenyl-carboxylic acid, 5,7dichloro-8-hydroxyquinoline, 4-chloro-1-naphthol, phenol, and 4,5 dihydroxy-naphthelene-2,7-disulfonic acid.

4. The method of claim 1, wherein the at least one amine-containing compound comprises:

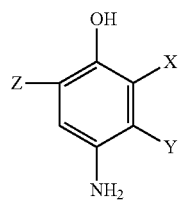

wherein X is chosen from H, $NH_2$, Cl, Br, nitro, and benzyl, Y is chosen from H, Cl, Br, and nitro, and Z is chosen from H, benzyl, and $NH_2$.

5. The method of claim 1, wherein the at least one amine-containing compound comprises:

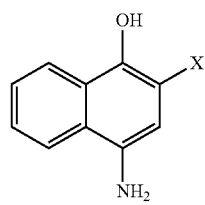

wherein X is chosen from H, OH, Cl, Br, and nitro.

6. The method of claim 1, wherein the amine-containing compound comprises:

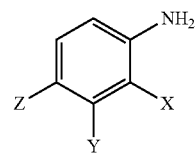

wherein X, Y, and Z are chosen from H and $NH_2$.

7. The method of claim 1, wherein the at least one aromatic compound comprises:

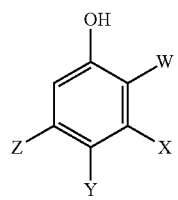

wherein W, X, Y, and Z are chosen from H and OH.

8. The method of claim 1, wherein the at least one aromatic compound comprises:

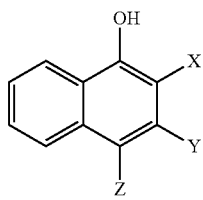

wherein X, Y, and Z are chosen from H and OH.

9. The method of claim 1, wherein the at least one aromatic compound comprises:

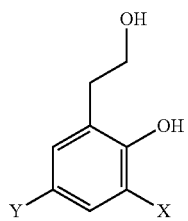

wherein X and Y are chosen from H and OH.

10. The method of claim 1, wherein the at least one aromatic compound comprises:

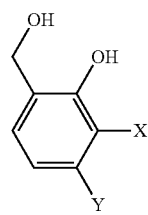

wherein X and Y are chosen from H and OH.

11. The method of claim 1, wherein the at least one electron-donating compound is chosen from an organic hydrogen peroxide, urea hydrogen peroxide, and hydrogen peroxide ($H_2O_2$).

12. The method of claim 1, wherein the at least one enzyme is a peroxidase.

13. The method of claim 1, wherein the at least one aromatic compound is 2-hydroxybenzyl alcohol, the at least one amine containing compound is 5-aminosalicyclic acid, the at least one electron-donating compound is urea hydrogen peroxide, and the at least one enzyme is a peroxidase.

14. The method of claim 1, wherein the Raman spectroscopy is resonance Raman Spectroscopy.

15. A method for detecting the activity of at least one enzyme in a sample comprising:
  a) preparing a mixture comprising the sample, an aromatic amine chosen from o-phenylenediamine, m-phenylenediamine, and p-phenylenediamine, and a hydrogen peroxide chosen from an aromatic hydrogen peroxide, urea hydrogen peroxide, and hydrogen peroxide ($H_2O_2$);
  b) incubating the mixture in the presence of a base to form at least one Raman-active product; and
  c) detecting the at least one Raman-active product with Raman spectroscopy,
  wherein the method does not comprise Surface Enhanced Resonance Raman Scattering (SERRS).

16. The method of claim 15, wherein the aromatic amine is o-phenylenediamine and the hydrogen peroxide is urea hydrogen peroxide.

17. A method for detecting at least one target in a sample comprising:
  a) preparing a mixture comprising the at least one target;
  b) incubating the mixture with at least one ligand specific for the at least one target, wherein the at least one ligand comprises an enzyme;
  c) providing to the mixture:
    i) optionally at least one aromatic compound;
    ii) at least one amine-containing compound; and
    iii) at least one electron-donating compound;
  d) incubating the mixture in the presence of a base to form at least one Raman-active product; and
  e) detecting the at least one Raman-active product with Raman spectroscopy,
  wherein the method does not comprise Surface Enhanced Resonance Raman Scattering (SERRS).

18. The method of claim 17, wherein the at least one amine-containing compound is chosen from 4-aminoantipyrene and 5-aminosalicyclic acid.

19. The method of claim 17, wherein the at least one aromatic compound is chosen from 2-hydroxybenzyl alcohol, 4-chloro-3,5-dimethylphenol, 2-naphthol, 4-hydroxy-4-biphenyl-carboxylic acid, 5,7-dichloro-8-hydroxyquinoline, 4-chloro-1-naphthol, phenol, and 4,5 dihydroxy-naphthelene-2,7-disulfonic acid.

20. The method of claim 17, wherein the at least one amine-containing compound comprises

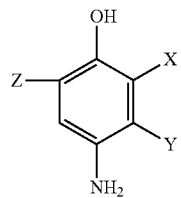

wherein X is chosen from H, $NH_2$, Cl, Br, nitro, and benzyl, Y is chosen from H, Cl, Br, and nitro, and Z is chosen from H, benzyl, and $NH_2$.

21. The method of claim 17, wherein the at least one amine-containing compound comprises

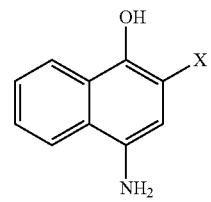

wherein X is chosen from H, OH, Cl, Br, and nitro.

22. The method of claim 17, wherein the at least one amine-containing compound comprises

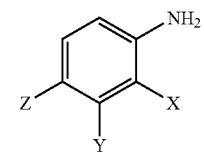

wherein X, Y, and Z are chosen from H and $NH_2$.

23. The method of claim 17, wherein the at least one aromatic compound comprises

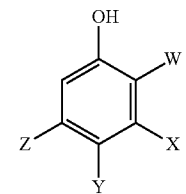

wherein W, X, Y, and Z are chosen from H and OH.

24. The method of claim 17, wherein the at least one aromatic compound comprises

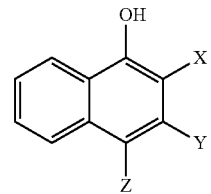

wherein X, Y, and Z are chosen from H and OH.

25. The method of claim 17, wherein the at least one aromatic compound comprises

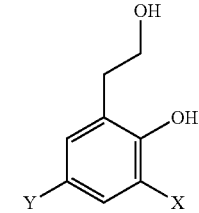

wherein X and Y are chosen from H and OH.

26. The method of claim 17, wherein the at least one aromatic compound comprises

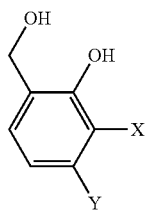

wherein X and Y are chosen from H and OH.

27. The method of claim 17, wherein the at least one electron-donating compound is chosen from an organic hydrogen peroxide, urea hydrogen peroxide, and hydrogen peroxide ($H_2O_2$).

28. The method of claim 17, wherein the enzyme is a peroxidase.

29. The method of claim 17, wherein the at least one aromatic compound is 2-hydroxybenzyl alcohol, the amine-containing compound is 5-aminosalicyclic acid, the electron-donating compound is urea hydrogen peroxide, the at least one enzyme is a peroxidase, and the ligand is an antibody.

30. The method of claim 17, wherein the Raman spectroscopy is resonance Raman Spectroscopy.

31. The method of claim 17, wherein the at least one target is an organism.

32. The method of claim 31, wherein the organism is chosen from *E. coli, Listeria, Salmonella, Vibrio, Camphelbacter, Staphylococcus*, HIV, Hepatitis, Adenovirus, Rhino virus, and Human papilloma virus.

33. The method of claim 17, wherein the target is chosen from a protein, amino acids, nucleic acids, nucleotides, carbohydrates, metabolites, hormones, and metabolic intermediates.

34. The method of claim 33, wherein the protein is chosen from IL-2, C-Reactive protein, Tumor Necrosis Factor Receptor II, and Human Cardiac Troponin I.

35. A method for detecting the activity of at least one enzyme in a sample comprising:
 a) preparing a mixture comprising the sample and:
  i) optionally at least one aromatic compound;
  ii) at least one amine-containing compound; and
  iii) at least one electron-donating compound;
 b) incubating the mixture in the presence of a base to form at least one charge transfer complex; and
 c) detecting the at least one charge transfer complex with Raman spectroscopy,
 wherein the method does not comprise Surface Enhanced Resonance Raman Scattering (SERRS).

UNITED STATES PATENT AND TRADEMARK OFFICE
CERTIFICATE OF CORRECTION

PATENT NO. : 9,260,742 B2  Page 1 of 1
APPLICATION NO. : 13/040679
DATED : February 16, 2016
INVENTOR(S) : Siegel et al.

It is certified that error appears in the above-identified patent and that said Letters Patent is hereby corrected as shown below:

In the claims

Claim 3, col. 35, line 36,

"5,7dichloro-8-hydroxyquinoline" should read

--5,7-dichloro-8-hydroxyquinoline--.

Claim 3, col. 35, line 37,

"4,5 dihydroxy-naphthelene-2,7-disulfonic acid" should read

--4,5-dihydroxynaphthelene-2,7-disulfonic acid--.

Claim 19, col. 37, lines 50-51,

"4,5 dihydroxy-naphthelene-2,7-disulfonic acid" should read

--4,5-dihydroxynaphthelene-2,7-disulfonic acid--.

Signed and Sealed this
Third Day of May, 2016

Michelle K. Lee
*Director of the United States Patent and Trademark Office*